(12) United States Patent
Skerra et al.

(10) Patent No.: US 8,563,521 B2
(45) Date of Patent: Oct. 22, 2013

(54) BIOLOGICAL ACTIVE PROTEINS HAVING INCREASED IN VIVO AND/OR IN VITRO STABILITY

(75) Inventors: Arne Skerra, Freising (DE); Ina Theobald, Landshut (DE); Martin Schlapschy, Freising (DE)

(73) Assignee: Technische Universitat Munchen, Munich (DE)

( * ) Notice: Subject to any disclaimer, the term of this patent is extended or adjusted under 35 U.S.C. 154(b) by 597 days.

(21) Appl. No.: 12/665,565

(22) PCT Filed: Jun. 20, 2008

(86) PCT No.: PCT/EP2008/005020
§ 371 (c)(1),
(2), (4) Date: Jun. 1, 2010

(87) PCT Pub. No.: WO2008/155134
PCT Pub. Date: Dec. 24, 2008

(65) Prior Publication Data
US 2010/0292130 A1 Nov. 18, 2010

Related U.S. Application Data

(60) Provisional application No. 61/071,705, filed on May 14, 2008.

(30) Foreign Application Priority Data

Jun. 21, 2007 (EP) .................................... 07012219

(51) Int. Cl.
A61K 38/16 (2006.01)
C07K 14/00 (2006.01)
C12N 15/63 (2006.01)
C12N 5/10 (2006.01)
C12P 21/00 (2006.01)

(52) U.S. Cl.
USPC ...... 514/21.2; 514/21.3; 530/350; 435/320.1; 435/325; 435/69.1

(58) Field of Classification Search
None
See application file for complete search history.

(56) References Cited

U.S. PATENT DOCUMENTS 5,677,172 A 10/1997 Makarow
2003/0190740 A1* 10/2003 Altman .......................... 435/226
2012/0230947 A1 9/2012 Schellenberger et al.

FOREIGN PATENT DOCUMENTS

EP 2173890 B1 3/2011
WO WO 02/02597 A2 1/2002
WO WO 2006/081249 A2 8/2006
WO WO 2007/103515 A2 9/2007
WO WO 2010/091122 A1 8/2010

OTHER PUBLICATIONS

The Office Action received in the corresponding European patent application No. 11158295.3 dated Dec. 20, 2011.
Schellenberger, V, "AMUNIX—Engineering of Microproteins for Pharmaceutical Applications," Powerpoint presentation, pp. 1-35, Menlo Park, CA.
Alvarez, et. al., Improving protein pharmacokinetics by genetic fusion to simple amino acid sequences. J Biol Chem, 2004, 279, 3375-81.
Axelsson, et al., Studies of the release and turnover of a human neutrophil lipocalin. Scand J Clin Lab Invest, 1995, 55,577-88.
Bamford, et. al., Synthetic polypeptides, preparation, structure, and properties, Academic Press Inc., 1956.
Binz, et al., Engineering novel binding proteins from nonimmunoglobulin domains. Nat Biotechnol, 2005, 23, 1257-68.
Böhm, et al., Quantitative analysis of protein far UV circular dichroism spectra by neural networks. Protein Eng, 1992, 5, 191-5.
Brant, et al., Conformational energy estimates for statistically coiling polypeptide chains. J. Mol. Biol., 1967, 23,47-65.
Breustedt, et al.,) Comparative ligand-binding analysis of ten human lipocalins. Biochim Biophys Acta, 2006, 1764, 161-73.
Caliceti, et al.,) Pharmacokinetic and biodistribution properties of poly(ethylene glycol)-protein conjugates. Adv Drug Deliv Rev, 2003, 55, 1261-77.
Cantor, et. al., The Conformation of Biological Macromolecules, Biophysical Chemistry, 1996, Part I, pp. 425-428, Part II, pp. 1006-1010.
Carter, et al., Purification, cloning, expression and biological characterization of an interleukin-I receptor antagonist protein. Nature, 1990, 344, 633-8.
Chou, et al., Prediction of protein conformation. Biochemistry, 1974, 13,222-45.
Chu, et al., The hydrophobic pocket of 24p3 protein from mouse uterine luminal fluid: fatty acid and retinol binding activity and predicted structural similarity to lipocalins. J Pept Res., 1998, 52,390-7.
Clark, et al.,) Long-acting growth hormones produced by conjugation with polyethylene glycol. J Biol Chem, 1996, 271, 21969-77.
Cowan, et al., Structure of poly-l-proline, Nature, 1955, pp. 501-503, vol. 176.
Creighton, Thomas E., Proteins structures and molecular properties, European Molecular Biology Laboratory, Second Edition, pp. 190-191, 176-177, 1993.
Dennis, et al., Albumin binding as a general strategy for improving the pharmacokinetics of proteins. J Biol Chem, 2002, 277,35035-43.
Elliott, et al., Enhancement of therapeutic protein in vivo activities through glycoengineering. Nat Biotechnol, 2003, 21, 414-21.

(Continued)

Primary Examiner — Robert A Wax
Assistant Examiner — Jessica Worsham
(74) Attorney, Agent, or Firm — Foley & Lardner LLP

(57) ABSTRACT

Increased in vivo and/or in vitro stability is imparted to a biologically active protein by fusing to an amino acid sequence consisting of at least about 100 amino acid residues, which are Alanine, Serine and Proline, which form a random coil conformation. Specific examples are described. Also described are related nucleic acids, vectors and cells encoding such amino acids; compositions of biologically active proteins fused to a random coil domain, and methods of making and using the compounds and compositions of the invention.

17 Claims, 28 Drawing Sheets

(56) References Cited

OTHER PUBLICATIONS

Figure 2:
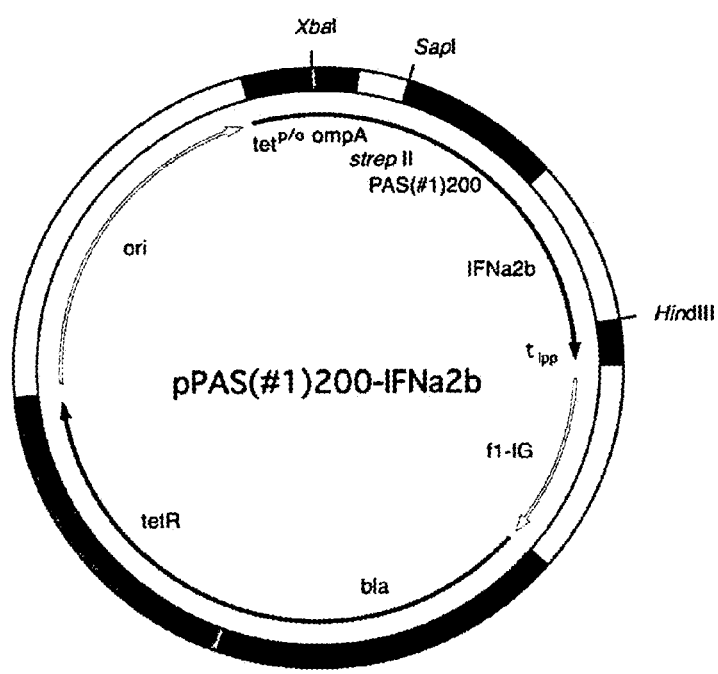

Fandrich, et al., The behaviour of polyamino acids reveals an inverse side chain effect in amyloid structure formation. Embo J., 2002, 21, 5682-90.

Flo, et al., Lipocalin 2 mediates an innate immune response to bacterial infection by sequestrating iron. Nature, 2004, 432, 917-21.

Ghetie, et al., Transcytosis and catabolism of antibody. Immunol Res, 2002, 25, 97-113.

Gill, et al., Calculation of protein extinction coefficients from amino acid sequence data. Anal Biochem, 1989, 182, 319-26.

Goetz, et al.,) The neutrophil lipocalin NGAL is a bacteriostatic agent that interferes with siderophore-mediated iron acquisition. Mol Cell, 2002, 10, 1033-43.

Goldenberg, M. M., Etanercept, a novel drug for the treatment of patients with severe, active rheumatoid arthritis. Clin Ther, 1999, 21, 75-87; discussion 1-2.

Greenfield, et. al., Computed circular dichroism spectra for the evaluation of protein conformation, Biochemistry, 1969, pp. 4108-4116, vol. 8, No. 10.

Harris, et al., Effect of pegylation on pharmaceuticals. Nat Rev Drug Discov., 2003, 2, 214-21.

Holmes, et al., Siderocalin (Lcn 2) also binds carboxymycobactins, potentially defending against mycobacterial infections through iron sequestration. Structure, 2005, 13, 29-41.

Hvidberg, et al., The endocytic receptor megalin binds the iron transporting neutrophil-gelatinase-associated lipocalin with high affinity and mediates its cellular uptake. FEBS Lett, 2005, 579, 773-7.

Makrides, et al., Extended in vivo half-life of human soluble complement receptor type I fused to a serum albumin-binding receptor. J Pharmacol Exp Ther, 1996, 277, 534-42.

Miller, et al., Dimensions of protein random coils. Biochemistry, 1968, 7, 3925-35.

Mori, et al., Endocytic delivery of lipocalin-siderophore-iron complex rescues the kidney from ischemia-reperfusion injury. J Clin Invest, 2005, 115, 610-21.

Nguyen, et al., The pharmacokinetics of an albumin-binding Fab (AB.Fab) can be modulated as a function of affinity for albumin. Protein Eng Des Sel, 2006, 19, 291-7.

Osborn, et al., Pharmacokinetic and pharmacodynamic studies of a human serum albumin-interferon-alpha fusion protein in cynomolgus monkeys. J Pharmacol Exp Ther, 2002, 303, 540-8.

Perlman, et al., Glycosylation of an N-terminal extension prolongs the half-life and increases the in vivo activity of follicle stimulating hormone. J Clin Endocrinol Metab, 2003, 88, 3227-35.

Quadrifoglio, et al., Ultraviolet rotatory properties of polypeptides in solution. II. Poly-L-serine. J Am Chem Soc, 1968, 90, 2760-5.

Radhakrishnan, et al., Zinc mediated dimer of human interferon-alpha 2b revealed by X-ray crystallography. Structure, 1996, 4, 1453-63.

Ray, et al., A simple procedure for removing contaminating aldehydes and peroxides from aqueous solutions of polyethylene glycols and of nonionic detergents that are based on the polyoxyethylene linkage. Anal Biochem, 1985, 146, 307-12.

Rosendahl, et al., Site-Specific Protein PEGylation. BioProcess International, 2005, 3, 52-61.

Schimmel, et al., Conformational energy and configurational statistics of poly-L-proline. Proc Natl Acad Sci USA, 1967, 58, 52-9.

Schiweck, et al., Fermenter production of an artificial fab fragment, rationally designed for the antigen cystatin, and its optimized crystallization through constant domain shuffling. Proteins, 1995, 23, 561-5.

Schlapschy, et al., A system for concomitant overexpression of four periplasmic folding catalysts to improve secretory protein production in *Escherichia coli*. Protein Eng Des Sel, 2006, 19,385-90.

Schreuder, et al., A new cytokine-receptor binding mode revealed by the crystal structure of the IL-I receptor with an antagonist. Nature, 1997, 386, 194-200.

Shental-Bechor, et al., Monte Carlo studies of folding, dynamics, and stability in alpha-helices. Biophys J, 2005, 88, 2391-402.

Skerra, A. Use of the tetracycline promoter for the tightly regulated production of a murine antibody fragment in *Escherichia coli*. Gene, 1994, 151, 131-5.

Skerra, A., Engineered protein scaffolds for molecular recognition. J Mol Recognit, 2000, 13, 167-87.

Skerra, et al., Use of the Strep-Tag and streptavidin for detection and purification of recombinant proteins. Methods Enzymol, 2000, 326, 271-304.

Smith, et al., The concept of a random coil. Residual structure in peptides and denatured proteins. Fold Des, 1996, 1, R95-106.

Squire, P. G., Calculation of hydrodynamic parameters of random coil polymers from size exclusion chromotography and comparison with parameters by conventional methods. Journal of Chromatography, 1981, 5,433-442.

Walsh, G., Biopharmaceutical benchmarks—2003. Nat Biotechnol, 2003, 21, 865-70.

Walsh, G., Second-generation biopharmaceuticals. Eur. J Pharm Biopharm, 2004, 58, 185-96.

Wood, W.B., Host specificity of DNA produced by *Escherichia coli*: bacterial mutations affecting the restriction and modification of DNA. J Mol Biol, 1966, 16, 118-33.

Yang, et al., An iron delivery pathway mediated by a lipocalin. Mol Cell, 2002, 10, 1045-56.

Yanisch-Perron, et al., Improved M13 phage cloning vectors and host strains: nucleotide sequences of the M13mp18 and pUC19 vectors. Gene, 1985, 33, 103-19.

The International Search Report of the corresponding application PCT/EP2008/005020, dated Oct. 22, 2008.(5 pgs.).

"Cell Therapeutics Inc.'s Polyglutamate (PG) Technology Highlighted at International Polymer Meeting; Novel Recombinant Technology Extends PG Platform to G-CSF," PR Newswire, 2002, pp. 1-2, http://www.cticseattle.com/.

Affranchino, J.L., et al., "Indentification of a *Trypanosoma cruzi* antigen that is shed during the acute phase of Chagas' disease," Molecular and Biochemical Parasitology, 1989, pp. 221-228, vol. 34.

Buscaglia, C.A., et al., "Tandem Amino Acid Repeats From *Trypanosoma cruzi* Shed Antigens Increase the Half-Life of Proteins in Blood," Blood, The American Society of Hematology, 1999, pp. 2025-2032, vol. 93, No. 6.

Buscaglia, C.A., et al., "The Repetitive Domain of *Trypanosoma cruzi trans*-Sialidase Enhances the Immune Response against the Catalytic Domain," The Journal of Infectious Diseases, 1998, pp. 431-436, vol. 177.

Kojima, Y., et al., "Conjugation Cu,Zn-Superoxide Dismutase with Succinylated Gelatin: Pharmacological Activity and Cell-Lubricating Function," BloconJugate Chem., American Chemical Society, 1993, pp. 490-498, vol. 4.

Macewan S.R., et al., Invited Review Elastin-Like Polypeptides: Biomedical Applications of Tunable Biopolymers, PeptideScience, 2010, pp. 60-77, vol. 94, No. 1.

Plückthun, A., IBC Conference on "Antibodies and Beyond Antibodies", Loews Coronado Bay Resort, Coronado, CA, Jun. 1-2, 2006. www.IBCLifeSciences.com/3198, pp. 1-6.

Schellenberger, V, "Amunix—Engineering of Microproteins for Pharmaceutical Applications," Powerpoint presentation, pp. 1-35, Menlo Park, CA, 2006.

Schellenberger, V., et al., "A recombinant polypeptide extends the in vivo half-life of peptides and proteins in a tunable manner," Nature Biotechnology, 2009, pp. 1186-1190, vol. 27, No. 12.

(56) References Cited

OTHER PUBLICATIONS

Schlapschy, M., et al., "Fusion of a recombinant antibody fragment with a homo-amino-acid polymer: effects on biophysical properties and prolonged plasma half-life," Protein Engineering, Design & Selection, 2007, pp. 273-284, vol. 20, No. 6.

Shamji M.F., et al., "Development and Characterization of a Fusion Protein Between Thermally Responsive Elastin-like Polypeptide and Interleukin-1 Receptor Antagonist," Arthritis & Rheumatism, 2007, pp. 3650-3661, vol. 56, No. 11.

Singer, J.W., "Paclitaxel poliglumex (XYOTAX™, CT-2103): A macromolecular taxane," Journal of Controlled Release, 2005, pp. 120-126, vol. 109.

Breustedt et al., The 1.8-A crystal structure of human tear lipocalin reveals an extended branched cavity with capacity for multiple ligands, J Biol Chem, 2005, 280, 484-493.

Bullock et al., XLI-Blue: A High Efficiency Plasmid Transforming recA *Escherichia coli* Strain With Beta-Galactosidase Selection, BioTechniques, 1987, 5, 376-378.

Schlapschy et. al., Fusion of a recombinant antibody fragment with a homo-amino-acid polymer: effects on biophysical properties and prolonged plasma half-life, Protein Engineering, Design & Selection, 2007, 20, 273-284.

Walker et. al., Using protein-based motifs to stabilize peptides, Journal of Peptide Research, 2003, 62, 214-226.

* cited by examiner

Figure 1

A

```
gccTCTCCAGCTGCACCTGCTCCAGCAAGCCCTGCTGCACCAGCTCCGTCTGCTCCTGCT
   ||||||||||||||||||||||||||||||||||||||||||||||||||||||||||
   AGAGGTCGACGTGGACGAGGTCGTTCGGGACGACGTGGTCGAGGCAGACGAGGACGAcgg
   AlaSerProAlaAlaProAlaProAlaSerProAlaAlaProAlaProSerAlaProAlaAla
```

B

```
gccGCACCTGCTTCTCCGGCTCCAGCAGCTCCTAGCGCACCAGCTCCTGCTGCTCCATCT
   ||||||||||||||||||||||||||||||||||||||||||||||||||||||||||
   CGTGGACGAAGAGGCCGAGGTCGTCGAGGATCGCGTGGTCGAGGACGACGAGGTAGAcgg
   AlaAlaProAlaSerProAlaProAlaAlaProSerAlaProAlaProAlaAlaProSerAla
```

C

```
gccCCTTCTTCTCCAAGCCCTTCTGCTCCATCTAGCCCATCTCCTGCATCTCCTAGCTCT
   ||||||||||||||||||||||||||||||||||||||||||||||||||||||||||
   GGAAGAAGAGGTTCGGGAAGACGAGGTAGATCGGGTAGAGGACGTAGAGGATCGAGAcgg
   AlaProSerSerProSerProSerAlaProSerSerProSerProAlaSerProSerSerAla
```

D

```
gccGCTTCTCCAGCAGCTCCTTCTGCTCCACCAGCAGCTGCAAGCCCTGCTGCACCAAGCGCACCTCCTGCT
   ||||||||||||||||||||||||||||||||||||||||||||||||||||||||||||||||||||||
    CGAAGAGGTCGTCGAGGAAGACGAGGTGGTCGTCGACGTTCGGGACGACGTGGTTCGCGTGGAGGACGAcgg
AlaAlaSerProAlaAlaProSerAlaProProAlaAlaAlaSerProAlaAlaProSerAlaProProAlaAla
```

E

```
gccTCTGCTGCAGCACCTGCAGCAGCAAGCGCAGCTGCATCTGCTCCATCTGCAGCTGCT
   ||||||||||||||||||||||||||||||||||||||||||||||||||||||||||
   AGACGACGTCGTGGACGTCGTCGTTCGCGTCGACGTAGACGAGGTAGACGTCGACGAcgg
   AlaSerAlaAlaAlaProAlaAlaAlaSerAlaAlaAlaSerAlaProSerAlaAlaAlaAla
```

F

```
gccGCTGCTGCATCCTCTGCAAGCTCCGCTTCTTCCTCTAGCTCCGCAGCTGCATCTGCT
   ||||||||||||||||||||||||||||||||||||||||||||||||||||||||||
   CGACGACGTAGGAGACGTTCGAGGCGAAGAAGGAGATCGAGGCGTCGACGTAGACGAcgg
   AlaAlaAlaAlaSerSerAlaSerSerAlaSerSerSerSerSerAlaAlaAlaSerAlaAla
```

Figure 2

A

```
                        SapI SapI
                          |   |
         ACCGCGGAGAGTGCTCTTCTGCCTGAAGAGCTTAAGCTTTG
    1610 +---------+---------+---------+---------+ 1650
         TGGCGCCTCTCACGAGAAGACGGACTTCTCGAATTCGAAAC
```

B

C

```
             KasI        SapI
              |           |
         GAAAAAGGCGCCAGCTCTTCTGCCTGTGATCTGCCTCAAACCCACAGCCTGGGTAGC...
     226 ----+---------+---------+---------+---------+---------+-- 282
         CTTTTTCCGCGGTCGAGAAGACGGACACTAGACGGAGTTTGGGTGTCGGACCCATCG...
         GluLysGlyAlaSerSerSerAlaCysAspLeuProGlnThrHisSerLeuGlySer...
                        +1

HindIII
                                                             |
         ...ATGAGATCTTTTTCTTTGTCAACAAACTTGCAAGAAAGTTTAAGAAGTAAGGAATAAGCTT
     691 ---------+---------+---------+---------+---------+---------+- 751
         ...TACTCTAGAAAAAGAAACAGTTGTTTGAACGTTCTTTCAAATTCTTCATTCCTTATTCGAA
            MetArgSerPheSerLeuSerThrAsnLeuGlnGluSerLeuArgSerLysGluEnd
```

Figure 2 Continued...

D

```
         KasI          SapI
          |             |
     GAAAAAGGCGCCAGCTCTTCTGCCTCTCCAGCTGCACCT...CCGTCTGCTCCTGCTGCC
226  ----+---------+---------+---------+----    --------+--------- 849
     CTTTTTCCGCGGTCGAGAAGACGGAGAGGTCGACGTGGA...GGCAGACGAGGACGACGG
     GluLysGlyAlaSerSerSerAlaSerProAlaAlaPro...ProSerAlaProAlaAla
```

```
                                                         HindIII
                                                            |
     TGTGATCTGCCTCAAACCCAC...TTGCAAGAAAGTTTAAGAAGTAAGGAATAAGCTT
850  +---------+----------    --+---------+---------+--------+- 1351
     ACACTAGACGGAGTTTGGGTG...AACGTTCTTTCAAATTCTTCATTCCTTATTCGAA
     CysAspLeuProGlnThrHis...LeuGlnGluSerLeuArgSerLysGluEnd
     (1)
```

E

```
         KasI          SapI
          |             |
     GAAAAAGGCGCCAGCTCTTCTGCCCGACCCTCTGGGAGAAAATCCAGCAAGATGCAA...
226  ----+---------+---------+---------+---------+---------+-- 282
     CTTTTTCCGCGGTCGAGAAGACGGGCTGGGAGACCCTCTTTTAGGTCGTTCTACGTT...
     GluLysGlyAlaSerSerSerAlaArgProSerGlyArgLysSerSerLysMetGln...
                                   +1
```

```
                                                        HindIII
                                                            |
     ...AATATGCCTGACGAAGGCGTCATGGTCACCAAATTCTACTTCCAGGAGGACGAGTAAGCTT
652  ---------+---------+---------+---------+---------+---------+-- 712
     ...TTATACGGACTGCTTCCGCAGTACCAGTGGTTTAAGATGAAGGTCCTCCTGCTCATTCGAA
     ...AsnMetProAspGluGlyValMetValThrLysPheTyrPheGlnGluAspGluEnd
```

F

```
         KasI          SapI
          |             |
     GAAAAAGGCGCCAGCTCTTCTGCCTCTCCAGCTGCACCT...CCGTCTGCTCCTGCTGCC
226  ----+---------+---------+---------+----    --------+--------- 849
     CTTTTTCCGCGGTCGAGAAGACGGAGAGGTCGACGTGGA...GGCAGACGAGGACGACGG
     GluLysGlyAlaSerSerSerAlaSerProAlaAlaPro...ProSerAlaProAlaAla
```

```
                                                        HindIII
                                                            |
     CGACCCTCTGGGAGAAAA...ACCAAATTCTACTTCCAGGAGGACGAGTAAGCTT
850  +---------+-------    -+---------+---------+---------+- 1312
     GCTGGGAGACCCTCTTTT...TGGTTTAAGATGAAGGTCCTCCTGCTCATTCGAA
     ArgProSerGlyArgLys...ThrLysPheTyrPheGlnGluAspGluEnd
     (1)
```

G

Figure 3

A

```
            Eco0109I                                    HindIII
                |                                          |
       CAGTGTATCGAGGCCCCAGCTTGGTCCCACCCGCAGTTCGAAAAATAATAAGCTT
604    ------+---------+---------+---------+---------+-------- 658
       GTCACATAGCTCCGGGGTCGAACCAGGGTGGGCGTCAAGCTTTTTATTATTCGAA
       GlnCysIleGluAlaProAlaTrpSerHisProGlnPheGluLysEnd
```

B

```
       CAGTGTATCGAGGCCTCTCCAGCTGCACCTGCTCCAGCAAGC...
604    ------+---------+---------+---------+----- 645
       GTCACATAGCTCCGGAGAGGTCGACGTGGACGAGGTCGTTCG...
       GlnCysIleGluAlaSerProAlaAlaProAlaProAlaSer...

HindIII
                                                        |
       ...TCTGCTCCTGCTGCCCCAGCTTGGTCCCACCCGCAGTTCGAAAAATAATAAGCTT
1204   ------+---------+---------+---------+---------+-------- 1258
       ...AGACGAGGACGACGGGGTCGAACCAGGGTGGGCGTCAAGCTTTTTATTATTCGAA
       ...SerAlaProAlaAlaProAlaTrpSerHisProGlnPheGluLysEnd
```

C

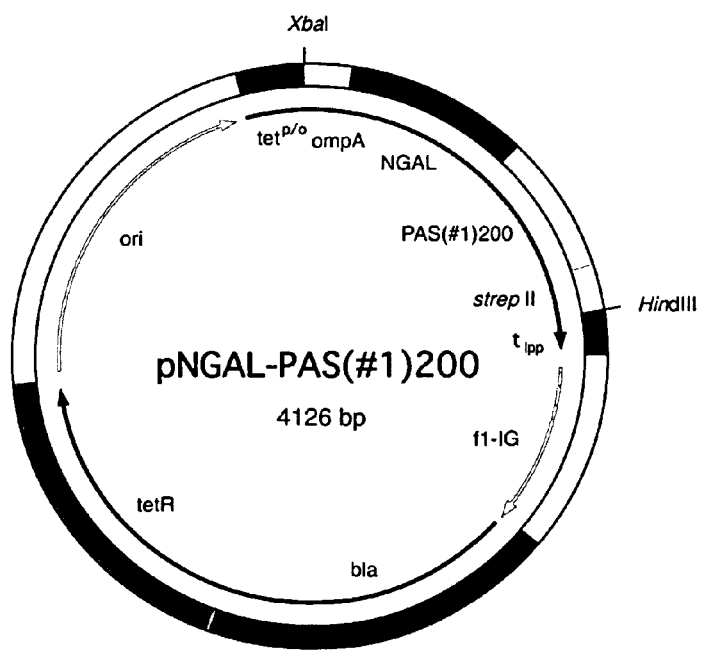

Figure 4:
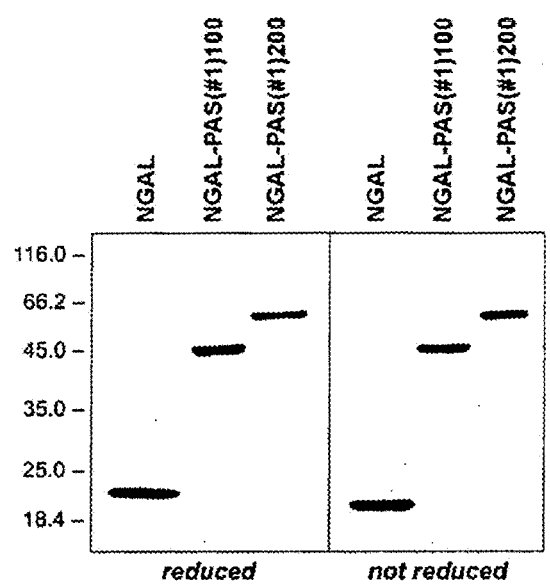

Figure 4
A
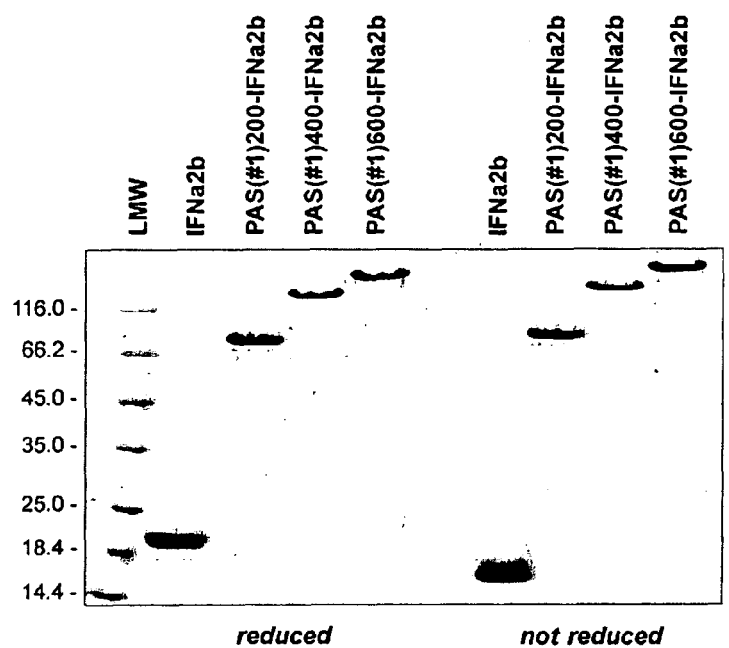
B
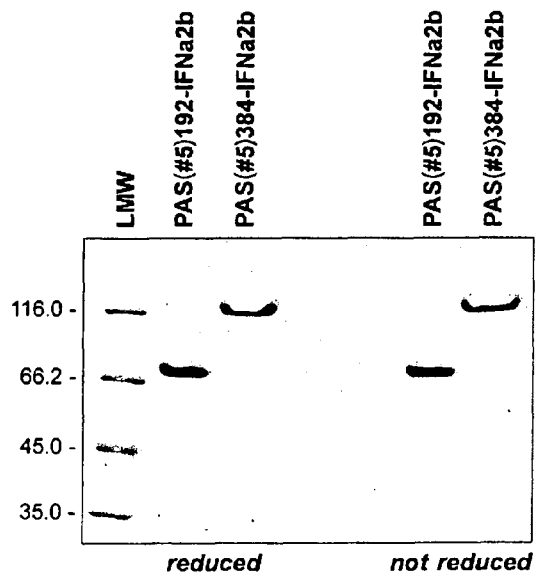

Figure 4 Continued...
C
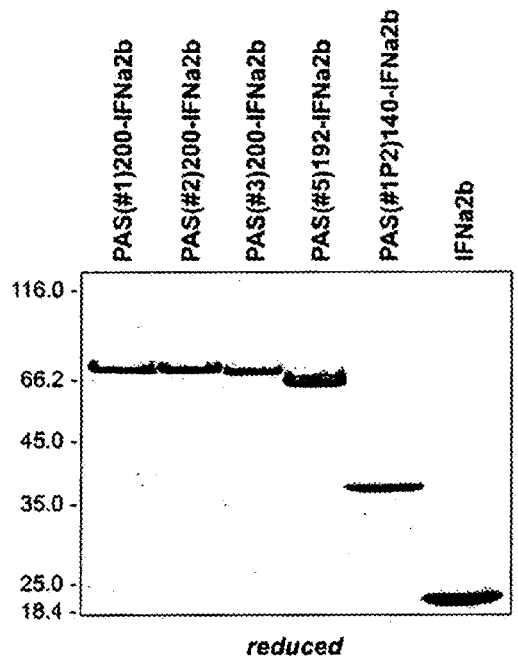
D
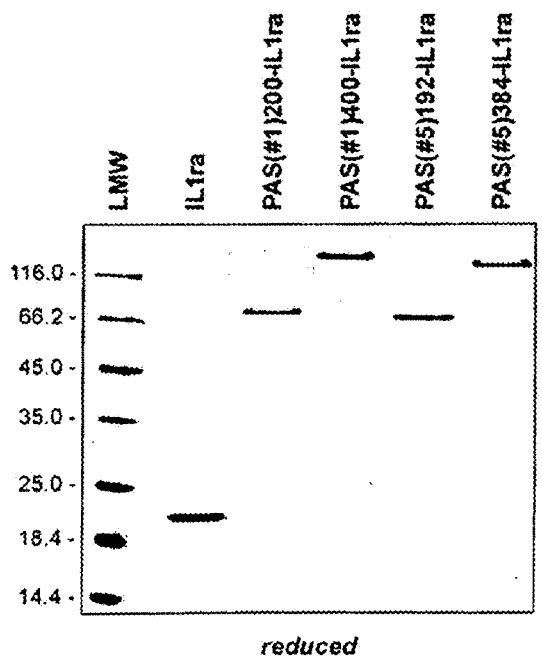

E

A

B

Figure 5:
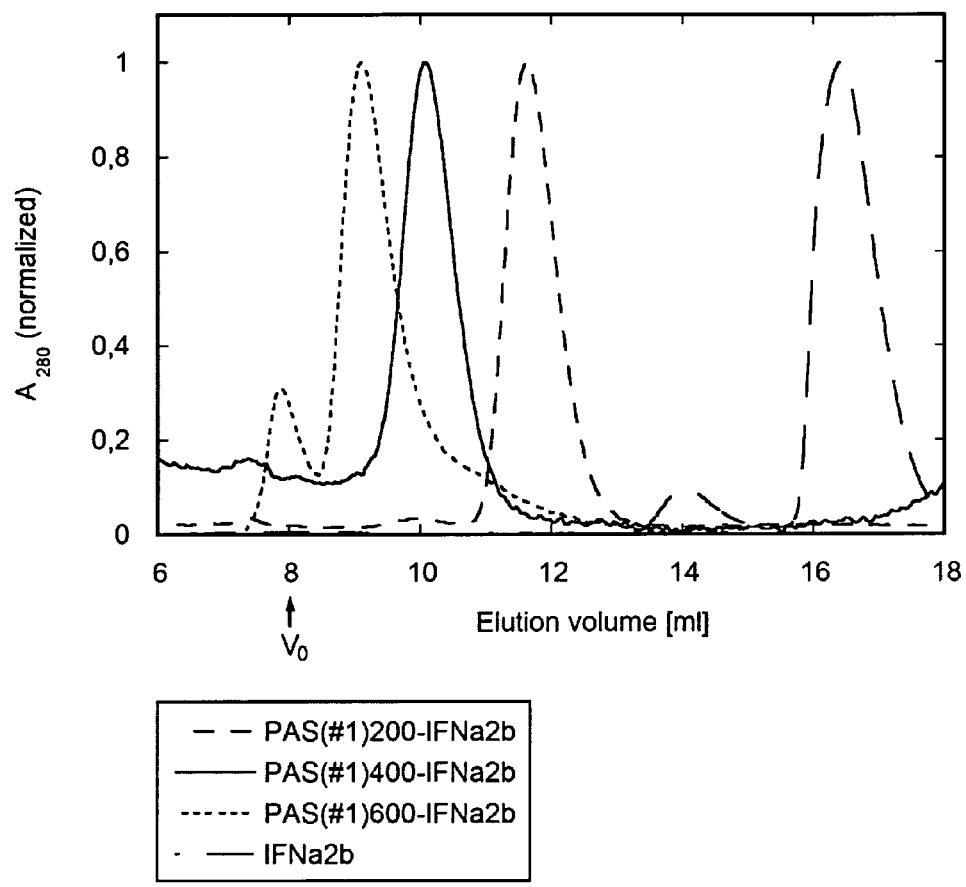
Figure 5:
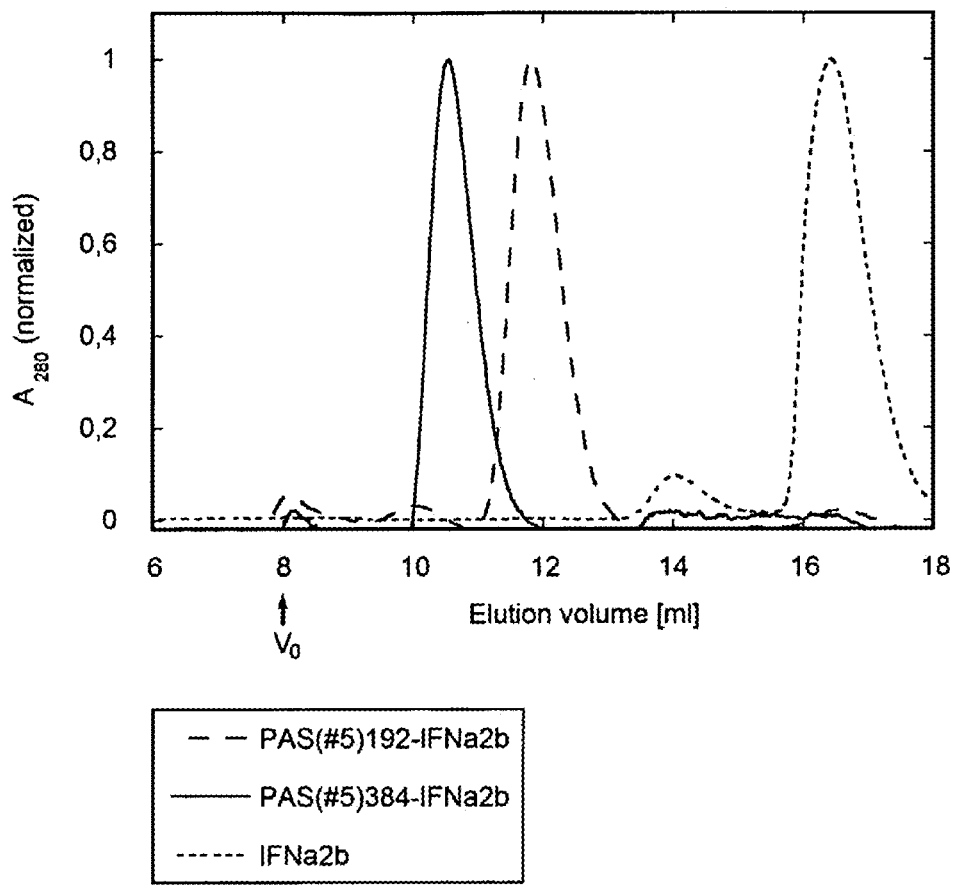
Figure 5:
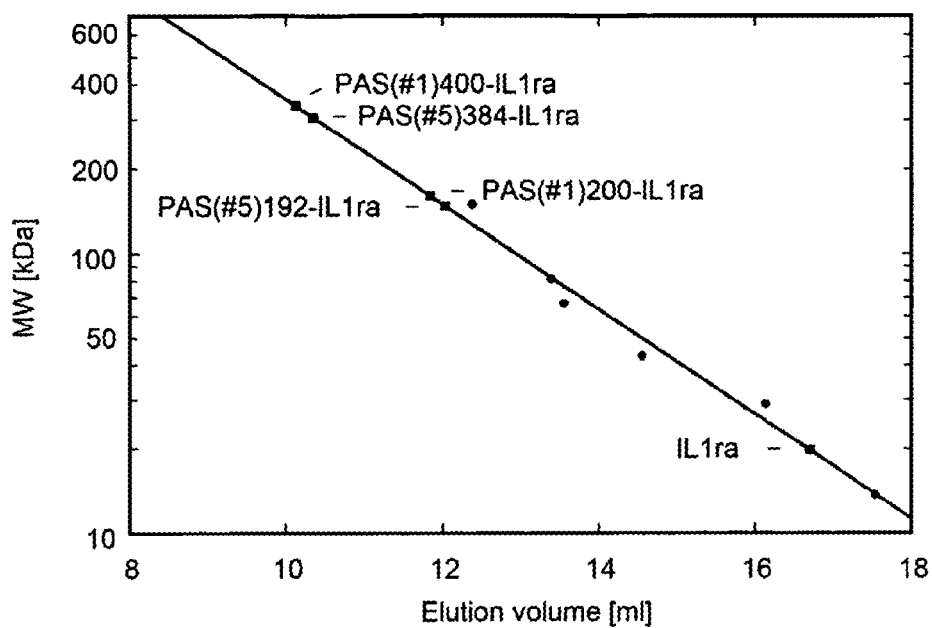

Figure 5 Continued...
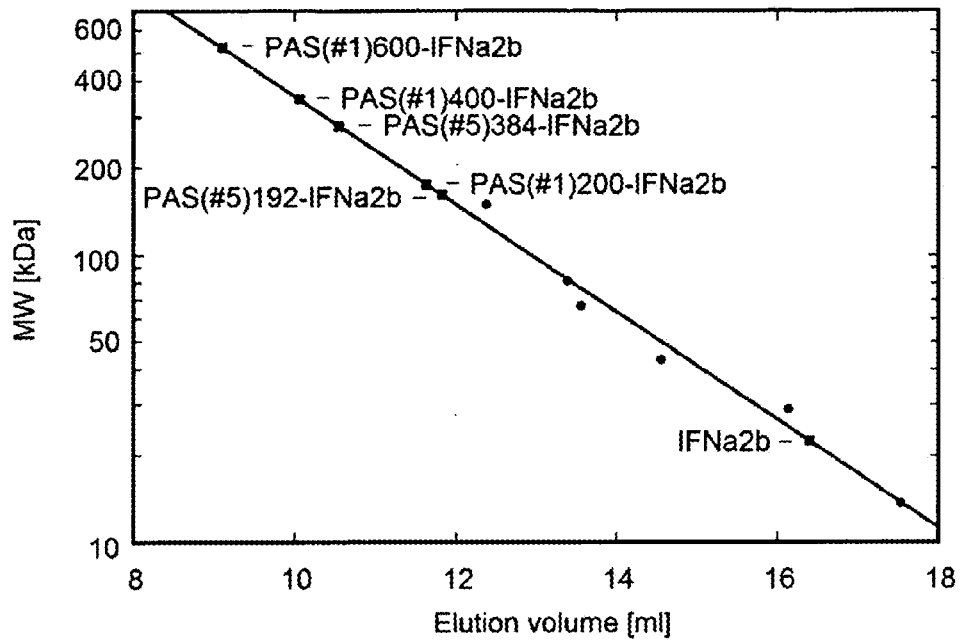
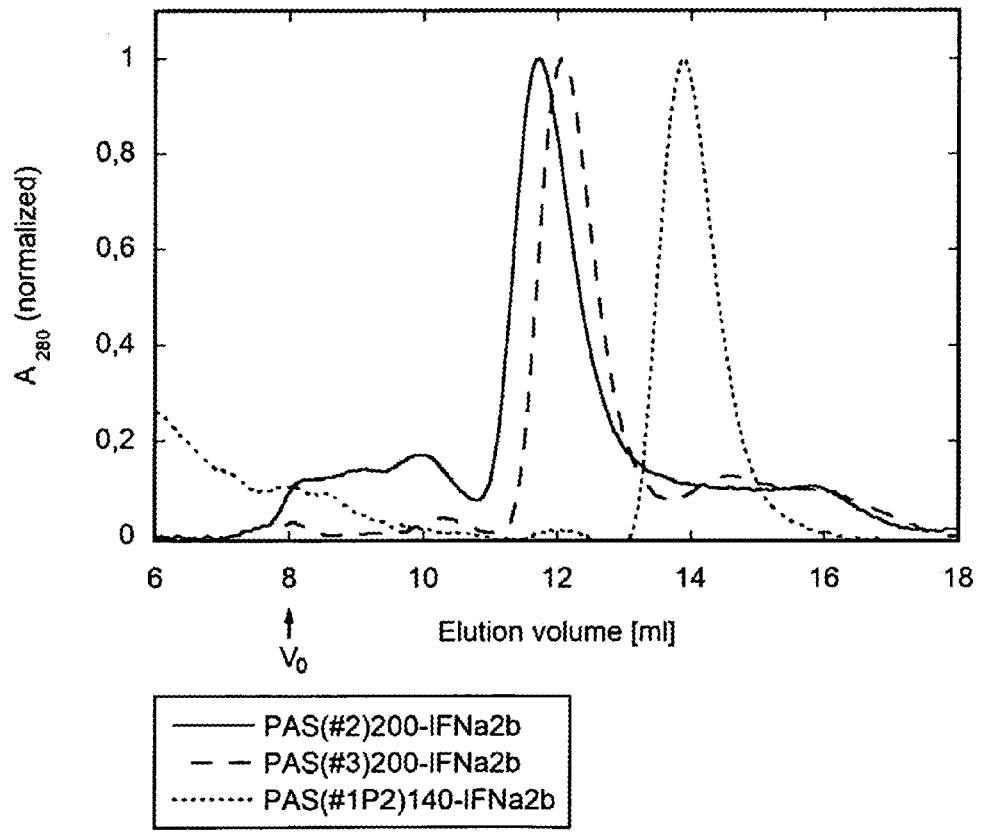

Figure 5 Continued...
E
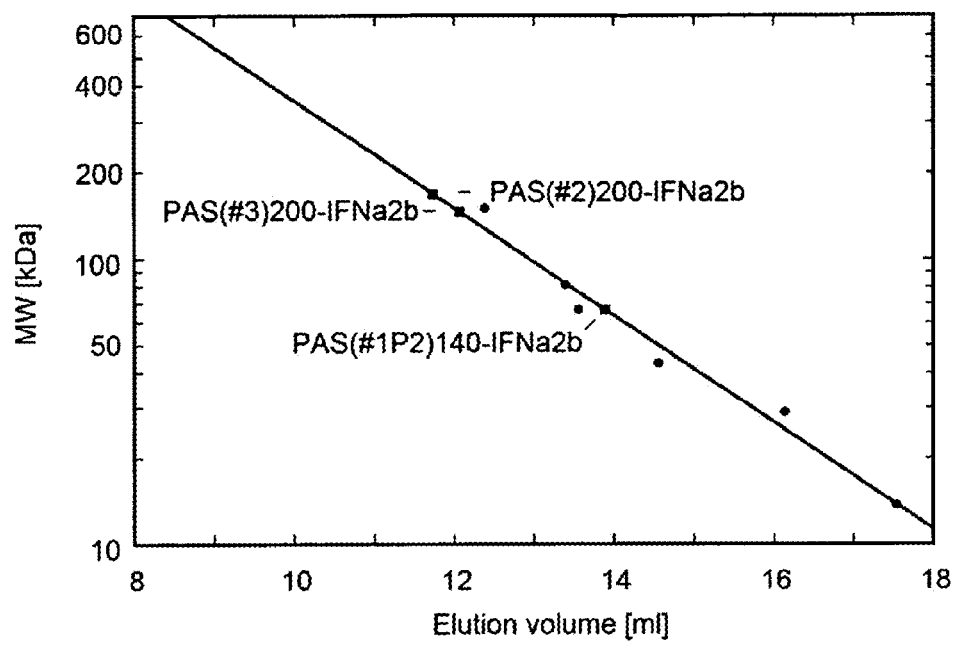
F
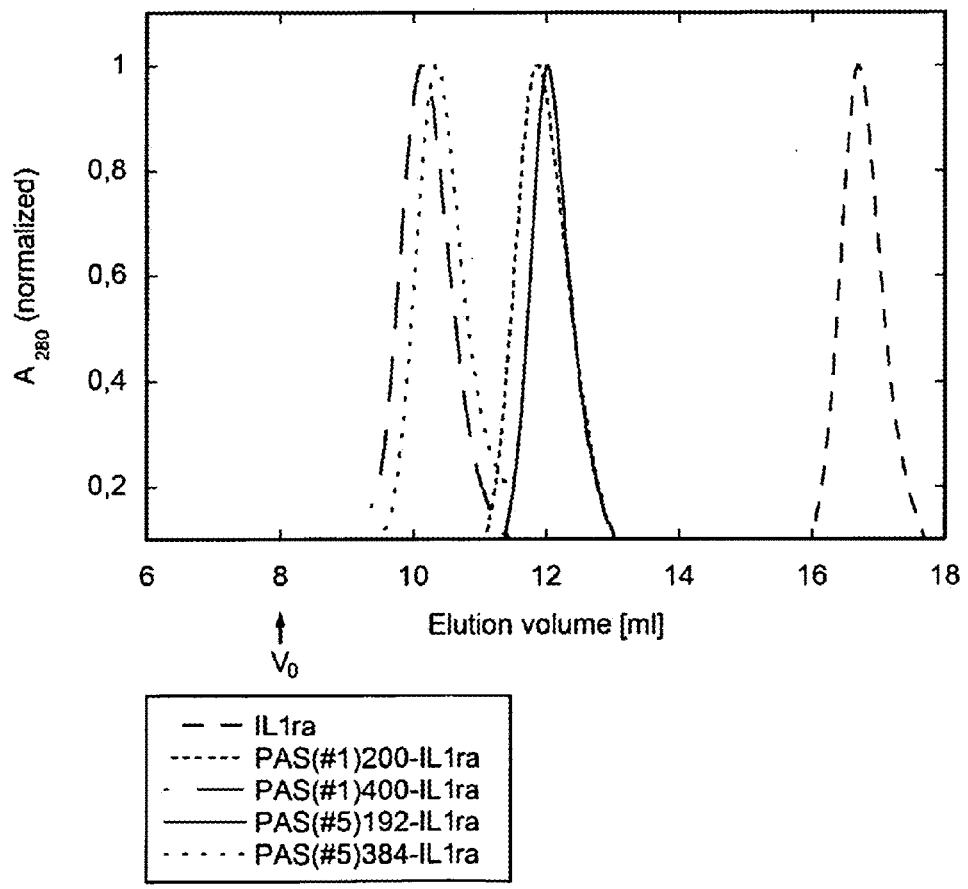

G

Figure 5 Continued...
H
Superdex S75:
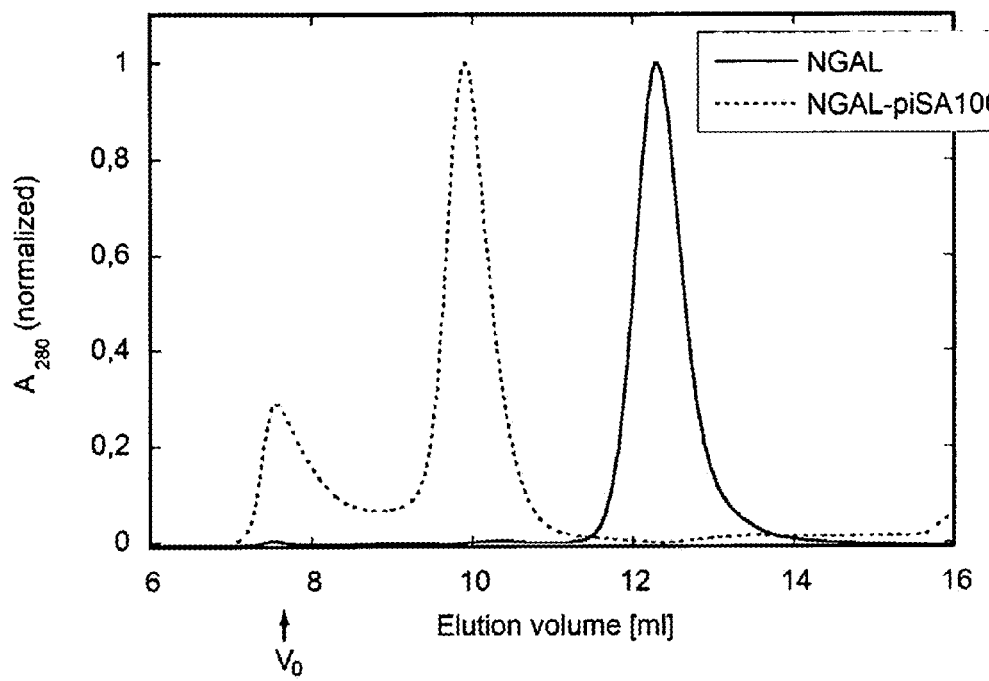
Superdex S200:
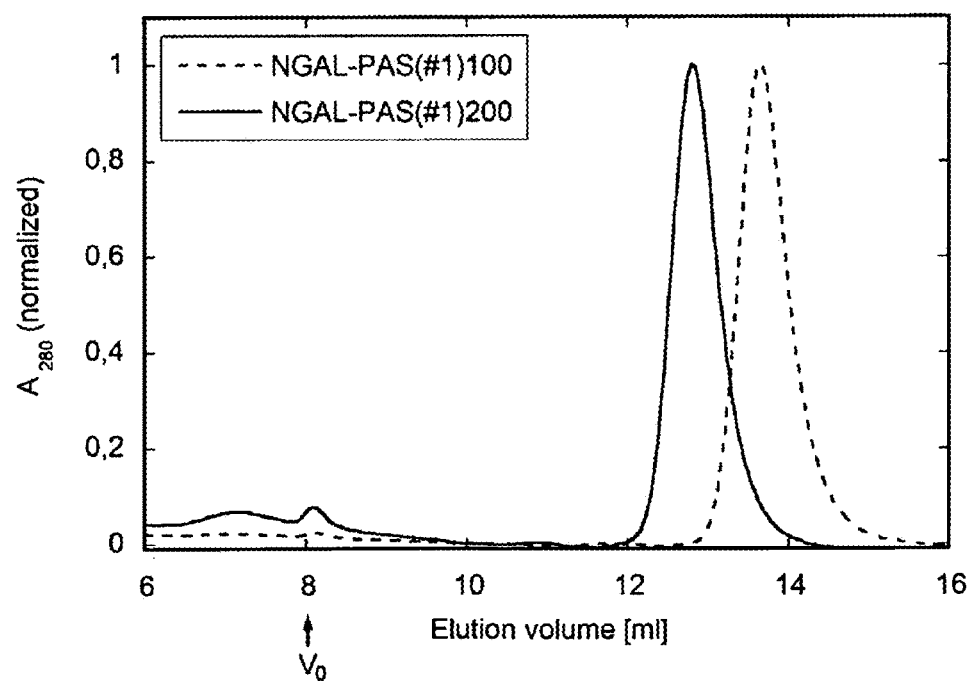

Figure 5 Continued...
Superdex S75:
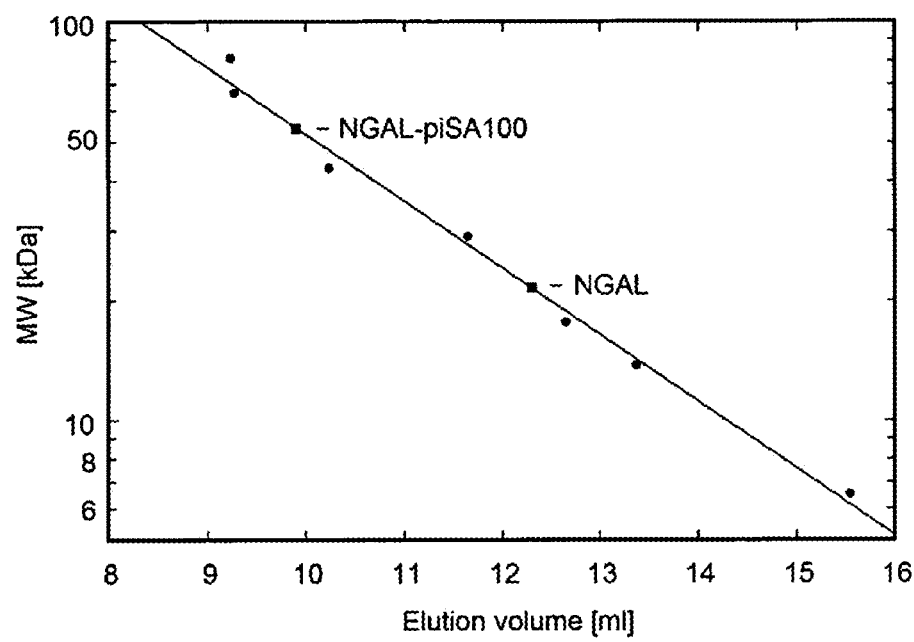
Superdex S200:
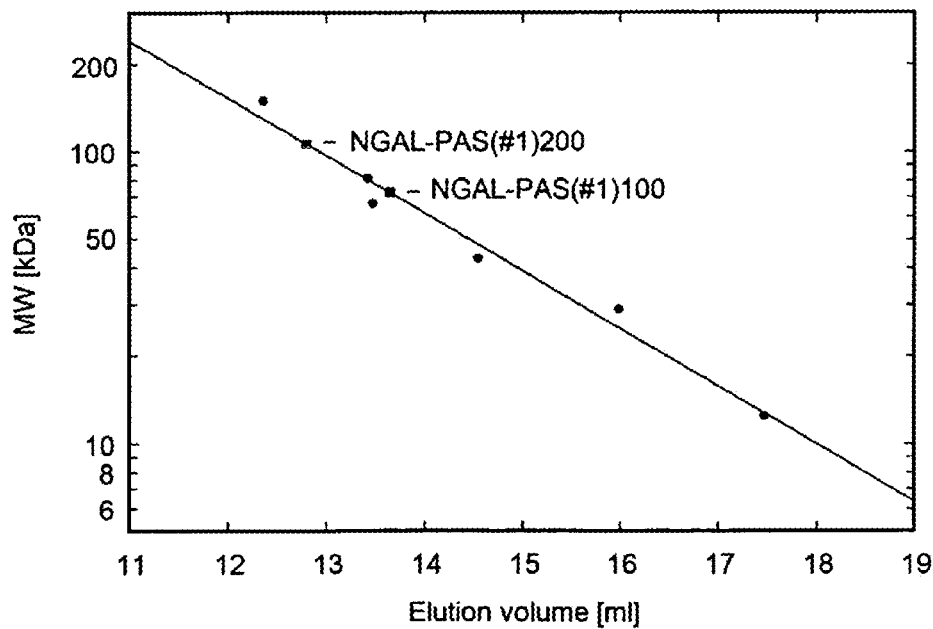

Figure 6:
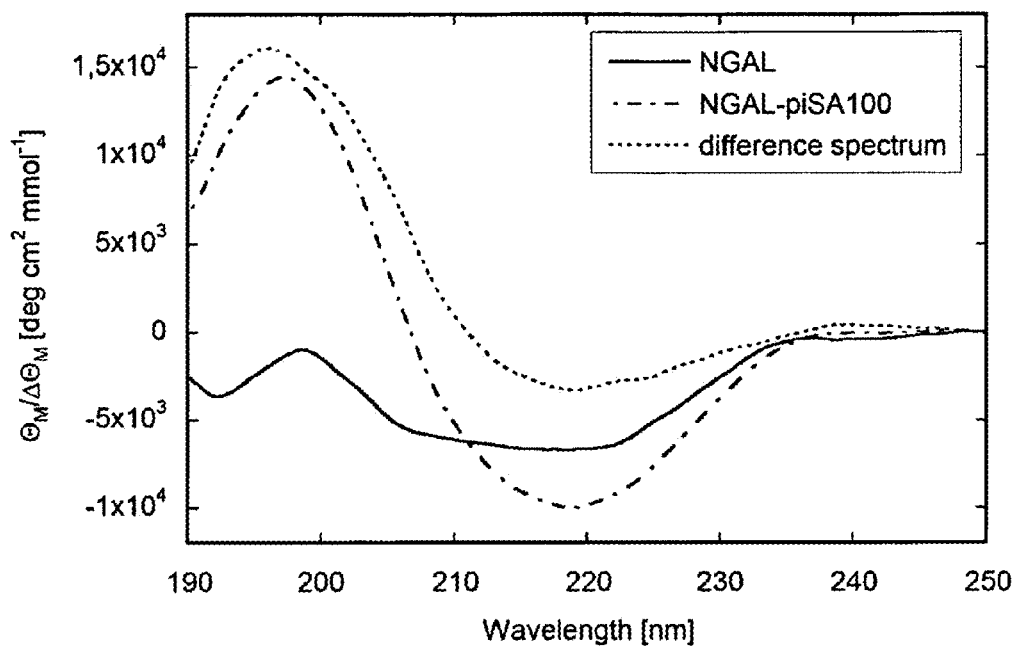

Figure 6
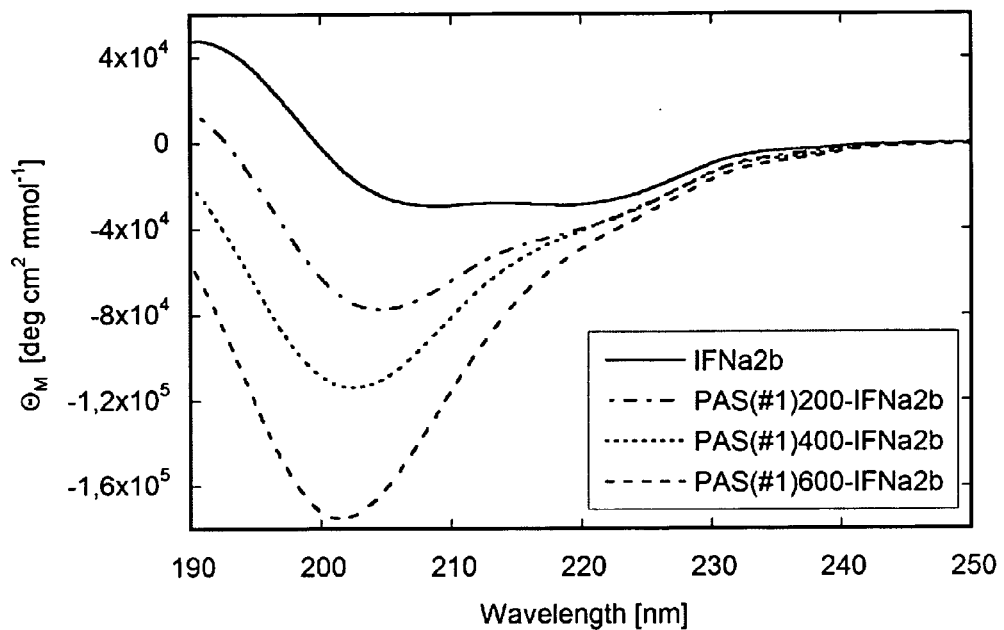
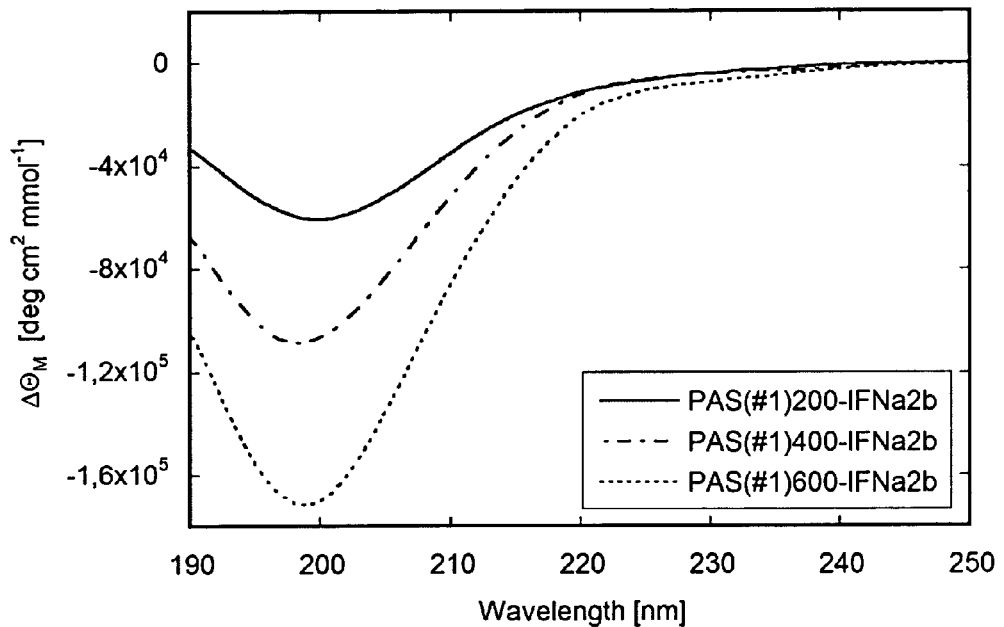

Figure 6 Continued...
C
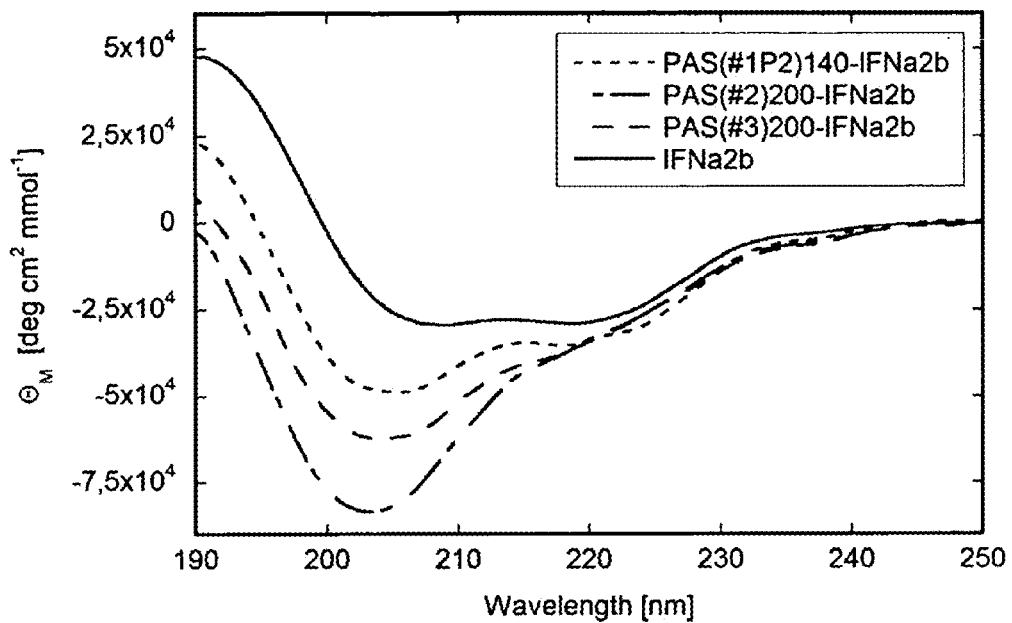
D
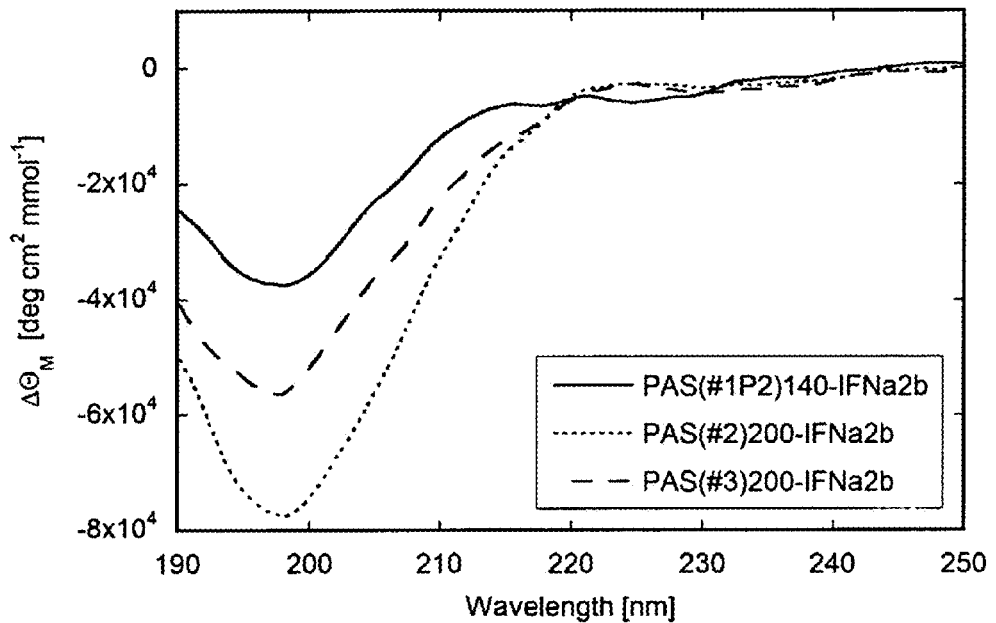

Figure 6 Continued...
E
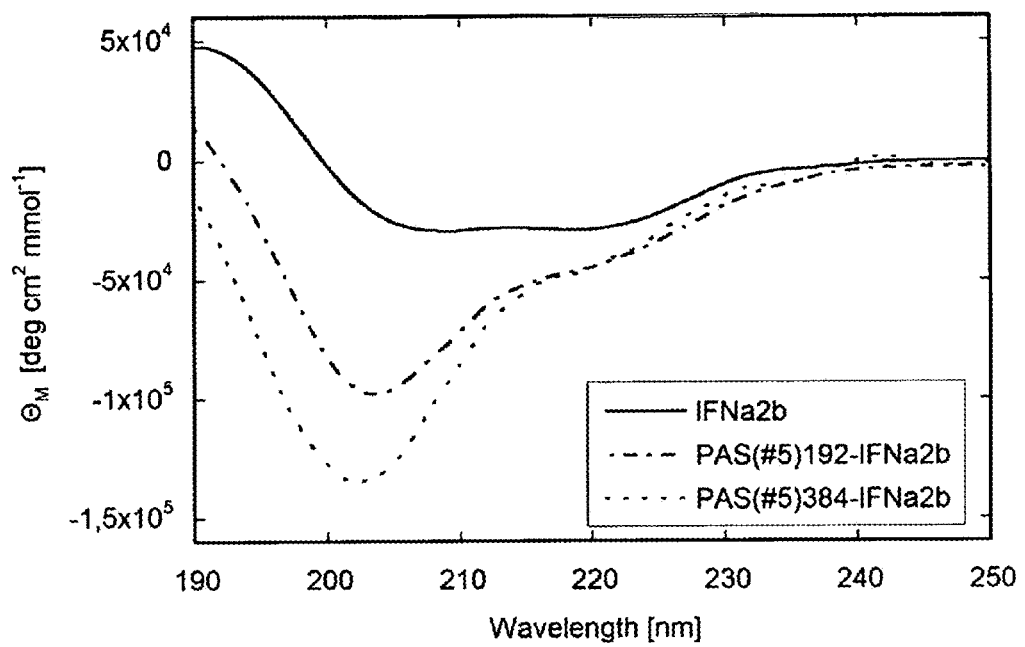
F
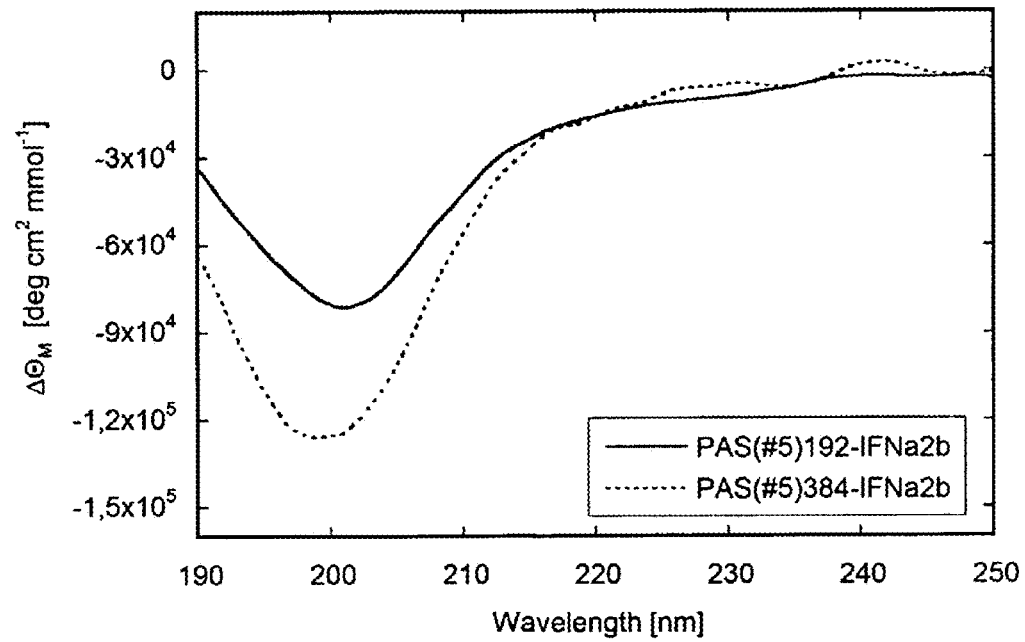

Figure 6 Continued...
G
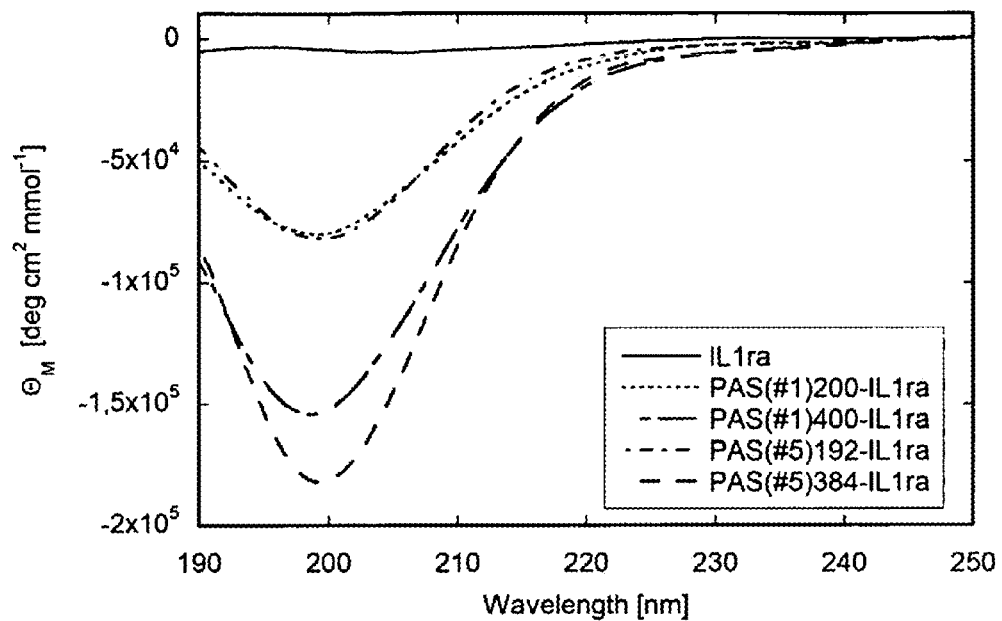
H
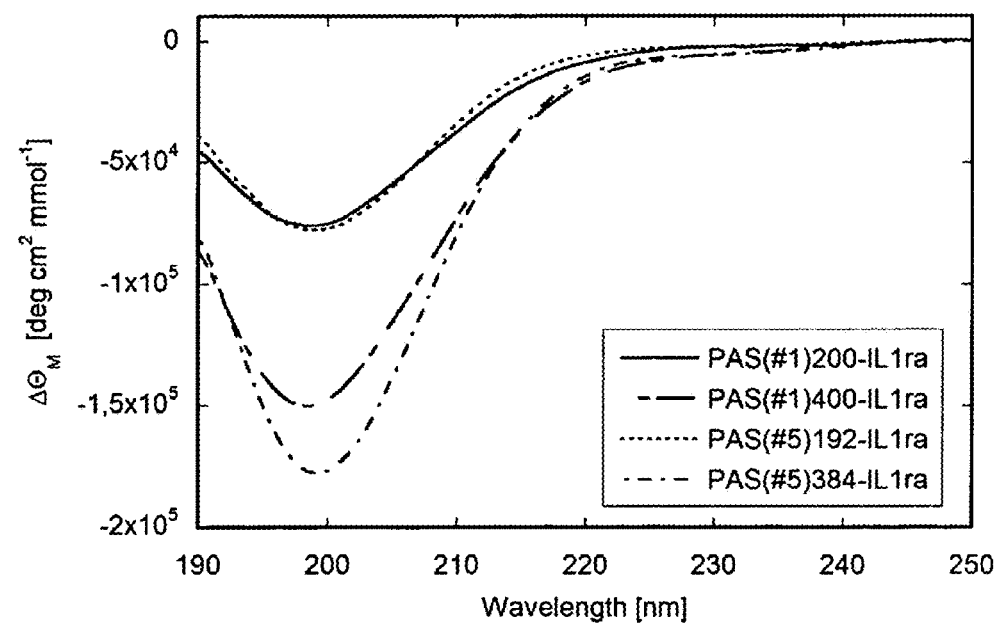

Figure 6 Continued...
I
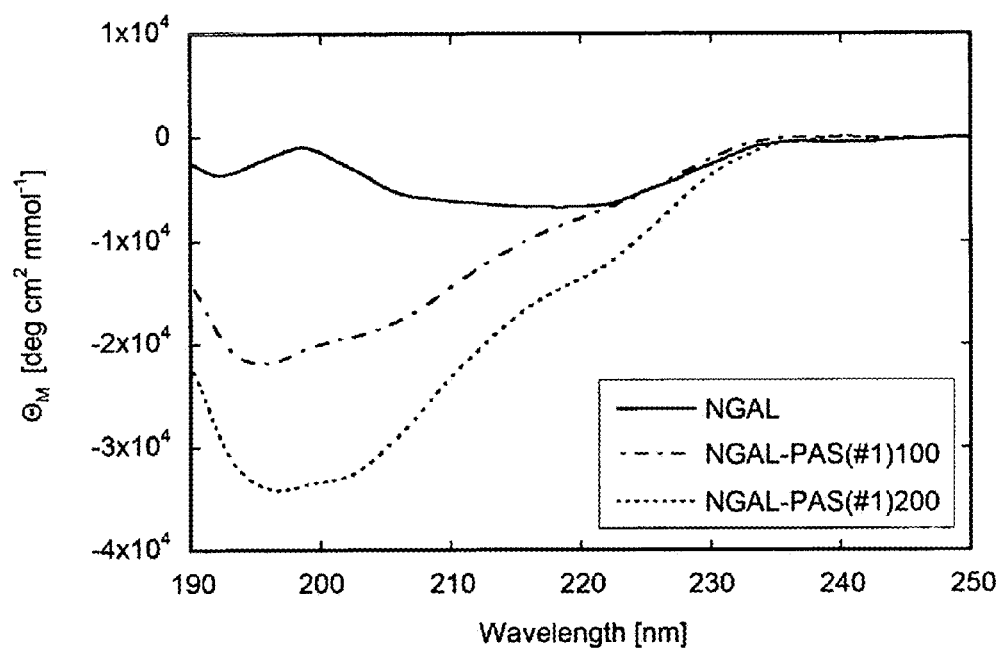
J
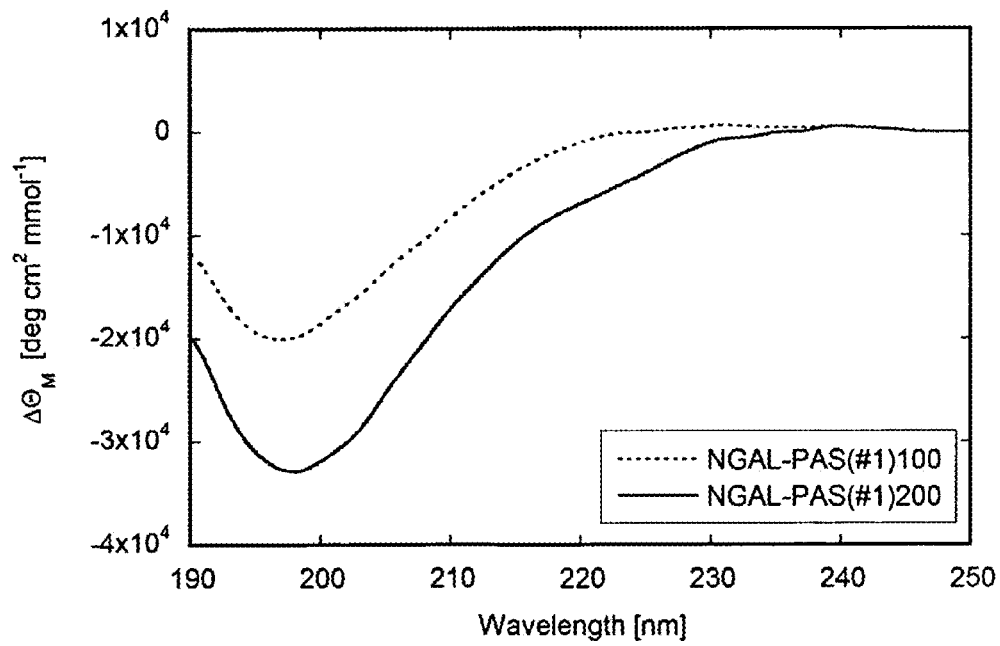

K

Figure 7
A
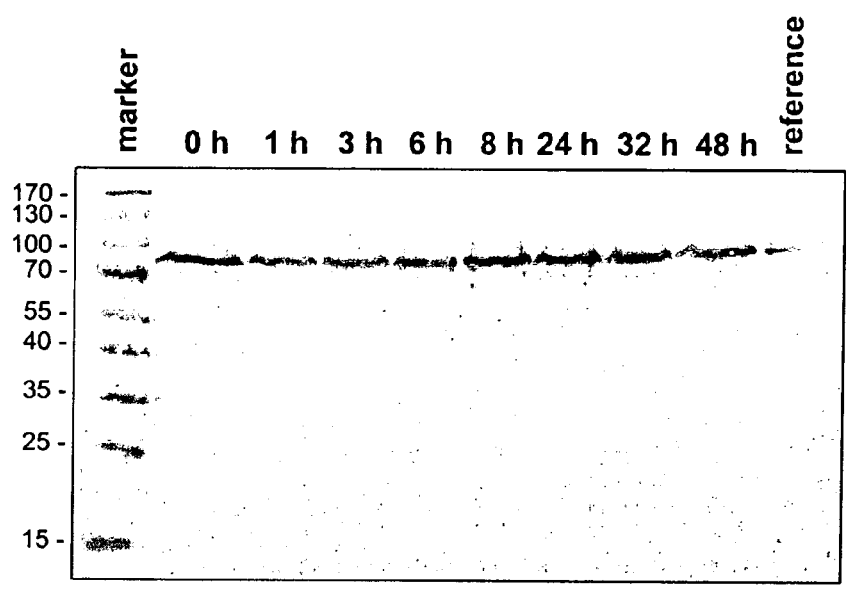
B
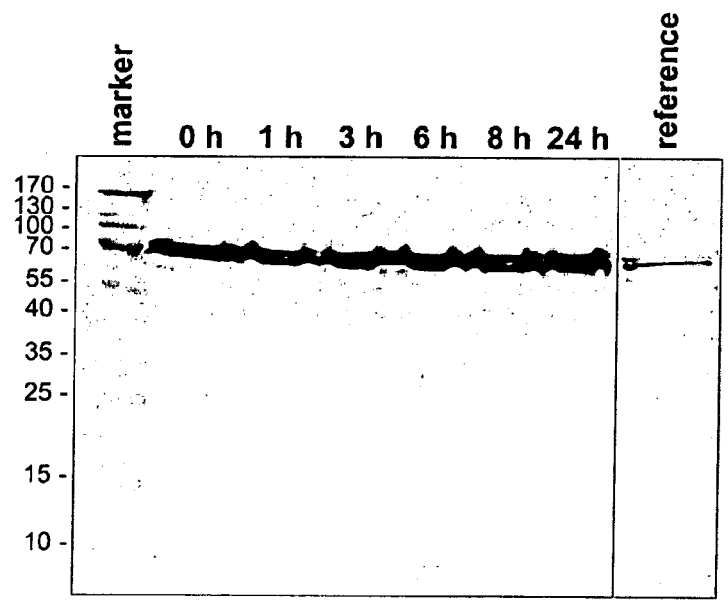

Figure 11
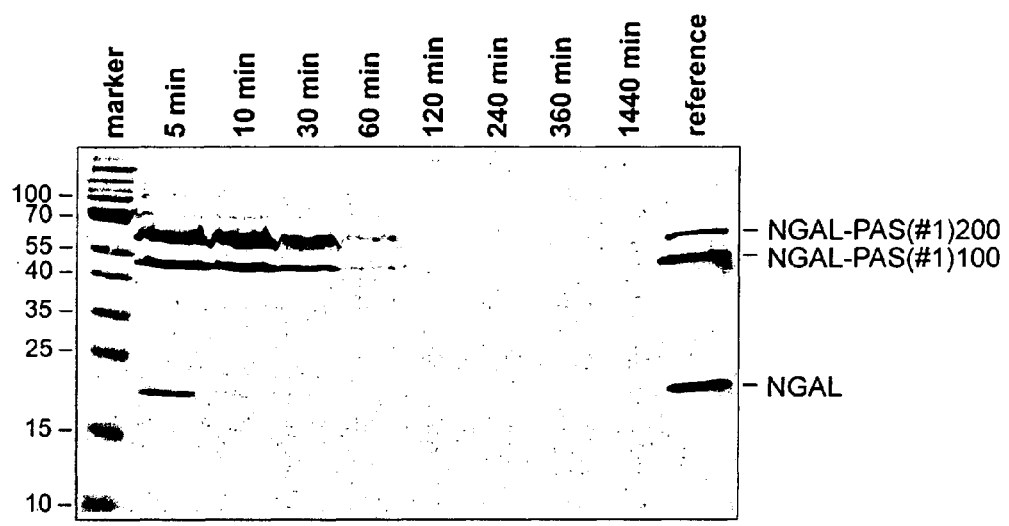
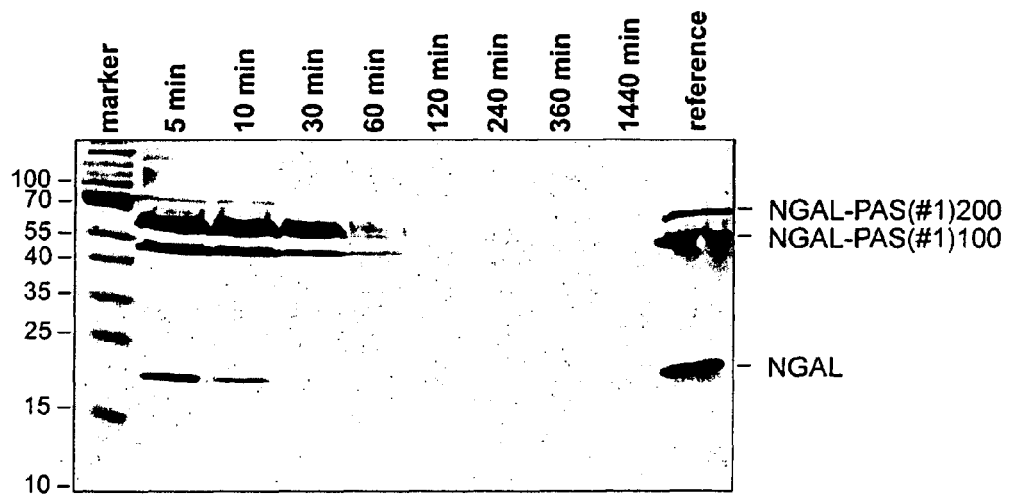

| | |
|---|---|
| 1: | unstimulatet cells |
| 2: | IntronA 3850 ng/ml |
| 3: | IntronA 38.5 ng/ml |
| 4: | IntronA 0.385 ng/ml |
| 5: | PAS(#1)200-IFNa2b 3850 ng/ml |
| 6: | PAS(#1)200-IFNa2b 38.5 ng/ml |
| 7: | PAS(#1)200-IFNa2b 0.385 ng/ml |
| 8: | Fab (negative control) 3850 ng/ml |
| 9: | Fab (negative control) 38.5 ng/ml |
| 10: | Fab (negative control) 0.385 ng/ml |

Figure 14 piSA:

Chou-Fasman plot of @, 60 aa;
QUERY

```
        AAAASSASSASSSSSAAASA|AAAASSASSASSSSSAAASA|AAAASSASSASSSSSAAASA
helix <------------------------------------------------------------>
sheet
turns            T T                    T T                    T T Residue totals: H: 59    E:  0    T:  6
       percent: H: 98.3  E:  0.0  T: 10.0
```

PAS#1:

Chou-Fasman plot of @, 60 aa;
QUERY

```
        ASPAAPAPASPAAPAPSAPA|ASPAAPAPASPAAPAPSAPA|ASPAAPAPASPAAPAPSAPA
helix    <----->          <---------->           <---------->
sheet
turns   T Residue totals: H: 31    E:  0    T:  1
       percent: H: 51.7  E:  0.0  T:  1.7
```

PAS#5:

Chou-Fasman plot of @, 72 aa;
QUERY

```
        AASPAAPSAPPAAASPAAPSAPPA|AASPAAPSAPPAAASPAAPSAPPA|AASPAAPSAPPA
helix <---->  <--------->  <-------->  <-------->  <-------->  <---
sheet
turns AASPAAPSAPPA
helix ----->
sheet
turns                T Residue totals: H: 56    E:  0    T:  1
       percent: H: 77.8  E:  0.0  T:  1.4
```

BIOLOGICAL ACTIVE PROTEINS HAVING INCREASED IN VIVO AND/OR IN VITRO STABILITY

The present invention relates to biologically active proteins comprising at least two domains wherein a first domain of said at least two domains comprises an amino acid sequence having and/or mediating said biological activity and a second domain of said at least two domains comprises an amino acid sequence consisting preferably of at least about 100 amino acid residues forming a random coil conformation whereby said random coil conformation mediates an increased in vivo and/or in vitro stability of said biologically active protein. Furthermore, nucleic acid molecules encoding the inventive biologically active proteins and vectors and cells comprising said nucleic acid molecules are disclosed. In addition, the present invention provides for compositions comprising the compounds of the invention as well as for specific uses of the biologically active proteins, nucleic acid molecules, vectors and cells of the invention.

Common plasma proteins such as human serum albumin (HSA) and immunoglobulins (Igs), including humanized antibodies, show long half-lifes, typically of 2 to 3 weeks, which is attributable to their specific interaction with the neonatal Fc receptor (FcRn), which leads to endosomal recycling (Ghetie (2002) Immunol Res, 25:97-113). In contrast, most other proteins of pharmaceutical interest, in particular recombinant antibody fragments, hormones, interferons, etc. suffer from rapid (blood) clearance. This is particularly true for proteins whose size is below the threshold value for kidney filtration of about 70 kDa (Caliceti (2003) Adv Drug Deliv Rev 55:1261-1277). In these cases the plasma half-life of an unmodified pharmaceutical protein may be considerably less than an hour, thus rendering it essentially useless for most therapeutic applications. In order to achieve sustained pharmacological action and also improved patient compliance—with required dosing intervals extending to several days or even weeks—several strategies were previously established for purposes of biopharmaceutical drug development.

First, the recycling mechanism of natural plasma proteins has been employed by producing fusion proteins with the Fc portion of Igs, for example Enbrel®, a hybrid between the extracellular domain of TNFα receptor and human IgG1 (Goldenberg (1999) Clin Ther 21:75-87) or with serum albumin, for example Albuferon®, a corresponding fusion of IFNα with HSA (Osborn (2002) J Pharmacol Exp Ther 303: 540-548). Albumin with its high plasma concentration of 600 μM has also been utilized in an indirect manner, serving as carrier vehicle for biopharmaceuticals that are equipped with an albumin-binding function, for example via fusion with a bacterial albumin-binding domain (ABD) from Streptococcal protein G (Makrides (1996) J Pharmacol Exp Ther 277:534-542) or with a peptide selected against HSA from a phage display library (Dennis (2002) J Biol Chem, 277:35035-35043; Nguyen (2006) Protein Eng Des Sel 19:291-297).

Second, a fundamentally different methodology for prolonging the plasma half-life of biopharmaceuticals is the conjugation with highly solvated and physiologically inert chemical polymers, thus effectively enlarging the hydrodynamic radius of the therapeutic protein beyond the glomerular pore size of approximately 3-5 nm (Caliceti (2003) loc. cit.). Covalent coupling under biochemically mild conditions with activated derivatives of poly-ethylene glycol (PEG), either randomly via Lys side chains (Clark (1996) J Biol Chem 271:21969-21977) or by means of specifically introduced Cys residues (Rosendahl (2005) BioProcess International: 52-60) has been moderately successful and is currently being applied in several approved drugs. Corresponding advantages have been achieved especially in conjunction with small proteins possessing specific pharmacological activity, for example Pegasys®, a chemically PEGylated recombinant IFN-α-2a (Harris (2003) Nat Rev Drug Discov, 2:214-221; Walsh (2003) Nat Biotechnol 21:865-870).

However, the chemical coupling of a biologically active protein with synthetic polymers may have disadvantages with respect to biopharmaceutical development and production. Suitable PEG derivatives are expensive, especially as high purity is needed, and their conjugation with a recombinant protein requires additional in vitro processing and purification steps, which lower the yield and raise the manufacturing costs. In fact, PEG is often contaminated with aldehydes and peroxides (Ray (1985) Anal Biochem 146:307-312) and it is intrinsically prone to chemical degradation upon storage in the presence of oxygen. Also, the pharmaceutical function of a therapeutic protein may be hampered if amino acid side chains in the vicinity of its biochemical active site become modified by the PEGylation process. Furthermore, chemical coupling with synthetic polymers usually results in a heterogeneous mixture of molecules which may show a substantial variance of the in vivo activity.

Third, the use of glycosylation analogs of biologically active proteins in which new N-linked glycosylation consensus sequences are introduced has been proposed to prolong serum half-life; see WO 02/02597; Perlman (2003) J Clin Endocrinol Metab 88:2327-2335; or Elliott (2003) Nat Biotechnol 21:414-420). The described glycoengineered proteins, however, displayed an altered in vivo activity, which indicates that the new carbohydrate side chains influence the biological activity of the engineered protein. Moreover, the additional carbohydrate side chains are likely to increase the antigenicity of the resulting biological active molecules, which raises substantial safety concerns.

Furthermore, fusion proteins comprising the *Trypanosoma cruzi* derived artificial repetitive sequence PSTAD have been reported to induce a prolonged plasma half-life of trans-sialidase (Alvarez (2004) JBC 279:3375-3381). Yet, such *Trypanosoma cruzi* derived repeats have been reported to induce a humoral immune response (Alvarez (2004) loc. cit.). Accordingly, alternative means to prolong the action of biologically active proteins are desired The technical problem underlying the present invention is the provision of biologically active proteins with an increased in vivo and/or in vitro stability. The solution to the above technical problem is achieved by providing the embodiments characterized in the claims.

Accordingly, this invention relates to a biologically active protein comprising at least two domains wherein
 (a) a first domain of said at least two domains comprises an amino acid sequence having and/or mediating said biological activity; and
 (b) a second domain of said at least two domains comprises an amino acid sequence consisting preferably of at least about 100 amino acid residues forming random coil conformation.

In accordance with this invention, said second domain forming/adopting random coil conformation is capable of mediating an increased in vivo and/or in vitro stability of said biologically active protein. Said second domain, therefore, leads to an increased in vivo and/or in vitro stability of a given protein (or a fragment thereof) having a/or mediating a given biological activity, as defined herein below.

As documented herein below and in the appended examples it was surprisingly found that intravenously administered biologically active proteins which are modified to comprise a random coil domain/part display an unexpected prolonged plasma half-life when compared to the unmodified biologically active proteins, i.e. which lacks said random coil domain.

As used herein, the term "random coil" relates to any conformation of a polymeric molecule, including amino acid polymers, in which the individual monomeric elements that form said polymeric structure are essentially randomly oriented towards the adjacent monomeric elements while still being chemically bound to said adjacent monomeric elements. In particular, a polypeptide or amino acid polymer adopting/having/forming "random coil conformation" substantially lacks a defined secondary and tertiary structure. The nature of polypeptide random coils and their methods of experimental identification are known to the person skilled in the art and have been described in the scientific literature (Cantor (1980) Biophysical Chemistry, 2nd ed., W. H. Freeman and Company, New York; Creighton (1993) Proteins—Structures and Molecular Properties, 2nd ed., W. H. Freeman and Company, New York; Smith (1996) Fold Des 1:R95-R106).

The biologically active proteins of the present invention comprise a domain (defined herein above as said "second domain" of the inventive biologically active protein) that adopts/forms random coil conformation at physiological conditions. The term "physiological conditions" is known in the art and relates to those conditions in which proteins usually adopt their native conformation. More specifically, the term "physiological conditions" relates to the biophysical parameters as they are typically valid for higher forms of life and, particularly, in mammals, most preferably human beings. The term "physiological conditions" may relate to the biochemical and biophysical parameters as they are normally found in the body (in particular in body fluids) of mammals and in particular in humans. Said "physiological conditions" may relate to the corresponding parameters found in the healthy body as well as the parameters as found in sick mammals or human patients. For example, a sick mammal or human patient may have a higher, yet "physiological" temperature condition when said mammal or said human suffers from fever. With respect to "physiological conditions/state" at which proteins adopt their native conformation/state, the most important parameters are temperature (37° C. for the human body), pH (7.35-7.45 for human blood), osmolarity (280-300 mmol/kg $H_2O$), and, if necessary, protein content (66-85 g/l serum). Yet, the person skilled in the art is aware that at physiological conditions these parameters may vary, e.g. the temperature, pH, osmolarity, and protein content may be different in given body or tissue fluids such as blood, liquor cerebrospinalis, peritoneal fluid and lymph (Klinke (2005) Physiologie, 5th ed., Georg Thieme Verlag, Stuttgart). In the liquor cerebrospinalis, e.g. the osmolarity may be around 290 mmol/kg $H_2O$ and the protein concentration may be between 0.15 g/l to 0.45 g/l. In the lymph, the pH may be around 7.4 and the protein content may be between 3 g/l and 5 g/l.

When determining whether an amino acid polymer/sequence forms/adopts random coil conformation under experimental conditions using the methods as described herein below, the biophysical parameters such as temperature, pH, osmolarity and protein content may be different to the physiological conditions normally found in vivo. Temperatures between 1° C. and 42° C. or preferably 4° C. to 25° C. may be considered useful to test and/or verify the biophysical properties and biological activity of a protein under physiological conditions in vitro.

Several buffers, in particular in experimental settings (for example in the determination of protein structures, in particular in circular dichroism (CD) measurements and other methods that allow the person skilled in the art to determine the structural properties of a protein/amino acid stretch) or in buffers, solvents and/or excipients for pharmaceutical compositions, are considered to represent "physiological solutions"/"physiological conditions" in vitro. Examples of such buffers are, e.g. phosphate-buffered saline (PBS: 115 mM NaCl, 4 mM $KH_2PO_4$, 16 mM $Na_2HPO_4$ pH 7.4), Tris buffers, acetate buffers, citrate buffers or similar buffers such as those used in the appended examples. Generally, the pH of a buffer representing "physiological solution conditions" should lie in a range from 6.5 to 8.5, preferably in a range from 7.0 to 8.0, most preferably in a range from 7.2 to 7.7 and the osmolarity should lie in a range from 10 to 1000 mmol/kg $H_2O$, more preferably in a range from 50 to 500 mmol/kg $H_2O$ and most preferably in a range from 200 to 350 mmol/kg $H_2O$. Optionally, the protein content of a buffer representing physiological solution conditions may lie in a range from 0 to 100 g/l, neglecting the protein with biological activity itself, whereby typical stabilizing proteins may be used, for example human or bovine serum albumin.

Accordingly, it is also envisaged in context of this invention that the random coil conformation as comprised in the above defined "second domain" of the inventive biologically active protein is maintained in pharmaceutical compositions, like liquid pharmaceuticals. Preferably, "physiological conditions" are to be used in corresponding buffer systems, solvents and/or excipients. Yet, for example in lyophilized or dried compositions (like, e.g. pharmaceutical compositions), it is envisaged that the random coil conformation as comprised in the "second domain" of the inventive biologically active protein is transiently not present and/or can not be detected. However, said "second domain" will, in accordance with the present inventive protein constructs, adopt/form again its random coil after reconstitution in corresponding buffers/solutions/excipients/solvents. This is for example the case where the inventive protein constructs had been lyophilized or dried (e.g. in form of a pharmaceutical composition). After reconstitution of such a lyophilized/dried inventive protein construct comprising the "first" and "second" domain as defined herein, the random coil part/domain is again present and the corresponding inventive construct can be, e.g., administered to a mammal or human patient in need of medical intervention.

As mentioned above, the biologically active proteins of the present invention comprise a domain (defined herein above as said "second domain" of the inventive biologically active protein) that adopts/forms random coil conformation at/under physiological conditions.

In contrast to the biologically active proteins of this invention, denatured proteins are proteins that lost their functional conformation and may partially adopt random coil conformation as a result of said denaturation. Proteins can be denatured through various means including exposure to unphysiological temperature, pH and/or salt concentration or exposure to denaturing agents like urea/guanidinium chloride and detergents. Accordingly, the presence of compounds that are known to have a denaturing effect on proteins, such as urea, guanidinium chloride or sodium dodecyl sulphate, are to be avoided when studying a protein under physiological conditions. Urea may be tolerated up to concentrations of 10 mmol/l or even 300 mmol/l when investigating a protein for application under physiological conditions in human blood or urine, respectively.

In contrast to denatured polypeptides, the amino acid sequence of the random coil domain (said "second domain") as comprised in the inventive protein construct natively adopts/has random coil conformation, in particular in vivo and when administered to mammals or human patients in need of medical intervention. Accordingly, it is also envisaged that the protein construct of the present invention (comprising the above defined "first" and "second domain") may comprise the "second", random coil forming/adopting domain in form of the herein identified alanine, serine, and proline stretches (or other amino acid stretches that form/have/adopt random coil under physiological conditions), but may be (for example, in form of a specific composition, like a lyophylisate or dried composition) transiently or temporarily not in random coil form. Yet, it is important that such a "second domain" of the inventive protein construct again adopts after, e.g., reconstitution in corresponding buffers (preferably "physiological" buffers/excipients and/or solvents), the herein defined random coil. Said "second domain" is, (after a corresponding reconstitution) capable of mediating an increased in vivo and/or in vitro stability of the inventive biologically active protein. The biologically active protein of this invention has a longer in vivo and/or in vitro half-life and stability in comparison to the same "protein of interest"/"first domain" that does not comprise the additional "second domain" as defined herein.

As used herein, the term "domain" relates to any region/part of an amino acid sequence that is capable of autonomously adopting a specific structure and/or function. In the context of the present invention, accordingly, a "domain" may represent a functional domain or a structural domain. As described herein, the proteins of the present invention comprise at least one domain/part having and/or mediating biological activity and at least one domain/part forming random coil conformation. Yet, the proteins of the invention also may consist of more than two domains and may comprise e.g. an additional linker structure between the herein defined two domains/parts or another domain/part like, e.g. a protease sensitive cleavage site, an affinity tag such as the $His_6$-tag or the Strep-tag, a signal peptide, retention peptide, a targeting peptide like a membrane translocation peptide or additional effector domains like antibody fragments for tumour targeting associated with an anti-tumour toxin or an enzyme for prodrug-activation etc.

Methods for determining whether an amino acid polymer forms/adopts random coil conformation are known in the art (Cantor (1980) loc. cit.; Creighton (1993) loc. cit.; Smith (1996) loc. cit.). Such methods include circular dichroism (CD) spectroscopy as exemplified herein below. CD spectroscopy represents a light absorption spectroscopy method in which the difference in absorbance of right- and left-circularly polarized light by a substance is measured. The secondary structure of a protein can be determined by CD spectroscopy using far-ultraviolet spectra with a wavelength between approximately 190 and 250 nm. At these wavelengths, the different secondary structures commonly found in polypeptides can be analyzed, since α-helix, parallel and anti-parallel β-sheet and random coil conformations each give rise to a characteristic shape and magnitude of the CD spectrum. Accordingly, by using CD spectrometry the skilled artisan is readily capable of determining whether an amino acid polymer forms/adopts random coil conformation at physiological conditions. Other established biophysical methods include nuclear magnetic resonance (NMR) spectroscopy, absorption spectrometry, infrared and Raman spectrometry, measurement of the hydrodynamic volume via size exclusion chromatography, analytical ultracentrifugation or dynamic/static light scattering as well as measurements of the frictional coefficient or intrinsic viscosity (Cantor (1980) loc. cit.; Creighton (1993) loc. cit.; Smith (1996) loc. cit.).

In another embodiment, the biologically active protein of the invention has a hydrodynamic volume as determined by analytical gel filtration (also known as size exclusion chromatography, SEC) of at least 70 kDa, preferably of at least 80 kDa, more preferably of at least 90 kDa, even more preferably of at least 100 kDa, particularly preferably of at least 125 kDa and most preferably of at least 150 kDa. The person skilled in the art is readily capable of determining the hydrodynamic volume of specific proteins. Such methods may include dynamic/static light scattering, analytical ultracentrifugation or analytical gel filtration as exemplified herein below. Analytical gel filtration represents a known method in the art for measuring the hydrodynamic volume of macromolecules. Alternatively, the hydrodynamic volume of a globular polypeptide can be estimated by its molecular weight. As described herein below, however, the hydrodynamic volume of the proteins of the invention that comprise the above defined second domain, i.e. the domain comprising at least 100 amino acid residues and having random coil conformation, are shown to have an unexpectedly high hydrodynamic volume in relation to the estimated hydrodynamic volume for a corresponding folded, globular protein based on their molecular weight.

In addition to the above, theoretical methods for the prediction of secondary structures in proteins have been described. One example of such a theoretical method is the Chou-Fasman method (Chou and Fasman (1974) Biochemistry 13:222-245) which is based on an analysis of the relative frequencies of each amino acid in α-helices, β-sheets, and turns based on known protein structures solved with X-ray crystallography. However, theoretical prediction of protein secondary structure is known to be unreliable. As exemplified herein below amino acid sequences expected to adopt an α-helical secondary structure according to the Chou-Fasman method were found to form a random coil. Accordingly, theoretical methods such as the Chou-Fasman algorithm only have very limited predictive value whether a given amino acid polymer adopts random coil conformation.

In one embodiment, the amino acid sequence adopting/having/forming random coil conformation consists of at least about 100 amino acid residues, preferably of at least about 150 amino acid residues, more preferably of at least about 200 amino acid residues, even more preferably of at least about 250 amino acid residues, particularly preferably of at least about 300 amino acid residues, more particularly preferably of at least about 350 amino acid residues and most preferably of at least about 400 amino acid residues. In another embodiment, the amino acid sequence forming random coil conformation consists of maximally about 1000 amino acid residues, preferably of maximally about 900 amino acid residues, more preferably of maximally about 800 amino acid residues, even more preferably of maximally about 700 amino acid residues, particularly preferably of maximally about 600 amino acid residues. Thus, the amino acid sequence forming random coil conformation may consist of maximally about 500 amino acid residues or of maximally about 450 amino acid residues. It is also envisaged herein that the amino acid sequence forming random coil conformation may consist of maximally about 1200, about 1500 and up to about 3000 amino acid residues. Accordingly, the amino acid sequence forming random coil conformation may consist of about 100 to about 3000 amino acid residues. In particular embodiments said amino acid sequence forming random coil conformation consists of about 100 to 1000 amino acid residues as characterized herein, i.e. comprising alanine, serine and proline as main or unique residues as defined below. The gist of the present invention is, accordingly, the provision of amino acid polymers that form random coil conformation under physiological conditions and consist mainly of these three amino acid residues, whereby proline residues represent preferably about 4% to about 40% of the random coil forming domain. The alanine and serine residues comprise the remaining at least 60% to 96% of said random coil forming domain. However, as will be detailed herein below said random coil forming domain may also comprise further amino acids differing from alanine, serine, and proline, i.e. as minor constituents.

The term "at least about 100/150/200/250/300/300/350 (etc) amino acid residues" is not limited to the concise number of amino acid residues but also comprises amino acid stretches that comprise an additional 10% to 20% or comprise 10% to 20% less residues. For example "at least about 100 amino acid residues" may also comprise 80 to 100 and about 100 to 120 amino acid residues without deferring from the gist of the present invention. Preferably, the "second domain" of the inventive biologically active protein(s)/polypeptide(s) comprises a maximal length of about 1000 amino acid residues. However, also longer "second domains" are envisaged in context of the present invention, i.e. "second domains" providing for the desired random coil conformation under physiological conditions and comprising up to about 3000 amino acid residues. Again, the term "about" in this context is not limited or restricted to the concise amount of amino acid residues but may also comprise +/− about 10% or +/− about 20% without deferring from this invention.

In context of this invention, it was surprisingly found that amino acid polymers consisting mainly of alanine and serine residues or, in a preferred embodiment consisting mainly or uniquely of alanine, serine, and proline residues, form random coil conformation under physiological conditions. Accordingly, the present invention provides for modules/sequence units/polymer repeats/polymer cassettes/building blocks consisting of alanine, serine, and proline which can be used as (a) part(s) of the herein defined "second domain" of a biologically active protein/polypeptide. Yet, the skilled person is aware that an amino acid polymer also may form random coil conformation when other residues than alanine, serine, and proline are comprised as a minor constituent in said "second domain". The term "minor constituent" as used herein means that maximally 10% i.e. maximally 10 of 100 amino acids may be different from alanine, serine and proline, preferably maximally 8% i.e. maximally 8 of 100 amino acids may be different than alanine, serine and proline, more preferably maximally 6% i.e. maximally 6 of 100 amino acids may be different from alanine, serine and proline, even more preferably maximally 5% i.e. maximally 5 of 100 amino acids may be different from alanine, serine and proline, particularly preferably maximally 4% i.e. maximally 4 of 100 amino acids may be different from alanine, serine and proline, more particularly preferably maximally 3% i.e. maximally 3 of 100 amino acids may be different from alanine, serine and proline, even more particularly preferably maximally 2% i.e. maximally 2 of 100 amino acids may be different from alanine, serine and proline and most preferably maximally 1% i.e. maximally 1 of 100 of the amino acids that encode the random coil forming domain may be different from alanine, serine and proline. Said amino acids different from alanine, serine and proline may be selected from the group consisting of Arg, Asn, Asp, Cys, Gln, Glu, Gly, His, Ile, Leu, Lys, Met, Phe, Thr, Trp, Tyr, and Val.

The amino acid polymers as disclosed herein and consisting of alanine, serine, and proline according to the invention were surprisingly found to adopt random coil conformation under physiological conditions. Therefore, they are advantageous molecules to provide for the herein defined "second domain" of the inventive biologically active protein(s)/polypeptide(s), i.e. a polypeptide stretch that forms under physiological conditions a random coil conformation and thereby mediates an increased in vivo and/or in vitro stability to biologically active ("functional") protein(s) or polypeptide(s). The hydrodynamic volume of a functional protein that is fused to said random coil domain is dramatically increased as can be estimated by using standard methods mentioned herein and also illustrated in the appended examples. Since the random coil domain is thought not to adopt a stable structure or function by itself, the biological activity mediated by the functional protein of interest to which it is fused is essentially preserved. Moreover, the amino acid polymers that form random coil domain as disclosed herein are thought to be biologically inert, especially with respect to proteolysis in blood plasma, immunogenicity, isoelectric point/electrostatic behaviour, binding to cell surface receptors as well as internalisation, but still biodegradable, which provides clear advantages over synthetic polymers such as PEG.

In another embodiment, the amino acid polymers adopting random coil conformation under physiological conditions comprise a plurality of "amino acid repeats"/"amino acid cassettes"/"cassette repeats", wherein said "amino acid repeats"/"amino acid cassettes"/"cassette repeats" consist of Ala, Ser, and Pro residues (depicted herein as "PAS", or as "APS") and wherein no more than 6 consecutive amino acid residues are identical and wherein said proline residues constitute more than 4% and less than 40% of the amino acids of said second domain forming random coil. Amino acid polymers adopting random coil conformation under physiological conditions may comprise a plurality of identical amino acid repeats/cassette repeats or a plurality of non-identical amino acid repeats. Non-limiting examples of "amino acid repeats", "building blocks", "modules", "repeats", "amino acid cassettes" etc. consisting of Ala, Ser and Pro residues are provided herein below; see SEQ ID NO: 18, SEQ ID NO: 20, SEQ ID NO: 22, SEQ ID NO: 24, SEQ ID NO: 26 and SEQ ID NO: 28 or fragments or multimers of these sequences. A "fragment" comprises at least 3 amino acids and comprises at least one alanine, one serine and/or one proline.

The amino acid repeat according to the present invention may consist of at least 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid residues, wherein each repeat comprises (an) Ala, Ser, and Pro residue(s). In one embodiment, the amino acid repeat according to the present invention does not comprise more than 100 amino acid residues. Preferably, the amino acid repeat/cassette repeat as defined herein comprises more than about 4%, preferably more than about 5%, even more preferably more than about 6%, particularly preferably more than about 8%, more particularly preferably more than about 10%, even more particularly preferably more than about 15% and most preferably more than about 20% proline residues. Such an amino acid repeat/cassette repeat as defined herein preferably comprises less than about 40% or less than about 35% proline residues; see also the herein below provided PAS constructs.

In yet another embodiment, the amino acid polymers forming random coil conformation under physiological conditions have the formula (I):

$$Ser_x[Ala_ySer_z]_n$$

wherein said amino acid polymer according to formula (I) further comprises proline residues as defined herein and wherein x is independently selected from integer 0 to 6. Furthermore, for each n, y is independently selected from integer 1 to 6 and each z is independently selected from integer 1 to 6. n, finally, is any integer so that said second domain consists of at least about 100 amino acid residues, and in particular of at least about 100 to about 3000 amino acid residues, preferably to about 2000 and more preferably to about 1000 amino acid residues.

In preferred embodiments, the amino acid polymer comprising the above defined "amino acid repeats"/"amino acid cassettes"/"cassette repeats" forming random coil conformation comprises no more than 5 identical consecutive amino acid residues, more preferably no more than 4 identical consecutive amino acid residues and most preferably no more than 3 identical consecutive amino acid residues.

As already indicated herein above, the amino acid polymer of the invention which forms random coil conformation comprises proline residues, wherein said proline residues constitute more than about 4%, preferably more than about 5%, even more preferably more than about 6%, particularly preferably more than about 8%, more particularly preferably more than about 10%, even more particularly preferably more than about 15% and most preferably more than about 20% of the amino acids constituting the random coil forming domain. Such an amino acid polymer of the invention which forms random coil conformation preferably comprises less than about 40%, or less than about 35% of the amino acids constituting the random coil forming domain. As shown in appended Example 13, the PAS#1P2 polymer with its smaller proportion of Pro residues shows a less pronounced minimum around 200 nm in its CD spectrum, indicating a dependency of the random coil character of the amino acid polymers according to this invention upon the content of proline residues.

In another preferred embodiment, the amino acid polymer comprising the above defined "amino acid repeats"/"amino acid cassettes"/"cassette repeats" forming random coil conformation comprises more than about 4% but less than about 50%, preferably more than about 10% but less than about 50% and most preferably more than about 20% but less than about 50% alanine residues of the amino acids constituting the random coil forming domain.

In a further preferred embodiment, the amino acid polymer forming comprising the above defined "amino acid repeats"/"amino acid cassettes"/"cassette repeats" random coil conformation comprises more than about 4% and less than about 50%, preferably more than about 10% but less than about 50% and most preferably more than about 20% but less than about 50 serine residues of the amino acids constituting the random coil forming domain.

Accordingly, the amino acid polymer forming random coil conformation may comprise about 35% proline residues, about 50% alanine residues and about 15% serine residues of the amino acids constituting the random coil forming domain. Alternatively, the amino acid polymer forming random coil conformation may comprise about 35% proline residues, about 15% alanine residues and about 50% serine residues of the amino acids constituting the random coil forming domain. The term "about" as used herein above relates also to the precise value of the given percentage.

Further described herein are amino acid polymers comprising the amino acid sequence selected from the group consisting of AAAASSASSASSSSSAAASA (piSA; SEQ ID NO: 2) AASAAASSAAASAAAASASS (SEQ ID NO: 4), ASASASASASASSSAASAASA (SEQ ID NO: 6), SAASS- SASSSSAASSASAAAA (SEQ ID NO: 8), SSS- SAASAASAAAAASSSAS (SEQ ID NO: 10), SSASS- SAASSSASSSSASAA (SEQ ID NO: 12), SASASASASASAASSASSAS (SEQ ID NO: 14) and ASSAAASAAAASSAASASSS (SEQ ID NO: 16). The multimers of the described alanine-serine modules/sequence units may form random coil conformation in case the resulting amino acid sequence further comprises proline residues as defined herein above. These exemplified modules/sequence units may be encoded by nucleic acid molecules comprising the following sequences

```
                                        (SEQ ID NO: 1)
GCCGCTGCTGCATCCTCTGCAAGCTCCGCTTCTTCCTCTAGCTCCGC
AGCTGCATCTGCT, (SEQ ID NO: 3)
GCTGCTTCCGCTGCTGCTTCCTCCGCTGCTGCTTCCGCTGCTGCTGC
TTCCGCTTCCTCC, (SEQ ID NO: 5)
GCTTCCGCTTCCGCTTCCGCTTCCGCTTCCTCCGCTGCTTC
CGCTGCTTCCGCT, (SEQ ID NO: 7)
TCCGCTGCTTCCTCCTCCGCTTCCTCCTCCTCCGCTGCTTCCTCCGC
TTCCGCTGCTGCT, (SEQ ID NO: 9)
TCCTCCTCCTCCGCTGCTTCCGCTGCTTCCGCTGCTGCTGCTGCTTC
CTCCTCCGCTTCC, (SEQ ID NO: 11)
TCCTCCGCTTCCTCCTCCGCTGCTTCCTCCTCCGCTTCCTCCTCCTC
CGCTTCCGCTGCT, (SEQ ID NO: 13)
TCCGCTTCCGCTTCCGCTTCCGCTTCCGCTTCCGCTGCTTCCTCCGC
TTCCTCCGCTTCC
and (SEQ ID NO: 15)
GCTTCCTCCGCTGCTGCTTCCGCTGCTGCTGCTTCCTCCGCTGCTTC
CGCTTCCTCCTCC.
```

In a preferred embodiment, the amino acid polymer forming random coil conformation comprises the amino acid sequence selected from the group consisting of ASPAAPA-PASPAAPAPSAPA (PAS#1; SEQ ID NO: 18), AAPASPA-PAAPSAPAPAAPS (PAS#2; SEQ ID NO: 20), SAPSSPSP-SAPSSPSPASPS (modified PAS#3; modified SEQ ID NO: 22), APSSPSPSAPSSPSPASPSS (PAS#3, SEQ ID No. 22, non-modified). In an alternative, a slightly modified, yet active PAS#3 may have the above recited sequence SAPSSPSPSAPSSPSPASPS (SEQ ID NO: 63). This sequence corresponds to the herein provided SEQ ID No. 22 in a circularly permuted form, wherein the last serine was removed and another serine was appended as starting amino acid. As a consequence, multimers of this modified sequence according to the invention possess essentially the same internal repeating unit as multimers of the non-modified sequence, except for the very first and the very last residue. Accordingly, this modified PAS#3 (SEQ ID NO: 63) may be considered as an example of a further "module"/"building block" of the herein provided amino acid polymers in accordance with this invention. It is clear for the person skilled in the art that also other "modules" and (shorter) fragments or circularly permuted versions of the herein provided amino acid polymers may be used as "modules", "repeats" and/or building blocks for the herein defined "second domain" of the provided biologically active protein. Yet, even further and illustrative amino acid polymers forming random coil conformation may comprise amino acid sequences that may be selected from the group consisting SSPSAPSPSSPASPSPSSPA (PAS#4; SEQ ID NO: 24), AASPAAPSAPPAAASPAAPSAPPA (PAS#5; SEQ ID NO: 26) and ASAAAPAAASAAASAPSAAA (PAS#1P2; SEQ ID NO: 28). Again, also or (a) fragments or (a) multimers(s) or circularly permuted versions of these sequences and the sequences provided herein above may be employed in context of the present invention as building blocks for the herein defined "second domain" of the inventive biologically active protein(s)/polypeptide(s). The person skilled in the art is readily in a position to generate further amino acid polymers that form random coil conformation under physiological conditions and are constituted of mainly alanine, serine, and proline as defined herein. Such other and further examples of random coil conformation forming amino acid polymers to be used as building blocks or modules of the herein defined "second domain" of the inventive biologically active protein(s)/polypeptide(s) may, inter alia, comprise combinations and/or fragments or circularly permuted versions of the specific "building blocks", "polymer cassettes" or "polymer repeats" shown above. Accordingly, the exemplified modules/sequence units/polymer repeats/polymer cassettes of the random coil domain may also provide for individual fragments which may be newly combined to form further modules/sequence units/polymer repeats/polymer cassettes in accordance with this invention.

The terms "module(s)", "sequence unit(s)", "polymer repeat(s)", "polymer cassette(s)" and "building block(s) are used as synonyms herein and relate to individual amino acid stretches which may be used to form the herein defined "second domain" of the inventive biologically active protein/polypeptide. Said second domain comprises an amino acid sequence consisting preferably of at least about 100 amino acid residues and forms a random coil conformation under physiological conditions.

The above exemplified modules/sequence units/polymer repeats/polymer cassettes/building blocks of the random coil domain of the inventive biologically active proteins/polypeptides (i.e the herein defined "second domain" of said biologically active proteins/polypeptide) may be encoded by nucleic acid molecules comprising the following sequences (SEQ ID NO: 17)
GCCTCTCCAGCTGCACCTGCTCCAGCAAGCCCTGCTGCACCAGCTCC
GTCTGCTCCTGCT, (SEQ ID NO: 19)
GCTGCTCCGGCTTCCCCGGCTCCGGCTGCTCCGTCCGCTCCGGCTCC
GGCTGCTCCGTCC, (SEQ ID NO: 21)
GCTCCGTCCTCCCCGTCCCCGTCCGCTCCGTCCTCCCCGTCCCGGC
TTCCCCGTCC-TCC, (SEQ ID NO: 23)
TCCTCCCCGTCCGCTCCGTCCCCGTCCTCCCCGGCTTCCCCGTCCCC
GTCCTCCCCGGCT, (SEQ ID NO: 25)
GCCGCTTCTCCAGCAGCTCCTTCTGCTCCACCAGCAGCTGCAAGCCC
TGCTGCACCAAGCGCACCTCCTGCT
and/or (SEQ ID NO: 27)
GCCTCTGCTGCAGCACCTGCAGCAGCAAGCGCAGCTGCATCTGCTCC
ATCTGCAGCTGCT.

A modified PAS#3 (modified SEQ ID NO: 22) as described herein above may be encoded by the following nucleic acid sequence:

(modified SEQ ID NO: 21)
TCCGCTCCGTCCTCCCCGTCCCCGTCCGCTCCGTCCTCCCCGTCCCC

GGCTTCCCCGTCC.

It is of note and non-limiting for the present invention that, in accordance with the knowledge of the skilled artisan that the herein described and exemplified modules/sequence units/polymer repeats/polymer cassettes/building blocks of the random coil domain (or fragments of the same or multimers or circularly permuted versions of the same) may be encoded by different nucleic acid sequences in accordance with the genetic code, which is of degenerate nature, i.e. different nucleotide triplet codons may encode the same amino acid residue. In addition, the terminal residues may differ, depending on the design of a nucleotide sequence cassette according to this invention and on the ligation strategy applied to obtain multimers thereof. For example, the "module" PAS#1 as shown in SEQ ID NO: 18 and 30 may be encoded by nucleic acid sequences SEQ ID NO: 17 and 29, respectively. In contrast to SEQ ID NO: 18, SEQ ID NO: 30 comprises an additional alanine at the C-terminus, whose codon may be deleted if individual nucleotide sequence cassettes are ligated via sticky ends as described in some of the appended Examples.

In accordance with the above, the amino acid polymer forming random coil conformation may comprise a multimer consisting of either one of the amino acid sequences with SEQ ID NO: 18, 20, 22, 24, 26 or 28 as disclosed herein above or may comprise a multimer consisting of more than one of amino acid sequences SEQ ID NO: 18, 20, 22, 24, 26 and 28. Furthermore, it is envisaged that also fragments or circularly permuted versions of these exemplified sequences are used to build up further modules/sequence units/polymer repeats/polymer cassettes/building blocks of the random coil domain ("second domain") of the inventive biologically active protein(s)/polypeptide(s).

In another embodiment, the amino acid polymer forming random coil conformation may comprise a multimer consisting of a (circular) permutation of the amino acid sequence selected from the group consisting of ASPAAPAPASPAAPAPSAPA (SEQ ID NO: 18), AAPASPAPAAPSAPAPAAPS (SEQ ID NO: 20), APSSPSPSAPSSPSPASPSS (SEQ ID NO: 22), or as modified sequence S-APSSPSPSAPSSPS-PASPS (SEQ ID NO: 63), SSPSAPSPSSPASPSPSSPA (SEQ ID NO: 24), AASPAAPSAPPAAASPAAPSAPPA (SEQ ID NO: 26) and ASAAAPAAASAAASAPSAAA (SEQ ID NO: 28) or (a) multimers(s) of these (circular) permutated sequences.

In yet another embodiment, the amino acid polymer forming random coil conformation may comprise a multimer consisting of a fragment/part of the amino acid sequence selected from the group consisting of ASPAAPAPASPAAPAPSAPA (SEQ ID NO: 18), AAPASPAPAAPSAPAPAAPS (SEQ ID NO: 20), APSSPSPSAPSSPSPASPSS (SEQ ID NO: 22; or as modified sequence S-APSSPSPSAPSSPSPASPS ((SEQ ID NO: 63)), SSPSAPSPSSPASPSPSSPA (SEQ ID NO: 24), AASPAAPSAPPAAASPAAPSAPPA (SEQ ID NO: 26) and ASAAAPAAASAAASAPSAAA (SEQ ID NO: 28) or (a) multimers(s) of these exemplified modules/sequence units/polymer repeats/polymer cassettes/building blocks. "Fragments" of these sequences to be employed in accordance with this invention for the generation of the "second domain" of the inventive biologically active protein/polypeptide may consist of at least 3, preferably of at least 4, more preferably of at least 5, even more preferably of at least 6, still more preferably of at least 8, particularly preferably of at least 10, more particularly preferably of at least 12, even more particularly preferably of at least 14, still more particularly preferably of at least 16, and most preferably of at least 18 consecutive amino acids of the amino acid sequence selected from the group consisting of said SEQ ID NOs: 18, 20, 22, 24, 26 and 28.

As mentioned herein above, the herein provided modules/sequence units/building blocks etc. of the random coil domain are merely examples of the inventive amino acid polymer that forms random coil conformation under physiological conditions. In accordance with the gist of the present invention these "modules", "sequence units" and/or "repeats" comprise the above-identified content/fraction of alanine, serine and proline. Therefore, it is within the normal skill of the artisan to generate further such "modules", "sequence units" and/or "repeats" in accordance with this invention. For example, individual fragments of the herein identified inventive "modules", "sequence units" and/or "repeats" may be combined to further individual "modules", "sequence units" and/or "repeats", as long as the above-identified rules for the overall distribution and amount of alanine, serine and proline are respected. Again, these "modules", "sequence units" and/or "repeats" may also comprise further amino acid residues, however only as minimal or minor constituents (maximally 10%, preferably maximally 2% of the individual "module", "sequence unit" and/or "repeat"). Said individual "module", "sequence unit" and/or "repeat" consists, in accordance with this invention, of at least about 100 amino acid residues. Individual "modules", "sequence units" and/or "repeats" may be combined in order to form longer random coil forming amino acid polymers, whereby a maximal length of the herein defined "second domain" of a biologically active protein is about 3000 amino acids. Preferred are in context of this invention biologically active proteins that comprise at least two domains wherein a first domain as defined herein above of said at least two domains comprises an amino acid sequence having and/or mediating said biological activity; and a second domain of said at least two domains as defined herein comprises an amino acid sequence consisting preferably of at least about 100 amino acid residues and random coil conformation under physiological conditions. Said random coil conformation as provided herein and consisting mainly of alanine, serine, and proline mediates an increased in vivo and/or in vitro stability of said biologically active protein. Said second domain may be comprised of the individual "modules", "sequence units" and/or "repeats" as provide herein or may comprise fragments or parts of these individual, illustrative "modules", "sequence units" and/or "repeats". However, said second domain may be build of further and or other individual "modules", "sequence units", "building blocks" and/or "repeats" which respect and follow the teachings provided herein above and which are exemplified herein below in the specification and the appended examples. For example, the appended experimental part shows ample evidence that proteins comprising a herein defined, additional "second domain" providing for a random coil confirmation under physiological conditions (for example polymers consisting of about 200 or about 400 or about 600 amino acid residues and comprising PAS#1/SEQ ID NO. 18, PAS#2/SEQ ID No. 20, PAS#3/SEQ ID NO$_{22}$, PAS#5/SEQ ID NO. 26 and/or PAS#1P2/SEQ ID NO 28 as "building blocks") have an advantageous serum stability or plasma half-life, even in vivo as compared to the non-modified biologically active protein. As non-limiting example of the present invention, the in vivo stability of non-modified IFNa2b was compared to the in vivo stability of modified IFNa2b that comprised an additional "second domain" as defined herein, adopting a random coil conformation under physiological conditions.

Homo-polymers of most amino acids, in particular the hydrophobic amino acids, are usually insoluble in aqueous solution (Bamford (1956) Synthetic Polypeptides—Preparation, *Structure, and Properties,* 2nd ed., Academic Press, New York). Homo-polymers of several hydrophilic amino acids are known to form secondary structures, for example α-helix in the case of Ala (Shental-Bechor (2005) Biophys J 88:2391-2402) and β-sheet in the case of Ser (Quadrifoglio (1968) J Am Chem Soc 90:2760-2765) while poly-proline, the stiffest homooligopeptide (Schimmel (1967) Proc Natl Acad Sci USA 58:52-59), forms a type II trans helix in aqueous solution (Cowan (1955) Nature 176:501-503).

Using the theoretical principles of polymer biophysics the random coil diameter of a chain of 200 amino acid residues would amount in the case of poly-glycine, for example, to ca. 75 Å—calculated as the average root mean square end-to-end distance of $\sqrt{\langle r^2 \rangle}_0 = I \cdot \sqrt{n \cdot C_\infty}$, with n=200 rotatable bonds of length l=3.8 Å for each $C_\alpha$-$C_\alpha$ distance and the 'characteristic ratio' $C_\infty \approx 2.0$ for poly(Gly) (Brant (1967) J Mol Biol 23:47-65; Creighton, (1993) loc. cit.). This relation shows that the person skilled in the art would expect that the hydrodynamic volume of a random chain amino acid polymer can be either extended by (a) using a longer chain length l or by (b) using amino acids that exhibit a larger characteristic ratio, $C_\infty$. $C_\infty$ is a measure for the inherent stiffness of the molecular random chain and has a general value of 9 for most amino acids (Brant (1967) loc. cit.). Only Gly, which lacks a side chain, and also the imino acid Pro exhibit significantly smaller values. Hence, Gly and Pro (under denaturing conditions) are expected to contribute to reducing the dimensions of random coil proteins (Miller (1968) Biochemistry 7:3925-3935). Amino acid polymers comprising proline residues, accordingly, are expected to have a relatively compact hydrodynamic volume. In contrast to this teaching, however, it is shown herein that the hydrodynamic volume of the amino acid polymers of the invention that comprise a mixture of alanine, serine, and proline residues have a dramatically increased hydrodynamic volume as determined by analytical gel permeation chromatography when compared to the expected hydrodynamic volume. In fact, it is surprising that polypeptides comprising mixtures of these three amino acids, of which each alone tends to form a homooligopeptide with defined secondary structure, adopt random coil conformation under physiological conditions. Such inventive polypeptides have a larger hydrodynamic radius than homo-polymers comprising the same number of Gly residues and they confer better solubility to the biologically active protein according to the invention.

WO 2006/081249 describes protein conjugates comprising a biologically active protein coupled to a polypeptide comprising 2 to 500 units of an amino acid repeat having Gly, Asn, and Gln as a major constituent and Ser, Thr, Asp, Gln, Glu, His, and Asn as a minor constituent. Said protein conjugates are described to have either an increased or a decreased plasma half-life when compared to the unconjugated biologically active protein. WO 2006/081249, however, does not provide any teaching to predict whether a specific amino acid repeat reduces or augments the plasma half-life of the conjugate. Moreover, WO 2006/081249 does not teach or suggest that the plasma half-life of proteins can be increased when the conjugated protein comprises an amino acid repeat that forms random coil conformation as shown in the present invention. Furthermore, the amino acid repeats disclosed in WO 2006/

081249 comprise at least two residues selected from Gly, Asn, and Gln, which is in clear contrast with the polypeptide repeats of the present invention that preferentially consist of Ala, Ser, and Pro residues.

As used herein, the term "biological activity" describes the biological effect of a substance on living matter. Accordingly, the terms "biologically active protein" or "polypeptide having and/or mediating biological activity" as used herein relate to proteins or polypeptides that are capable of inducing a biological effect in living cells/organisms that are exposed to said protein or polypeptide. Yet, it is of note that in the context of the present invention, the term "biologically active protein" relates to the whole protein of the invention which both comprises an amino acid sequence having and/or mediating said biological activity and an amino acid sequence forming random coil conformation.

Accordingly, the terms "amino acid sequence having and/or mediating biological activity" or "amino acid sequence with biological activity" as used herein relate to the above-defined "first domain" of the biologically active protein of the invention, mediating or having or being capable of mediating or having the above defined "biological activity". The terms "amino acid sequence having and/or mediating biological activity" or "amino acid sequence with biological activity" also relate to a "biologically active polypeptide" or "biologically active polypeptide stretch" of the invention and relating to the "first domain" of said biologically active protein. Also comprised in the terms "amino acid sequence having and/or mediating biological activity" or "amino acid sequence with biological activity" are functional fragments of any protein of interest, the half-life of which, either in vivo or in vitro, needs to be prolonged. In one embodiment of this invention, the amino acid sequence having and/or mediating biological activity in accordance with the present invention may be deduced from any "protein of interest", i.e. any protein of pharmaceutical or biological interest or any protein that is useful as a therapeutic/diagnostic agent. Accordingly, the biologically active proteins in accordance with the present invention may comprise a biologically active amino acid sequence which is derived from naturally produced polypeptides or polypeptides produced by recombinant DNA technology. In a preferred embodiment, the protein of interest may be selected from the group consisting of binding proteins, immunoglobulins, antibody fragments, transport proteins, signaling proteins/peptides such as cytokines, growth factors, hormones or enzymes.

As used herein, the term "binding protein" relates to a molecule that is able to specifically interact with (a) potential binding partner(s) so that it is able to discriminate between said potential binding partner(s) and a plurality of different molecules as said potential binding partner(s) to such an extent that, from a pool of said plurality of different molecules as potential binding partner(s), only said potential binding partner(s) is/are bound, or is/are significantly bound. Methods for the measurement of binding of a binding protein to a potential binding partner are known in the art and can be routinely performed e.g. by using ELISA, isothermal titration calorimetry, equilibrium dialysis, pull down assays or a Biacore apparatus. Exemplary binding proteins which are useful in the context of the present invention include, but are not limited to antibodies, antibody fragments such as Fab fragments, F(ab')$_2$ fragments, single chain variable fragments (scFv), isolated variable regions of antibodies (VL- and/or VH-regions), CDRs, single domain antibodies, CDR-derived peptidomimetics, lectins, lipocalins or various types of scaffold-derived binding proteins as described, for example, in Skerra (2000) J Mol Recognit 13:167-187 or Binz (2005) Nat Biotechnol 23:1257-1268.

Other exemplary biologically active proteins of interest which are useful in the context of the present invention include, but are not limited to granulocyte colony stimulating factor, human growth hormone, α-interferon, β-interferon, γ-interferon, tumor necrosis factor, erythropoietin, coagulation factors such as coagulation factor VIII, gp120/gp160, soluble tumor necrosis factor I and II receptor, thrombolytics such as reteplase, exendin-4, interleukin-1 receptor antagonists such as anakinra, interleukin-2 and neutrophil gelatinase-associated lipocalin or those listed in Walsh (2003) Nat Biotechnol 21:865-870 or Walsh (2004) Eur J Pharm Biopharm 58:185-196.

The neutrophil gelatinase-associated lipocalin (NGAL; also called human neutrophil lipocalin, 24p3, uterocalin, siderocalin, or neu-related lipocalin) as mentioned herein above is a member of the lipocalin family of binding proteins, which was first identified as a neutrophil granule component. NGAL and was shown to tightly bind the catecholate-type siderophore FeIII•enterochelin/enterobactin (Goetz (2002) Mol Cell 10:1033-1043) as well as some other siderophores of mycobacteria, including *M. tuberculosis* carboxymycobactins (Holmes (2005) Structure 13:29-41). These siderophores are highly potent iron chelators which are secreted by pathogenic bacteria in response to limiting iron concentrations, as they occur in the human body fluids, and allow iron uptake by specialized bacterial import systems. Hence, neutrophils seem to release NGAL (recently also dubbed 'siderocalin') at sites of infection as an antimicrobial strategy of the innate immune system. The physiological relevance of NGAL has been investigated in corresponding knock-out mice and shown to limit the growth of bacteria that produce enterochelin (Flo (2004) Nature 432:917-921). Consequently, NGAL might be applied as a novel kind of antibiotic that acts by preventing bacterial iron uptake. Apart from that NGAL was described to participate in a physiological pathway for iron-retrieval by the kidney (Yang (2002) Mol Cell 10:1045-1056). This mechanism was recently demonstrated to prevent the kidney from ischemia-reperfusion injury in a mouse model of severe renal failure (Mori (2005) J Clin Invest 115:610-621), which could open another area of therapeutic application.

In yet another embodiment, the present invention relates to the biologically active protein of the invention, wherein said first domain comprising an amino acid sequence that encodes a polypeptide having and/or mediating said biological activity and said second domain that forms random coil conformation are connected by a polypeptide linker. This polypeptide linker, inserted between said first and said second domains, preferably comprises plural, hydrophilic, peptide-bonded amino acids that are covalently linked to these domains. In yet another embodiment said polypeptide linker comprises a plasma protease cleavage site which allows the controlled release of said first domain comprising a polypeptide having and/or mediating a biological activity. Linkers of different types or lengths may be identified without undue burden to obtain full functional activity of specific polypeptides.

In a preferred embodiment, the biologically active proteins of the present invention are fusion proteins. A fusion protein as described herein is meant to comprise at least one domain which mediates a biological activity and at least one other domain which forms random coil conformation in a single multi-domain polypeptide. In an alternative embodiment, the biologically active protein in accordance with the present invention may represent a protein conjugate wherein a protein of interest or a polypeptide/polypeptide stretch/amino acid sequence having and/or mediating biological activity is conjugated via a non-peptide bond to an amino acid sequence which forms random coil conformation. Non-peptide bonds that are useful for cross-linking proteins are known in the art and may include disulfide bonds, e.g. between Cys side chains, thioether bonds or non-peptide covalent bonds induced by chemical cross-linkers, such as disuccinimidyl suberate (DSS) or sulfosuccinimidyl 4-[p-maleimidophenyl] butyrate (Sulfo-SMPB), as well as non-covalent protein-protein interactions.

It is of note that the "biologically active protein" of the present invention may also comprise more than one "amino acid sequence having and/or mediating a biological activity", i.e. the herein defined "first domain" of the biologically active protein is not limited in context of this invention to one single biological activity of interest. Furthermore, the person skilled in the art is aware that the "amino acid sequence having and/or mediating a biological activity" and the "random coil domain/part" as comprised in the biologically active proteins of the invention may be organized in a specific order. A non-limiting example of a "biologically active protein" of the present invention comprising one random coil domain/part (i.e. an amino acid sequence consisting of at least about 100 amino acid residues and forming a random coil) and two amino acid sequences having and/or mediating different biological activities, the domain order may be: "amino acid sequence having and/or mediating first biological activity"—"random coil domain/part"—"amino acid sequence having and/or mediating second biological activity".

Accordingly, and in the context of the invention, the order of the herein defined "first" and "second" domain of the inventive biologically active polypeptide may be arranged in an order, whereby said "first domain" (i.e. protein of interest; "amino acid sequence having and/or mediating said biological activity") is located at the amino (N-) terminus and said "second domain" (i.e. the domain that comprises an amino acid sequence consisting of at least about 100 amino acid residues forming/adopting random coil conformation) is located at the carboxy (C-) terminus of the inventive polypeptide. However, this order may also be reversed, e.g. said "first domain" (i.e. protein of interest; "amino acid sequence having and/or mediating said biological activity") is located in/at the carboxy (C-) terminus and said "second domain" (i.e. the domain that comprises an amino acid sequence consisting of at least about 100 amino acid residues forming/adopting random coil conformation) is located in/at the amino (N-) terminus of the inventive polypeptide.

Yet, as pointed out above, it is also envisaged that more than one domain comprising or consisting of an amino acid sequence having and/or mediating said biological activity are to be used in context of the inventive polypeptide construct. Accordingly, said "second domain" (i.e. the domain that comprises an amino acid sequence consisting of at least about 100 amino acid residues forming/adopting random coil conformation) may be located between said "first domains", being amino acid stretches that have and/or mediate a biological activity of interest or desire. The "random coil stretch" may, therefore, be located between the two domains having and/or mediating the desired biological activity. As with all embodiments of the present inventive polypeptide/biologically active protein, said domain(s) comprising an amino acid sequence having and/or mediating the said biological activity may also be a biologically active fragment of a given protein with a desired biological function. Therefore, the herein defined "second domain" (an amino acid sequence consisting of at least about 100 amino acid residues forming a random coil) may also be located between two biologically active fragments of a protein of interest or between biologically active fragments of two proteins of interest. Yet, also when more than one domain "having and/or mediating a biological activity" are to be comprised in the biologically active protein of this invention, the herein defined "second domain", i.e. the amino acid sequence consisting of at least about 100 amino acid residues forming a random coil conformation, may be located at the N- or C-terminus of the biological active protein of this invention. Corresponding, non-limiting examples, starting from the N-terminus, are:

"amino acid sequence having and/or mediating first biological activity"—"random coil domain/part"—"amino acid sequence having and/or mediating second biological activity"

or

"amino acid sequence having and/or mediating first biological activity"—"amino acid sequence having and/or mediating second biological activity"—"random coil domain/part"

or

"random coil domain/part"—"amino acid sequence having and/or mediating first biological activity"—"amino acid sequence having and/or mediating second biological activity"

The corresponding order(s) is/are also envisaged when the representation starts from the C-terminus of the biologically active protein/polypeptide of the present invention. The term "random coil domain/part" as used herein in the representations above corresponds to the "second domain" as defined herein, i.e. to an amino acid sequence consisting of at least about 100 amino acid residues that adopts/has random coil conformation under physiological conditions. Again, it has to be pointed out that the term "amino acid sequence having and/or mediating first biological activity" is not limited to full-length polypeptides that have and/or mediate said biological activity or function, but also to biologically and/or pharmacologically active fragments thereof. Especially, but not only, in a context wherein two or more "first domains" as defined herein are comprised in the inventive "biologically active protein", it is also envisaged that these "first domains" are or represent different parts of a protein complex or fragments of such parts of protein complex.

Moreover, it is also envisaged that more than one domain comprising an amino acid sequence consisting of at least about 100 amino acid residues forming/adopting random coil conformation are to be used in context of the inventive polypeptide construct. Accordingly, said "first domains", being amino acid stretches that have and/or mediate a biological activity of interest or desire may be located between two "second domains" (i.e. domains that comprise an amino acid sequence consisting of at least about 100 amino acid residues forming/adopting random coil conformation). Therefore "random coil stretches" may be located both N-terminally and C-terminally of the domain having and/or mediating the desired biological activity.

As exemplified herein below, the biologically active proteins of the invention which are modified to comprise a random coil domain surprisingly exhibit an increased in vivo and/or in vitro stability when compared to unmodified biologically active proteins that lack said random coil domain. As used herein, the term "in vivo stability" relates to the capacity of a specific substance that is administered to the living body to remain biologically available and biologically active. In vivo, a substance may be removed and/or inactivated due to excretion, aggregation, degradation and/or other metabolic processes. Accordingly, in the context of the present invention biologically active proteins that have an increased in vivo stability may be less well excreted through the kidneys (urine) or via the feces and/or may be more stable against proteolysis, in particular against in vivo proteolysis in biological fluids, like blood, liquor cerebrospinalis, peritoneal fluid and lymph. In one embodiment, the increased in vivo stability of a biologically active protein manifests in a prolonged plasma half-life of said biologically active protein.

Methods for measuring the in vivo stability of biologically active proteins are known in the art. As exemplified herein below, biologically active proteins may be specifically detected in the blood plasma using western blotting techniques or enzyme linked immunosorbent assay (ELISA). Yet, the person skilled in the art is aware that other methods may be employed to specifically measure the plasma half-life of a protein of interest. Such methods include, but are not limited to the physical detection of a radioactively labelled protein of interest. Methods for radioactive labelling of proteins e.g. by radioiodination are known in the art.

The term "increased in vitro stability" as used herein relates to the capacity of a biologically active protein to resist degradation and/or aggregation and to maintain its original biological activity in an in vitro environment. Methods for measuring the biological activity of biologically active proteins are well known in the art.

In another embodiment, the present invention relates to nucleic acid molecules encoding the biologically active proteins as described herein. Accordingly, said nucleic acid molecule may comprise a nucleic acid sequence encoding a polypeptide having biological activity and a nucleic acid sequence encoding an amino acid sequence which forms/adopts random coil conformation. In yet another embodiment said nucleic acid molecule may comprise a nucleic acid sequence encoding one of the herein disclosed amino acid sequences that form/adopt random coil conformation. The term "nucleic acid molecule", as used herein, is intended to include nucleic acid molecules such as DNA molecules and RNA molecules. Said nucleic acid molecule may be single-stranded or double-stranded, but preferably is double-stranded DNA. Preferably, said nucleic acid molecule may be comprised in a vector.

Furthermore, it is envisaged to transfect cells with the nucleic acid molecule or vectors as described herein. In a further embodiment, the present invention relates to nucleic acid molecules which upon expression encode the biologically active proteins of the invention. Yet, in a further embodiment, the present invention relates to nucleic acid molecules which upon expression encode the herein disclosed polypeptides that, entirely or in part, form/adopt random coil conformation under physiological conditions. Said nucleic acid molecules may be fused to suitable expression control sequences known in the art to ensure proper transcription and translation of the polypeptide as well as signal sequences to ensure cellular secretion or targeting to organelles. Such vectors may comprise further genes such as marker genes which allow for the selection of said vector in a suitable host cell and under suitable conditions.

Preferably, the nucleic acid molecule of the invention is comprised in a recombinant vector in which a nucleic acid molecule encoding the herein described biologically active protein is operatively linked to expression control sequences allowing expression in prokaryotic or eukaryotic cells. Expression of said nucleic acid molecule comprises transcription of the nucleic acid molecule into a translatable mRNA. Regulatory elements permitting expression in prokaryotic host cells comprise, e.g., the lambda PL, lac, trp, tac, tet or T7 promoter in $E.$ $coli.$ Possible regulatory elements ensuring expression in eukaryotic cells, preferably mammalian cells or yeast, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Examples for regulatory elements permitting expression in eukaryotic host cells are the AOX1 or GAL1 promoter in yeast or the CMV, SV40, RSV promoter (Rous sarcoma virus), CMV enhancer, SV40 enhancer or a globin intron in mammalian and other animal cells. Apart from elements which are responsible for the initiation of transcription such regulatory elements may also comprise transcription termination signals, such as the SV40-poly-A site or the tk-poly-A site, downstream of the coding region.

Methods which are well known to those skilled in the art can be used to construct recombinant vectors (see, for example, the techniques described in Sambrook (1989), Molecular Cloning: A Laboratory Manual, Cold Spring Harbor Laboratory N.Y. and Ausubel (1989), Current Protocols in Molecular Biology, Green Publishing Associates and Wiley Interscience, N.Y.). In this context, suitable expression vectors are known in the art such as Okayama-Berg cDNA expression vector pcDV1 (Pharmacia), pCDM8, pRc/CMV, pcDNA1, pcDNA3, pPICZalphaA (Invitrogen), or pSPORT1 (GIBCO BRL). Furthermore, depending on the expression system that is used, leader sequences capable of directing the polypeptide to a cellular compartment or secreting it into the culture medium may be added to the coding sequence of the nucleic acid molecule of the invention.

The present invention also relates to vectors, particularly plasmids, cosmids, viruses, and bacteriophages that are conventionally employed in genetic engineering comprising a nucleic acid molecule encoding the biologically active protein of the invention. Therefore, the present invention also relates to vectors comprising the nucleic acid molecule of this invention. Preferably, said vector is an expression vector and/or a gene transfer or targeting vector. Expression vectors derived from viruses such as retroviruses, vaccinia virus, adeno-associated virus, herpes viruses or bovine papilloma virus may be used for delivery of the polynucleotides or vector of the invention into targeted cell populations. The vectors containing the nucleic acid molecules of the invention can be transferred into the host cell by well-known methods, which vary depending on the type of cellular host. Accordingly, the invention further relates to a cell comprising said nucleic acid molecule or said vector. Such methods, for example, include the techniques described in Sambrook (1989), loc. cit. and Ausubel (1989), loc. cit. Accordingly, calcium chloride transfection is commonly utilized for prokaryotic cells, whereas calcium phosphate treatment or electroporation may be used for other cellular hosts (see Sambrook (1989), loc. cit.). As a further alternative, the nucleic acid molecules and vectors of the invention can be reconstituted into liposomes for delivery to target cells. The nucleic acid molecule or vector of the invention which is present in host cell may either be integrated into the genome of the host cell or it may be maintained extra-chromosomally. Accordingly, the present invention also relates to a host cell comprising the nucleic acid molecule and/or the vector of this invention. Host cells for the expression of polypeptides are well known in the art and comprise prokaryotic cells as well as eukaryotic cells, e.g. $E.$ $coli$ cells, yeast cells, invertebrate cells, CHO-cells, CHO-K1-cells, Hela cells, COS-1 monkey cells, melanoma cells such as Bowes cells, mouse L-929 cells, 3T3 lines derived from Swiss, Balb-c or NIH mice, BHK or HaK hamster cell lines and the like.

In a further aspect, the present invention comprises methods for the preparation of the biologically active proteins of the invention comprising culturing the (host) cell of this invention and isolating said biologically active protein from the culture as described herein. The inventive biologically active protein comprising a random coil domain may be produced by recombinant DNA technology, e.g. by cultivating a cell comprising the described nucleic acid molecule or vectors which encode the inventive biologically active protein and isolating said biologically active protein from the culture. The inventive biologically active protein may be produced in any suitable cell-culture system including prokaryotic cells, e.g. *E. coli* BL21 or JM83, or eukaryotic cells, e.g. *Pichia pastoris* yeast strain X-33 or CHO cells. Further suitable cell lines known in the art are obtainable from cell line depositories, like the American Type Culture Collection (ATCC). The term "prokaryotic" is meant to include bacterial cells while the term "eukaryotic" is meant to include yeast, higher plant, insect and mammalian cells. The transformed hosts can be grown in fermentors and cultured according to techniques known in the art to achieve optimal cell growth. In a further embodiment, the present invention relates to a process for the preparation of a biologically active protein described above comprising cultivating a cell of the invention under conditions suitable for the expression of the biologically active protein and isolating the biologically active protein from the cell or the culture medium.

The biologically active protein of the invention can be isolated from the growth medium, cellular lysates or cellular membrane fractions. The isolation and purification of the expressed polypeptides of the invention may be performed by any conventional means (Scopes (1982), "Protein Purification", Springer-Verlag, N.Y.), including ammonium sulphate precipitation, affinity columns, column chromatography, gel electrophoresis and the like and may involve the use of monoclonal or polyclonal antibodies directed, e.g., against a tag fused with the biologically active protein of the invention. For example, the protein can be purified via the Strep-tag II using streptavidin affinity chromatography (Skerra (2000) Methods Enzymol 326:271-304) as described in the appended examples. Substantially pure polypeptides of at least about 90 to 95% homogeneity are preferred, and 98 to 99% or more homogeneity are most preferred, for pharmaceutical uses. Depending upon the host employed in the production procedure, the polypeptides of the present invention may be glycosylated or may be non-glycosylated.

The invention further relates to the use of the biologically active protein of the invention, the nucleic acid molecule of the invention, the vector of the invention or the (host) cell of the invention for the preparation of a medicament, wherein said biologically active protein has an increased in vivo and/or in vitro stability.

In yet another embodiment, the present invention relates to a method for the treatment of diseases and/or disorders that benefit from the improved stability of said biologically active protein, comprising administering the biologically active protein as described herein to a mammal in need of such treatment. Depending on the biological activity of the inventive protein, the skilled person is readily capable of determining which disease/disorder is to be treated with a specific biologically active protein of the invention. Some non-limiting examples are listed in the following table:

| biologically active protein (or a biologically active fragment thereof) | to be treated disorder/disease |
| --- | --- |
| granulocyte colony stimulating factor | cancer and/or chemotherapy related neutropenia |
| human growth hormone | growth hormone deficiency related hypoglycaemia and/or growth failure |
| alpha-interferon | cancer, viral infection, hepatitis C |
| beta-interferon | auto-immune disease, multiple sclerosis |
| gamma-interferon | viral infection |
| tumor necrosis factor | cancer |
| erythropoietin | anaemia |
| coagulation factor VIII | haemophilia |
| gp120/gp160 | HIV |
| soluble tumor necrosis factor I and II receptor | inflammatory disease |
| reteplase | thrombosis, myocardial infarction |
| exendin-4 | Diabetes |
| interleukin-1 receptor antagonist (IL-1ra; anakinra) | auto-immune disease, rheumatoid arthritis |
| interleukin-2 | cancer |
| insulin | diabetes |
| asparaginase | acute lymphoblastic leukemia, non-Hodgkin's lymphoma |
| onconase | malignant mesothelioma and other types of cancer |
| streptokinase | thrombotic disorders |
| neutrophil gelatinase-associated lipocalin | microbial infection, kidney reperfusion injury |
| antibodies and their fragments, including single domain antibodies, single chain and other engineered fragments including CDR mimetic peptides and CDRs | immunological, oncological, neovascular, and infectious diseases etc. |

The present invention also relates to the use of the nucleic acid molecules, vectors as well as transfected cells comprising the nucleic acid molecules or vectors of the present invention in medical approaches, like, e.g. cell based gene therapy approaches or nucleic acid based gene therapy approaches.

In a further embodiment, the inventive biologically active protein comprising the herein defined "first" and "second" domains (or the nucleic acid molecule or the vector or the host cell of the present invention) of the invention is part of a composition. Said composition may comprise one or more of the inventive biologically active proteins or nucleic acid molecules, vectors or host cells encoding and/or expressing the same.

Said composition may be a pharmaceutical composition, optionally further comprising a pharmaceutically acceptable carrier and/or diluent. In a further embodiment, the present invention relates to the use of the herein described biologically active protein for the preparation of a pharmaceutical composition for the prevention, treatment or amelioration of diseases which require the uptake of such a pharmaceutical composition.

In a further embodiment, the composition as described herein may be a diagnostic composition, optionally further comprising suitable means for detection, wherein said diagnostic composition has an increased in vivo and/or in vitro stability.

The compositions of the invention may be in solid or liquid form and may be, inter alia, in a form of (a) powder(s), (a) tablet(s), (a) solution(s) or (an) aerosol(s). Furthermore, it is envisaged that the medicament of the invention might comprise further biologically active agents, depending on the intended use of the pharmaceutical composition.

Administration of the suitable (pharmaceutical) compositions may be effected by different ways, e.g., by parenteral, subcutaneous, intraperitoneal, topical, intrabronchial, intrapulmonary and intranasal administration and, if desired for local treatment, intralesional administration. Parenteral administrations include intraperitoneal, intramuscular, intradermal, subcutaneous intravenous or intraarterial administration. The compositions of the invention may also be administered directly to the target site, e.g., by biolistic delivery to an external or internal target site, like a specifically effected organ.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. Suitable carriers may comprise any material which, when combined with the biologically active protein of the invention, retains the biological activity of the biologically active protein (see Remington's Pharmaceutical Sciences (1980) 16th edition, Osol, A. Ed). Preparations for parenteral administration may include sterile aqueous or non-aqueous solutions, suspensions, and emulsions). The buffers, solvents and/or excipients as employed in context of the pharmaceutical composition are preferably "physiological" as defined herein above. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles may include sodium chloride solution, Ringer's dextrose, dextrose and sodium chloride, lactated Ringer's, or fixed oils. Intravenous vehicles may include fluid and nutrient replenishes, electrolyte replenishers (such as those based on Ringer's dextrose), and the like. Preservatives and other additives may also be present including, for example, antimicrobials, anti-oxidants, chelating agents, and inert gases and the like. In addition, the pharmaceutical composition of the present invention might comprise proteinaceous carriers, like, e.g., serum albumin or immunoglobulin, preferably of human origin.

These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Pharmaceutically active matter may be present in amounts between 1 µg and 20 mg/kg body weight per dose, e.g. between 0.1 mg to 10 mg/kg body weight, e.g. between 0.5 mg to 5 mg/kg body weight. If the regimen is a continuous infusion, it should also be in the range of 1 µg to 10 mg per kilogram of body weight per minute. Yet, doses below or above the indicated exemplary ranges also are envisioned, especially considering the aforementioned factors.

Furthermore, it is envisaged that the pharmaceutical composition of the invention might comprise further biologically active agents, depending on the intended use of the pharmaceutical composition. These further biologically active agents may be e.g. antibodies, antibody fragments, hormones, growth factors, enzymes, binding molecules, cytokines, chemokines, nucleic acid molecules and drugs.

It is of note that the present invention is not limited to pharmaceutical compositions. Also compositions to be used in research or as diagnostic(s) are envisaged. It is, for example, envisaged that the biologically active proteins comprising a random coil domain as defined herein, are used in a diagnostic setting. For such a purpose, the inventive biologically active protein of this invention, comprising the herein defined "first" and "second" domain, may be detectably labelled. Such labels comprise, but are not limited to radioactive labels (like [$^3$H]hydrogen [$^{125}$I]iodide or [$^{123}$I]iodide), fluorescent labels (including but nor limiting fluorescent proteins, like green fluorescent protein (GFP) or fluorophores, like fluorescein isothiocyanate (FITC)) or NMR labels (like gadolinium chelates). The here defined labels or markers are in no way limiting and merely represent illustrative examples. The diagnostic compositions of this invention are particularly useful in tracing experiments or in a diagnostic medical setting.

In yet another embodiment, the present invention provides for a kit comprising the biologically active protein, the nucleic acid molecule encoding said biologically active protein, the vector comprising said nucleic acid molecule or the cell comprising said nucleic acid or said vector as described herein. Advantageously, the kit of the present invention further comprises, optionally (a) buffer(s), storage solutions and/or remaining reagents or materials required for the conduct of medical, scientific or diagnostic assays and purposes. Furthermore, parts of the kit of the invention can be packaged individually in vials or bottles or in combination in containers or multicontainer units.

The kit of the present invention may be advantageously used, inter alia, for carrying out the method of the invention and could be employed in a variety of applications referred herein, e.g., as diagnostic kits, as research tools or as medical tools. Additionally, the kit of the invention may contain means for detection suitable for scientific, medical and/or diagnostic purposes. The manufacture of the kits follows preferably standard procedures which are known to the person skilled in the art.

The invention is now illustrated by the following, non-limiting figures and examples.

FIGURES

FIG. 1: Gene design for the Pro-Ala-Ser#1 (PAS#1; SEQ ID NO: 18), Pro-Ala-Ser#2 (PAS#2; SEQ ID NO: 20), Pro-Ala-Ser#3 (PAS#3; SEQ ID NO: 22), (Pro-Ala-Ser#5 (PAS#5; SEQ ID NO: 26), Pro-Ala-Ser#1P2 (PAS#1P2; SEQ ID NO: 28 and Ser-Ala (piSA; SEQ ID NO: 2) polymer sequences.

(A) Nucleotide and encoded amino acid sequence of a building block for PAS#1 (SEQ ID NO: 29 and 30, respectively) obtained by hybridization of two complementary oligodeoxynucleotides, with two sticky ends (lower case letters) that are compatible with EcoO109I and SapI restriction sites.

(B) Nucleotide and encoded amino acid sequence of a building block for PAS#2 (SEQ ID NO: 31 and 32, respectively) obtained by hybridization of two complementary oligodeoxynucleotides, with two sticky ends (lower case letters) that are compatible with EcoO109I and SapI restriction sites.

(C) Nucleotide and encoded amino acid sequence of a building block for PAS#3 (SEQ ID NO: 33 and 34, respectively) obtained by hybridization of two complementary oligodeoxynucleotides, with two sticky ends (lower case letters) that are compatible with EcoO109I and SapI restriction sites.

(D) Nucleotide and encoded amino acid sequence of a building block for PAS#5 (SEQ ID NO: 35 and 36, respectively) obtained by hybridization of two complementary oligodeoxynucleotides, with two sticky ends (lower case letters) that are compatible with EcoO109I and SapI restriction sites.

(E) Nucleotide and encoded amino acid sequence of a building block for PAS#1P2 (SEQ ID NO: 39 and 40, respectively) obtained by hybridization of two complementary oligodeoxynucleotides, with two sticky ends (lower case letters) that are compatible with EcoO109I and SapI restriction sites.

(F) Nucleotide and encoded amino acid sequence of a building block for piSA (SEQ ID NO: 37 and 38, respectively) obtained by hybridization of two complementary oligodeoxynucleotides, with two sticky ends (lower case letters) that are compatible with EcoO109I and SapI restriction sites.

FIG. 2: Cloning strategy for the Pro-Ala-Ser polymer sequences as fusion to IFNa2b and IL-1ra.

(A) Nucleotide sequence stretch of pASK-2xSapI, a derivative of pASK75, used for subcloning the polymer sequence (SEQ ID NO: 55). The nucleotide sequence encodes for two SapI restriction sites in reverse complementary orientation, which leads upon digest to protruding ends that are compatible with the synthetic gene cassettes shown in FIG. 1 (indicated by bars). The recognition sequences are underlined.

(B) Nucleotide and encoded amino acid sequence (SEQ ID NO: 41 and 42, respectively) of the PAS#1 polymer with 200 residues after insertion into the pASK-2xSapI plasmid, resulting in pPAS(#1)200. The SapI restriction sites flanking the polymer sequence are labelled (recognition sequences are underlined).

(C) Nucleotide and encoded amino acid sequence (SEQ ID NO: 43 and 44, respectively) of IFNa2b after cloning on pASK-IBA4 (IBA GmbH, Göttingen). The single restriction sites KasI and HindIII used for cloning of the fusion protein as well as the single restriction site SapI for insertion of the polymer sequence are labelled (recognition sequences are underlined). The two C-terminal amino acids of the Strep-tag II are underlined. The first amino acid of the mature IFNa2b is labelled with +1.

(D) Nucleotide and encoded amino acid sequence of the N-terminus of IFNa2b after insertion of the PAS#1 polymer sequence (SEQ ID NO: 45 and 46, respectively). The single restriction sites KasI, HindIII, and SapI are labelled (recognition sequences are underlined). The first amino acid of IFNa2b as part of the fusion protein is labelled (1) and the two C-terminal amino acids of the Strep-tag II are underlined.

(E) Nucleotide and encoded amino acid sequence (SEQ ID NO: 47 and 48, respectively) of IL-1ra after cloning on pASK-IBA4 (IBA GmbH, Göttingen). The single restriction sites KasI and HindIII used for cloning of the fusion protein as well as the single restriction site SapI for insertion of the polymer sequence are labelled (recognition sequences are underlined). The two C-terminal amino acids of the Strep-tag II are underlined. The first amino acid of the mature IL-1ra is labelled with +1.

(F) Nucleotide and encoded amino acid sequence of the N-terminus of IL-1 ra after insertion of the PAS#1 polymer sequence (SEQ ID NO: 49 and 50, respectively). The single restriction sites KasI, HindIII, and SapI are labelled (recognition sequences are underlined). The first amino acid of IL1ra as part of the fusion protein is labelled (1) and the two C-terminal amino acids of the Strep-tag II are underlined.

G) Plasmid map of pPAS(#1)200-IFNa2b. The structural gene for PAS(#1)200-IFNa2b (comprising the bacterial OmpA signal peptide, the Strep-tag II, the PAS#1 polymer with 200 residues, i.e. 10 repetitive copies of the sequence shown in FIG. 1A, PAS(#1)200, and human IFNa2b) is under transcriptional control of the tetracycline promoter/operator)($tet^{p/o}$) and ends with the lipoprotein terminator ($t_{lpp}$). The plasmid backbone, i.e. outside the expression cassette flanked by the XbaI and HindIII restriction sites, is identical with that of the generic cloning and expression vector pASK75 (Skerra (1994) Gene 151:131-135). Singular restriction sites are indicated. The expression vectors for PAS(#1)400-IFNa2b and PAS(#1)600-IFNa2b are identical except that the PAS#1 polymer with 400 or 600 residues, i.e. 20 or 30 repetitive copies of the sequence shown in FIG. 1A, is encoded instead of PAS(#1)200. Similarly, the expression vectors for PAS(#2)200-IFNa2b and PAS(#3)200-IFNa2b carry a PAS#2 or PAS#3 polymer of 200, i.e. 10 repetitive copies of the sequences shown in FIGS. 1B and 1C, respectively. Similarly, the expression vectors for PAS(#5)192-IFNa2b and PAS(#5)384-IFNa2b carry a PAS#5 polymer of 192 or 384 residues, i.e. 8 or 16 repetitive copies of the sequences shown in FIG. 1D. Similarly, the expression vector for PAS(#1P2) 140-IFNa2b carries a PAS#1P2 polymer of 140 residues, i.e. 7 repetitive copies of the sequence shown in FIG. 1E. Expression vectors for PAS(#1)200-IL-1ra, PAS(#1)400-IL-1ra, PAS(#5)192-IL1ra and PAS(#5) 384-IL-1ra are similar to the corresponding vectors for IFNa2b except for carrying the coding gene for IL-1ra instead of IFNa2b.

FIG. 3: Cloning strategy for the Pro-Ala-Ser and Ser-Ala polymer sequences according to FIG. 1 as fusion to human neutrophil gelatinase-associated lipocalin, NGAL.

(A) Nucleotide and encoded amino acid sequence (SEQ ID NO: 51 and 52, respectively) of the C-terminus (underlined) of a variant of NGAL carrying the Strep-tag II (amino acid sequence in italics), cloned on the pASK75 derivative pNGAL15 (Breustedt (2006) Biochim Biophys Acta 1764:161-173). An EcoO109I restriction site was introduced at the junction of both coding regions, which leads upon digest to protruding ends that are compatible with the synthetic gene cassette (indicated by bars), yielding pNGAL15-Eco. The unique HindIII restriction site at the 3'-end of the expression cassette is labelled (recognition sequence is underlined).

(B) Nucleotide and encoded amino acid sequence (SEQ ID NO: 53 and 54, respectively) of the C-terminus of NGAL after insertion of the PAS#1 polymer sequence, followed by the Strep-tag II (italics). The unique HindIII restriction site at the 3'-end of the gene expression cassette is labelled (recognition sequence is underlined).

(C) Plasmid map of pNGAL-PAS(#1)200. The structural gene for NGAL-PAS(#1)200 (comprising the OmpA signal peptide, the modified NGAL, and PAS#1 with 200 residues, PAS(#1)200, as well as the Strep-tag II) is under transcriptional control of the tetracycline promoter/operator)($tet^{p/o}$) and ends with the lipoprotein terminator ($t_{lpp}$). The plasmid backbone, i.e. outside the expression cassette flanked by the XbaI and HindIII restriction sites, is identical with that of the generic cloning and expression vector pASK75 (Skerra (1994) Gene 151:131-135). Singular restriction sites are indicated. The expression vector for NGAL-PAS(#1)100 and NGAL-piSA100 is identical except that the PAS#1 or piSA polymer according to FIG. 1 with just 100 residues is encoded.

FIG. 4: Analysis of the purified recombinant IFNa2b, IL-1ra, and NGAL, as well as their polymer fusions by SDS-PAGE, followed by staining with Coomassie brilliant blue R-250. The recombinant proteins were produced in *E. coli* BL21 via periplasmic secretion and purified by means of the Strep-tag II using streptavidin affinity chromatography.

(A) Analysis of the purified recombinant IFNa2b and its PAS#1 fusions with 200, 400 or 600 residues, respectively, by 10% SDS-PAGE. The gel shows 2 µg protein samples each of IFNa2b, PAS(#1)200-IFNa2b, PAS(#1) 400-IFNa2b, and PAS(#1)600-IFNa2b. Samples on the left side were reduced with 2-mercaptoethanol whereas corresponding samples on the right side were left unreduced. Sizes of protein markers (kDa)—applied under reducing conditions—are indicated on the left. All four proteins appear as single homogeneous bands with apparent molecular sizes of ca. 20 kDa, ca. 80 kDa, ca. 170 kDa, and ca. 300 kDa, respectively, in the reduced form. These values are significantly larger than the calculated masses of 37.4 kDa for PAS(#1)200-IFNa2b, of 54.0 kDa for PAS(#1)400-IFNa2b, and of 70.5 kDa for PAS(#1)600-IFNa2b. This effect is clearly due to the Pro-Ala-Ser polymers with different lengths as the IFNa2b itself, with a calculated mass of 20.9 kDa, exhibits normal electrophoretic mobility. IFNa2b in the non-reduced state has a slightly higher electrophoretic mobility because of the more compact form resulting from its two intramolecular disulfide bridges.

(B) Analysis of the purified recombinant PAS(#5)192-IFNa2b and PAS(#5)384-IFNa2b by 10% SDS-PAGE. The gel shows 2 µg samples of each protein. Samples on the left side were reduced with 2-mercaptoethanol whereas corresponding samples on the right side were left unreduced. Sizes of protein markers (kDa)—applied under reducing conditions—are indicated on the left. The two proteins appear as single homogeneous bands with apparent molecular sizes of ca. 75 kDa and of ca. 120 kDa, respectively, in both the reduced and non-reduced state. This is significantly larger than the calculated masses of 36.7 kDa for PAS(#5)192-IFNa2b and of 52.6 kDa for PAS(#5)384-IFNa2b. This effect is again due to the Pro-Ala-Ser polymers with different lengths.

(C) Analysis of the purified recombinant PAS(#1)200-IFNa2b, PAS(#2)200-IFNa2b, PAS(#3)200-IFNa2b, PAS(#5)192-IFNa2b, PAS(#1P2)140-IFNa2b, and IFNa2b by 12% SDS-PAGE. The gel shows 2 µg samples of each protein reduced with 2-mercaptoethanol. Sizes of protein markers (kDa) are indicated on the left. The six proteins appear as single homogeneous bands with apparent molecular sizes of ca. 75 kDa (PAS (#1)200-IFNa2b, PAS(#2)200-IFNa2b, PAS(#3)200-IFNa2b), 70 kDa (PAS(#5)192-IFNa2b), 40 kDa (PAS (#1P2)140-IFNa2b) and of ca. 20 kDa (IFNa2b), respectively. Thus, the polymer fusions show significantly larger sizes than the calculated masses of 37.4 kDa for PAS(#1)200-IFNa2b, 37.4 kDa for PAS(#2) 200-IFNa2b, 38.6 kDa for PAS(#3)200-IFNa2b, 36.7 kDa for PAS(#5)192-IFNa2b, and 31.7 kDa for PAS (#1P2)140-IFNa2b. This effect is again due to the Pro-Ala-Ser polymers with different lengths.

(D) Analysis of the purified recombinant IL-1ra and its PAS#1 and PAS#5 fusions with 200, 400 or 192 and 384 residues, respectively, by 12% SDS-PAGE. The gel shows 2 µg protein samples each of IL-1ra, PAS(#1)200-IL-1ra, PAS(#1)400-IL-1ra, PAS(#5)192-IL-1ra and PAS(#5)384-IL-1ra reduced with 2-mercaptoethanol. Sizes of protein markers (kDa) are indicated on the left. All five proteins appear as single homogeneous bands with apparent molecular sizes of ca. 20 kDa, ca. 70 kDa, ca. 140 kDa, 66 kDa and ca. 125 kDa, respectively. For the polymer fusions these values are significantly larger than the calculated masses of 35.3 kDa for PAS(#1)200-IL-1ra, of 51.9 kDa for PAS(#1)400-IL-1ra, of 34.6 for PAS(#5)192-IL-1ra and of 50.5 kDa for PAS(#5)384-IL-1ra. This effect is clearly due to the Pro-Ala-Ser polymers with different lengths as the IL-1ra itself, with a calculated mass of 19.8 kDa, exhibits normal electrophoretic mobility.

(E) Analysis of the purified recombinant NGAL and its PAS#1 polymer fusions with 100 or 200 residues, respectively, by 12% SDS-PAGE. The gel shows 4 µg protein samples each of NGAL, NGAL-PAS(#1)100, and NGAL-PAS(#1)200. Samples on the left side were reduced with 2-mercaptoethanol whereas corresponding samples on the right side were left unreduced. Sizes of protein markers (kDa)—applied under reducing conditions—are indicated on the left. NGAL-PAS(#1)100 and NGAL-PAS(#1)200 appear as single homogeneous bands with apparent molecular sizes of ca. 45 kDa and of ca. 60 kDa, respectively, in both the reduced and non-reduced state. This is significantly larger than the calculated masses of 29.8 kDa for NGAL-PAS(#1)100 and of 38.1 kDa for NGAL-PAS(#1)200. This effect is due to the Pro-Ala-Ser polymers with different lengths as the NGAL itself, with a calculated mass of 21.5 kDa, exhibits normal electrophoretic mobility.

FIG. 5: Quantitative analysis of the hydrodynamic volumes of the purified recombinant IFNa2b, IL-1ra, NGAL, as well as their polymer fusions.

(A) Analytical gel permeation chromatography of IFNa2b, PAS(#1)200-IFNa2b, PAS(#1)400-IFNa2b, and PAS (#1)600-IFNa2b. 250 µl of each protein at a concentration of 0.25 mg/ml was applied to a Superdex S200 10/300 GL column equilibrated with phosphate-buffered saline, PBS. Absorption at 280 nm was monitored and the peak of each chromatography run was normalized to a value of 1. The arrow indicates the exclusion volume of the column (8.0 ml).

(B) Analytical gel permeation chromatography of PAS(#5) 192-IFNa2b and PAS(#5)384-IFNa2b. 250 µl of the protein at a concentration of 0.25 mg/ml was applied to a Superdex S200 10/300 GL column equilibrated with PBS buffer. Absorption at 280 nm was monitored and the peak of each chromatography run was normalized to a value of 1. The arrow indicates the exclusion volumes of the column (8.0 ml).

(C) Calibration curve for the chromatograms from (A) and (B) using Superdex S200 10/300 GL. The logarithm of the molecular weight (MW) of marker proteins (RNase A, 13.7 kDa; carbonic anhydrase, 29.0 kDa; ovalbumin, 43.0 kDa; bovine serum albumin, 66.3 kDa; transferrin, 81.0 kDa; alcohol dehydrogenase, 150 kDa) was plotted vs. their elution volumes (black circles) and fitted by a straight line. From the observed elution volumes of IFNa2b and its fusion proteins (black squares) their apparent molecular weights were determined as follows: IFNa2b: 22.5 kDa (calculated: 20.9 kDa); PAS(#1)200-IFNa2b: 176 kDa (calculated: 37.4 kDa); PAS(#1)400-IFNa2b: 346 kDa (calculated: 54.0 kDa); PAS(#1)600-IFNa2b: 522 kDa (calculated: 70.5 kDa); PAS(#5)192-IFNa2b: 162 kDa (calculated: 36.7 kDa); PAS(#5)384-IFNa2b: 280 kDa (calculated: 52.6 kDa).

(D) Analytical gel permeation chromatography of PAS(#2) 200-IFNa2b, PAS(#3)200-IFNa2b, and PAS(#1P2)140-

IFNa2b. 250 μl of each protein at a concentration of 0.25 mg/ml was applied to a Superdex S200 10/300 GL column equilibrated with phosphate-buffered saline, PBS. Absorption at 280 nm was monitored and the peak of each chromatography run was normalized to a value of 1. The arrow indicates the exclusion volume of the column ($V_0$=8.0 ml).

(E) Calibration curve for the chromatograms from (D) using the same Superdex S200 10/300 GL column. The logarithm of the molecular weight (MW) of marker proteins (RNase A, 13.7 kDa; carbonic anhydrase, 29.0 kDa; ovalbumin, 43.0 kDa; bovine serum albumin, 66.3 kDa; transferrin, 81.0 kDa; alcohol dehydrogenase, 150 kDa) was plotted vs. their elution volumes (black circles) and fitted by a straight line. From the observed elution volumes of IFNa2b and its fusion proteins (black squares) their apparent molecular sizes were determined as follows: PAS(#2)200-IFNa2b: 168 kDa (calculated: 37.4 kDa); PAS(#3)200-IFNa2b: 146 kDa (calculated: 38.6 kDa); PAS(#1P2)140-IFNa2b: 66.4 kDa (calculated: 31.7 kDa).

(F) Analytical gel permeation chromatography of IL-1ra, PAS(#1)200-IL-1ra, PAS(#1)400-IL-1ra, PAS(#5)192-IL-1ra, and PAS(#5)384-IL-1ra. 250 μl of each protein at a concentration of 0.25 mg/ml was applied to a Superdex S200 10/300 GL column equilibrated with phosphate-buffered saline, PBS. Absorption at 280 nm was monitored and the peak of each chromatography run was normalized to a value of 1. The arrow indicates the exclusion volume of the column. For better clarity only the peaks are shown.

(G) Calibration curve for the chromatograms from (F) using the same Superdex S200 10/300 GL column. The logarithm of the molecular weight (MW) of marker proteins (RNase A, 13.7 kDa; carbonic anhydrase, 29.0 kDa; ovalbumin, 43.0 kDa; bovine serum albumin, 66.3 kDa; transferrin, 81.0 kDa; alcohol dehydrogenase, 150 kDa) was plotted vs. their elution volumes (black circles) and fitted by a straight line. From the observed elution volumes of IL-1ra and its fusion proteins (black squares) their apparent molecular sizes were determined as follows: IL-1ra: 19.8 kDa (calculated: 18.8 kDa); PAS(#1)200-IL-1ra: 161 kDa (calculated: 35.3 kDa); PAS(#1)400-IL-1ra: 336 kDa (calculated: 51.9 kDa); PAS(#5)192-IL-1ra: 148 kDa (calculated: 34.6 kDa); PAS(#5)384-IL-1ra: 305 kDa (calculated: 50.5 kDa).

(H) Analytical gel permeation chromatography of NGAL, NGAL-PAS(#1)100, NGAL-PAS(#1)200 and NGAL-piSA100. 250 μl of each protein at a concentration of 0.25 mg/ml was applied to either a Superdex S75 10/300 GL (NGAL and NGAL-piSA100) or a Superdex S200 10/300 GL (NGAL-PAS(#1)100 and NGAL-PAS(#1)200) column equilibrated with PBS buffer. Absorption at 280 nm was monitored and the peak of each chromatography run was normalized to a value of 1. The arrow indicates the exclusion volumes of the columns (7.5 ml and 8.2 ml, respectively).

(I) Calibration curves for the chromatograms from (H) using Superdex S75 10/300 GL and Superdex S200 10/300 GL. The logarithm of the molecular weight (MW) of marker proteins (Superdex S75 10/300 GL: aprotinin, 6.5 kDa; ribonuclease, 13.7 kDa; myoglobin, 17.6 kDa; carbonic anhydrase, 29.0 kDa; ovalbumin, 43.0 kDa; bovine serum albumin, 66.3 kDa; transferrin, 81.0 kDa; alcohol dehydrogenase, 150 kDa) was plotted vs. their elution volumes (black circles) and fitted by a straight line. From the observed elution volumes of NGAL and its fusion proteins (black squares) their apparent molecular weights were determined as follows: NGAL: 21.5 kDa (calculated: 21.5 kDa); NGAL-PAS(#1)100: 72.6 kDa (calculated: 29.8 kDa); NGAL-PAS(#1)200: 106.4 kDa (calculated: 38.1 kDa); NGAL-piSA100: 54 kDa (calculated: 29.4 kDa).

FIG. 6: Experimental secondary structure analysis of the purified recombinant IFNa2b, IL-1ra, NGAL, as well as their polymer fusions by circular dichroism (CD) spectroscopy. Spectra were recorded at room temperature in 50 mM $K_2SO_4$, 20 mM K-phosphate pH 7.5 and normalized to the molar ellipticity, $\Theta_M$, for each protein.

(A) Circular dichroism (CD) spectra of the purified recombinant IFNa2b, PAS(#1)200-IFNa2b, PAS(#1)400-IFNa2b, and PAS(#1)600-IFNa2b. The CD spectrum for IFNa2b shows the typical features of a predominant α-helix protein with two negative maxima around 208 nm and 220 nm (Sreerama in: Circular Dichroism—Principles and Applications (2000) Berova, Nakanishi and Woody (Eds.) Wiley, New York: 601-620 which indicates the correct folding of the bacterially produced human IFNa2b. The spectra of its fusion proteins with the Pro-Ala-Ser polymer reveal characteristic deviations with a dominant negative minimum around 205 nm, which is clearly indicative of random coil conformation. In addition, there is a shoulder around 220 nm, which results from the α-helical contribution of IFNa2b and indicates the correct folding of the IFNa2b even as part of the fusion protein.

(B) Molar difference CD spectra for PAS(#1)200-IFNa2b, PAS(#1)400-IFNa2b, and PAS(#1)600-IFNa2b obtained by subtraction of the spectrum for IFNa2b from that of the respective fusion protein. The difference CD spectra for the PAS#1 polymers with 200, 400, and 600 residues all reveal a strong around 200 nm, which is a clear indication of their random coil conformation in the buffered aqueous solution (Greenfield (1969) Biochemistry 8: 4108-4116; Sreerama (2000) loc. cit.; Fändrich (2002) EMBO J. 21:5682-5690.

(C) Circular dichroism (CD) spectra of the purified recombinant PAS(#2)200-IFNa2b, PAS(#3)200-IFNa2b and PAS(#1P2)140-IFNa2b, together with the one of IFNa2b. The spectra of the polymer fusion proteins reveal a dominant negative minimum around 205 nm, which is indicative of random coil conformation, and a shoulder around 220 nm, which results from the contribution of the correctly folded IFNa2b.

(D) Molar difference CD spectra for PAS(#2)200-IFNa2b, PAS(#3)200-IFNa2b and PAS(#1P2)140-IFNa2b after subtraction of the spectrum for IFNa2b. The difference CD spectra for the PAS#2 and PAS#3 polymers, each with 200 residues, and the PAS#1P2 polymer, with 140 residues, reveal a significant minimum around 200 nm, which is a clear indication of random coil conformation (Greenfield (1969) loc. cit.; Sreerama (2000) loc. cit.; Fändrich (2002) loc. cit.)

(E) Circular dichroism (CD) spectra of the purified recombinant PAS(#5)192-IFNa2b and PAS(#5)384-IFNa2b. The spectra of these two fusion proteins reveal a dominant negative minimum around 205 nm, which is indicative of random coil conformation, and a shoulder around 220 nm, which results from the contribution of the folded IFNa2b.

(F) Molar difference CD spectra for PAS(#5)192-IFNa2b and PAS(#5)384-IFNa2b after subtraction of the spectrum for IFNa2b. The difference CD spectra for the PAS#5 polymer with 192 and 384 residues reveal a strong minimum around 200 nm, which is a clear indication of random coil conformation (Greenfield (1969) loc. cit.; Sreerama (2000) loc. cit.; Fändrich (2002) loc. cit.)

(G) Circular dichroism (CD) spectra of the purified recombinant IL-1 ra, PAS(#1)200-IL1ra, PAS(#1)400-IL1ra, PAS(#5)192-IL1ra, and PAS(#5)384-IL1ra. The spectra of the four fusion proteins reveal a dominant negative minimum around 200 nm, which is indicative of random coil conformation.

(H) Molar difference CD spectra for PAS(#1)200-IL-1ra, PAS(#1)400-IL-1ra, PAS(#5)192-IL1ra, and PAS(#5) 384-IL-1ra after subtraction of the spectrum for IL-1ra. The difference CD spectra for both the PAS#1 and the PAS#5 polymer with 200 or 400 and 192 or 384 residues, respectively, reveal a strong minimum around 200 nm, which is a clear indication of random coil conformation (Greenfield (1969) loc. cit.; Sreerama (2000) loc. cit.; Fändrich (2002) loc. cit.).

(I) CD spectra of the purified recombinant NGAL, NGAL-PAS(#1)100, and NGAL-PAS(#1)200. The CD spectrum for NGAL has the typical feature of a predominant n-sheet protein with a negative maximum around 212 nm (Sreerama (2000) loc. cit.). The absence of the positive band below 200 nm is in agreement with the CD spectrum of its mouse ortholog 24p3 (Chu (1998) J Pept Res 52:390-397). Taken together, these data support the correct fold of the bacterially produced human NGAL protein. The spectra of the two fusion proteins reveal characteristic deviations with a dominant negative minimum around 195 nm, which is indicative of random coil conformation, and a shoulder around 200 nm, which results from the contribution of NGAL with its negative minimum at 200 nm. The latter observation indicates the correct folding of the NGAL protein when fused with the Pro-Ala-Ser polymer.

(J) Molar difference CD spectra for NGAL-PAS(#1)100 and NGAL-PAS(#1)200 after subtraction of the spectrum for NGAL. The difference CD spectra for the PAS#1 polymer with 100 and 200 residues reveal a strong minimum around 200 nm, which is a clear indication of random coil conformation (Greenfield (1969) loc. cit.; Sreerama (2000) loc. cit.; Fändrich (2002) loc. cit.).

(K) CD spectra of the purified recombinant NGAL-piSA100 and its molar difference CD spectrum after subtraction of the spectrum for NGAL. Both the CD spectrum for NGAL-piSA100 and the difference CD spectrum for the piSA100 polymer has the typical feature of a predominant β-sheet protein with a negative maximum around 218 nm and a positive maximum below 200 nm (Sreerama (2000) loc. cit.). Thus, the difference spectrum is clearly different from those of the Pro-Ala-Ser polymer fusions with comparable length, which are clearly dominated by random coil conformation attributable to the polymer fusion partner.

FIG. 7: Test of serum stability of PAS(#1)200-IFNa2b and PAS(#5)192-IFNa2b

Serum stability of PAS(#1)200-IFNa2b (A) and PAS(#5) 192-IFNa2b (B) was analyzed by incubation of the fusion protein at a concentration of 0.17 mg/ml in 83% v/v mouse plasma (Rockland Immunochemicals, Gilbertsville, Pa.) at 37° C. for up to 48 h. Samples (6 μl) were taken at indicated time points and diluted with 54 μl SDS-PAGE electrophoresis buffer and 15 μl SDS-PAGE loading buffer containing β-mercaptoethanol. Aliquots of 25 μl (corresponding to 0.33 μg test protein) and a reference sample (0.1 μg) were applied to a 12% SDS-PAGE and blotted onto a nitrocellulose membrane. The recombinant proteins were detected by incubation with StrepTactin® Alkaline Phosphatase conjugate (IBA, Göttingen, Germany), which recognizes the Strep-tag II, and developed via chromogenic reaction.

For both test proteins the blots reveal signals of constant intensity for all time points. No degradation products could be detected and there was no indication of protein aggregation, which would lead to a decrease of the test protein concentration, over the time course investigated.

Figure 8:
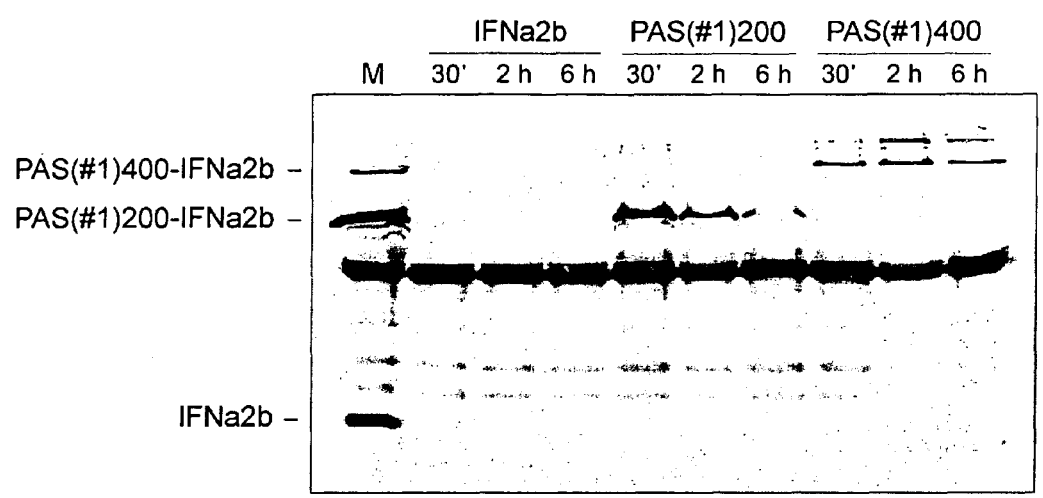

FIG. 8: Pharmacokinetics of the purified recombinant IFNa2b and its PAS#1 polymer fusions with 200 or 400 residues.

BALB/c mice with body weights around 25 g received injections of ca. 125 μl of either IFNa2b, PAS(#1)200-IFNa2b, or PAS(#1)400-IFNa2b protein with a concentration of 1 mg/ml in PBS containing 1 mM EDTA to achieve a dose of 5 mg test protein per kg body weight (b.w.). Blood samples were taken as indicated. Aliquots of the cleared plasma samples were diluted 1:5 with PBS. Aliquots of 10 μl of the diluted sample (corresponding to 1 μl plasma), were applied to a 12% SDS-PAGE and blotted onto a nitrocellulose membrane. The recombinant proteins were detected by incubation with the mouse anti-human IFNa2b antibody 9D3 (Abcam, Cambridge, UK) followed by incubation with an anti-mouse IgG alkaline phosphatase conjugate (Sigma-Aldrich, St. Louis, Mo.) and developed in a chromogenic reaction.

The leftmost lane (M) shows a mixture of purified IFNa2b, PAS(#1)200-IFNa2b, and PAS(#1)400-IFNa2b (each 0.1 μg, i.e. an amount as expected for t=0 in the plasma samples) as reference. The other lanes show plasma samples for IFNa2b, PAS(#1)200-IFNa2b, and PAS(#1) 400-IFNa2b at time points as indicated.

The blot reveals the highest signals for all three protein samples at the earliest time point, i.e. after 30 min, revealing already a rapid decay of the IFNa2b, which is no longer detectable after 2 h. In contrast, both PAS(#1) 200-IFNa2b and PAS(#1)400-IFNa2b are detectable for up to 6 h, with a obviously stronger retention for the 400 residue fusion compared with the 200 residue fusion, indicating significantly prolonged circulation when compared to the unfused IFNa2b protein. Notably, there was no indication of proteolytic degradation for either protein sample. Thus, not only the IFNa2b protein of interest but also the polymer fusion moiety reveal high serum stability.

Figure 9:
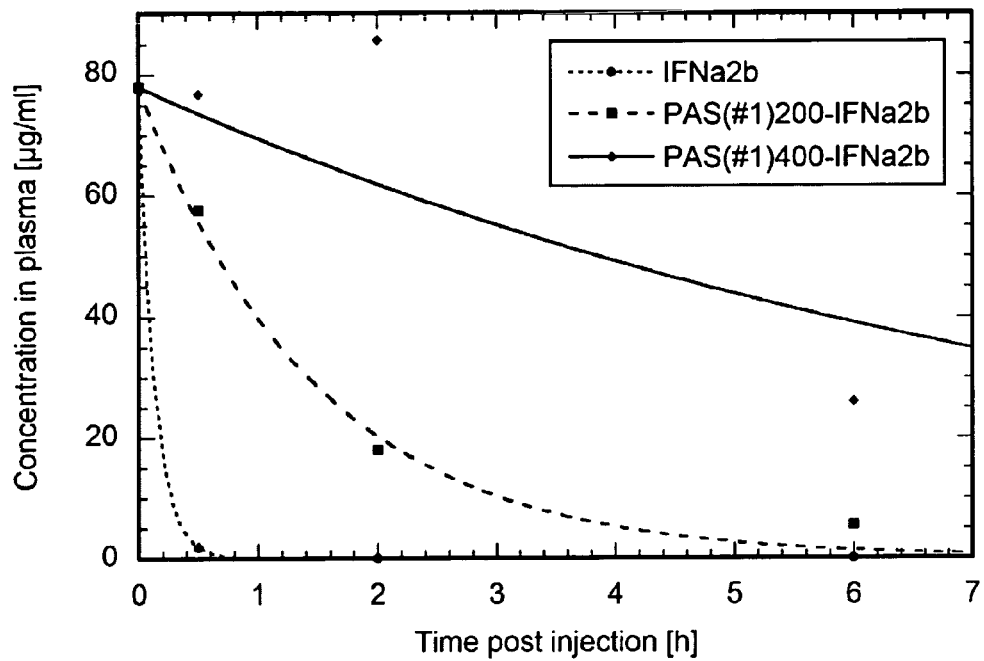

FIG. 9: Quantitative analysis of the pharmacokinetics of the purified recombinant IFNa2b and its PAS#1 polymer fusion with 200 and 400 residues.

Plasma samples from the same animals as investigated in FIG. 8 were quantitatively assayed for IFNa2b, PAS(#1) 200-IFNa2b or PAS(#1)400-IFNa2b concentrations using a sandwich ELISA. Therefore, the wells of a microtitre plate were coated with the anti-human IFNa antibody 9D3 (Abcam, Cambridge, UK) as capture antibody and dilution series of the plasma samples from animals of group A (injection of IFNa2b), group B (injection of PAS(#1)200-IFNa2b), and group C (injection of PAS(#1)400-IFNa2b) were applied. Bound IFNa2b, PAS(#1)200-IFNa2b, and PAS(#1)400-IFNa2b were detected with a second anti-human IFNa2b antibody HRP conjugate (4E10-HRP; Abcam, Cambridge, UK), which recognizes a different epitope than the capture antibody, followed by chromogenic reaction. Concentrations of IFNa2b, PAS(#1)200-IFNa2b, and PAS(#1) 400-IFNa2b were quantified by comparison with standard curves prepared with the same purified recombinant proteins applied at a known concentration. To estimate the plasma half-life of IFNa2b, PAS(#1) 200-IFNa2b, and PAS(#1)400-IFNa2b, the obtained concentration values were plotted against time post intravenous injection and numerically fitted assuming a mono-exponential decay.

As result, the unfused IFNa2b protein exhibited a very fast clearance with a half-life of $5.5 \pm 1 \times 10^{-5}$ min. In contrast, the elimination phase determined for PAS(#1)200-IFNa2b and PAS(#1)400-IFNa2b were significantly retarded, with half-lifes of $61.7 \pm 5.4$ min and ca. $6 \pm 3$ h, respectively, thus demonstrating a more than ten-fold and 60-fold prolonged circulation due to the Pro-Ala-Ser polymer fusion with 200 and 400 residues, respectively, compared with the unfused IFNa2b.

Figure 10:
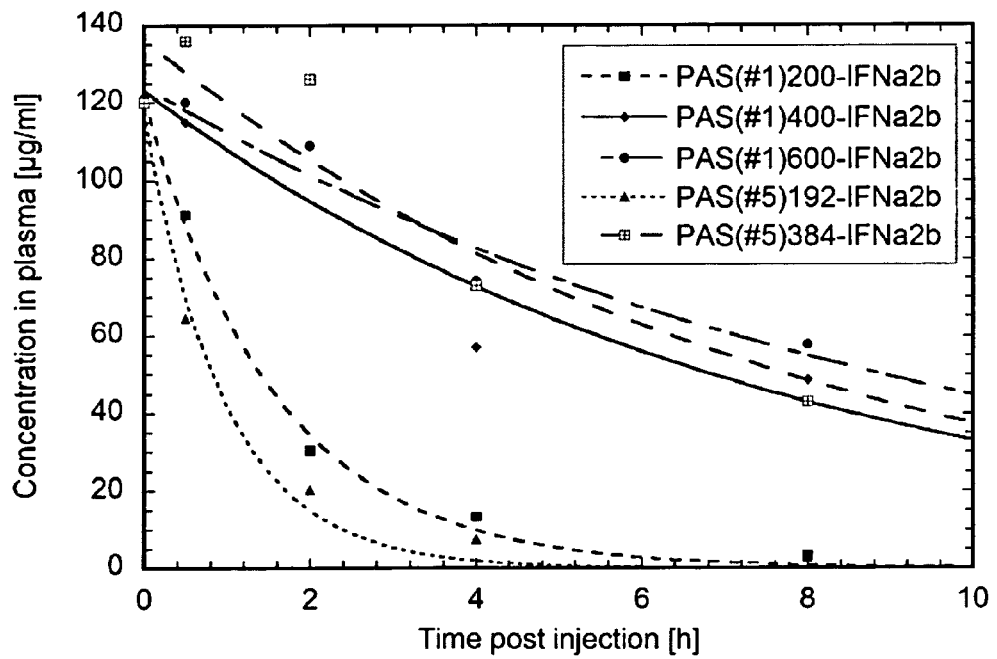

FIG. 10: Quantitative analysis of the pharmacokinetics of the purified recombinant IFNa2b PAS#1 polymer fusions with 200, 400, 600 residues and PAS#5 polymer fusions with 192 and 384 residues, respectively.

C57BL/6 mice with body weights around 18 g received injections of ca. 125 µl of either PAS(#1)200-IFNa2b, PAS(#1)400-IFNa2b, PAS(#1)600-IFNa2b, PAS(#5)-IFNa2b or PAS(#5)384-IFNa2b protein with a concentration of 1 mg/ml in PBS containing 1 mM EDTA to achieve a dose of 7 mg test protein per kg body weight (b.w.). Blood samples were taken after 30 min, 240 min, 360 min, and 480 min. Plasma samples were quantitatively assayed for IFNa2b, PAS(#1)200-IFNa2b or PAS(#1)400-IFNa2b using a sandwich ELISA. To estimate the plasma half-life of PAS(#1)200-IFNa2b, PAS(#1) 400-IFNa2b, PAS(#1)600-IFNa2b, PAS(#5)192-IFNa2b, and PAS(#5)384-IFNa2b, the obtained concentration values were plotted against time post intravenous injection and numerically fitted assuming a mono-exponential decay.

As result, the elimination phase determined for PAS(#1) 200-IFNa2b, PAS(#1)400-IFNa2b, and PAS(#1)600-IFNa2b were significantly retarded, with half-lifes of $66.2 \pm 5.6$ min, $316.1 \pm 76.8$ min, and ca. $406.8 \pm 60$ min, respectively, thus demonstrating a more than 10-fold, 60-fold and 70-fold prolonged circulation due to the Pro-Ala-Ser polymer fusion with 200, 400 and 600 residues, respectively, compared with the unfused IFNa2b (FIG. 9). Similarly, the elimination phase determined for PAS(#5)192-IFNa2b and PAS(#5)384-IFNa2b were significantly retarded, with half-lifes of $40.4 \pm 5.6$ min and ca. $321 \pm 93.6$ min, respectively, thus demonstrating a more than 7-fold and 60-fold prolonged circulation due to the Pro-Ala-Ser polymer fusion with 192 and 384 residues, respectively, compared with the unfused IFNa2b (FIG. 9).

FIG. 11: Pharmacokinetics of the purified recombinant NGAL and its PAS#1 polymer fusions with 100 or 200 residues.

Female Wistar rats with body weights around 210 g received injections of ca. 1050 µl of either NGAL, NGAL-PAS(#1)100, or NGAL-PAS(#1)200 protein with a concentration of 1 mg/ml in PBS to achieve a dose of 5 mg test protein per kg body weight (b.w.). Blood samples were taken as indicated. Aliquots of the cleared plasma samples were diluted 1:5 with PBS. Three aliquots of 1.25 µl of the diluted sample (corresponding to 0.25 µl plasma) from animals each injected with one of the three different proteins were mixed and applied to a 12% SDS-PAGE and blotted onto a nitrocellulose membrane. The recombinant proteins were detected by incubation with StrepTactin® Alkaline Phosphatase conjugate (IBA, Göttingen, Germany), which recognizes the Strep-tag II, and developed in a chromogenic reaction.

FIGS. 11A and 11B depict two time series with independent plasma samples of different animals from group A (injection of NGAL), group B (injection of NGAL-PAS(#1) 100), and group C (injection of NGAL-PAS(#1)200). The leftmost lanes in FIGS. 11A and 11B show the molecular size standard (with marker sizes on the left), the following lanes show mixtures of the three plasma samples containing NGAL, NGAL-PAS(#1)100, and NGAL-PAS(#1)200 at time points indicated, and the rightmost lane shows a mixture of purified NGAL, NGAL-PAS(#1)100, and NGAL-PAS(#1) 200 (each 0.1 µg) as reference.

The blots reveal the highest signals for all three protein samples at the earliest time point, i.e. after 5 min, with a rapid decay of the NGAL, which is no longer detectable after 30 min. In contrast, both NGAL-PAS(#1)100 and NGAL-PAS(#1)200 are detectable for much longer periods, with a slightly stronger effect for the 200 residue fusion compared with the 100 residue fusion, indicating significantly prolonged circulation when compared to the unfused NGAL protein. Notably, there was no indication of proteolytic degradation for either protein sample. Thus not only the NGAL protein of interest but also the polymer fusion moiety reveal high serum stability. Finally, none of the animals showed any signs of acute toxicity or inflammation, demonstrating high tolerance for the fusion proteins according to this invention.

Figure 12:
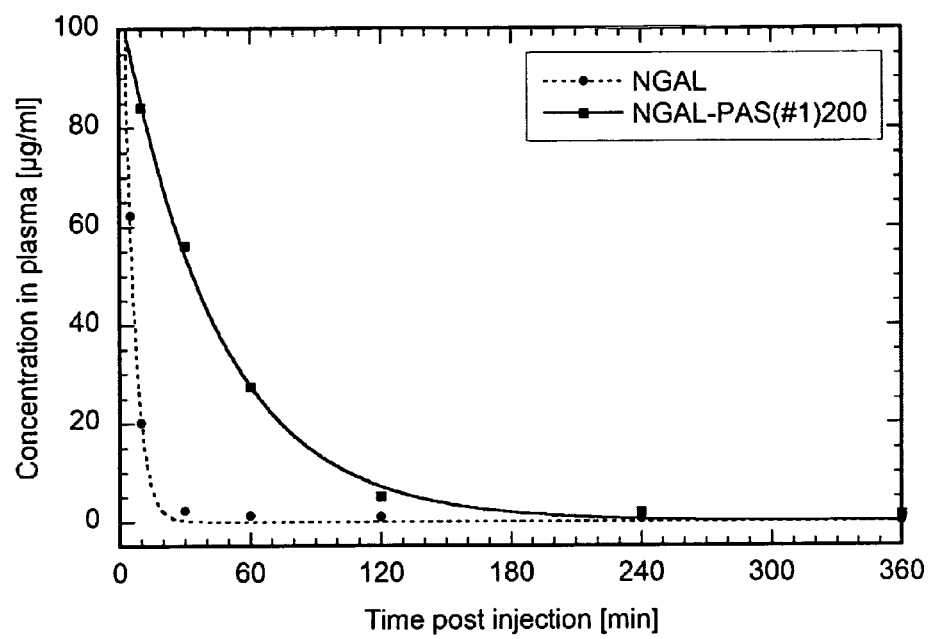

FIG. 12: Quantitative analysis of the pharmacokinetics of the purified recombinant NGAL and its PAS#1 polymer fusion with 200 residues.

Plasma samples from the same animals as investigated in FIG. 11A were assayed for NGAL or NGAL-PAS(#1) 200 concentrations using a sandwich ELISA. Therefore, the wells of a microtitre plate were coated with an anti-human Lipocalin-2/NGAL antibody (R&D Systems, Minneapolis, Minn.) as capture antibody and dilution series of the plasma samples from animals of group A (injection of NGAL) or group C (injection of NGAL-PAS(#1)200) were applied. Bound NGAL and NGAL-PAS(#1)200 were detected with StrepTactin® Alkaline Phosphatase conjugate, which recognizes the Strep-tag II, followed by chromogenic reaction. Concentrations of NGAL and NGAL-PAS(#1)200 were quantified by comparison with a standard curve prepared with the same purified recombinant proteins applied at a known concentration. To estimate the plasma half-life of NGAL and NGAL-PAS(#1)200, the experimental concentration values were plotted against time post intravenous injection and numerically fitted assuming a mono-exponential decay, whereby for better clarity only data points till 360 min are depicted.

The unfused NGAL protein exhibited a very fast clearance with a half-life of $3.1 \pm 0.2$ min. According to the principles of allometric scaling (Mahmood (2005) Interspecies Pharmacokinetic Scaling: Principles and Application of Allometric Scaling. Pine House Publishers, Rockville, Md.) this value is in agreement with the half-life of 10 min described for the monomeric form of the natural NGAL in humans (Axelsson (1995) Scand J Clin Lab Invest 55:577-588), which indicates a mechanism of cellular uptake that may be unique to this particular protein. Recently, it could be shown that megalin, a member of the low-density lipoprotein receptor, may act as a receptor for NGAL in kidney epithelial cells and mediate its uptake (Hvidberg (2005) FEBS Lett 579: 773-777).

In contrast, the elimination phase determined for NGAL-PAS(#1)200 was significantly slower, with a terminal half-life of 30.9±1.3 min, thus demonstrating a ten-fold prolonged circulation due to the Pro-Ala-Ser polymer fusion with 200 residues compared with the unfused NGAL. The retarding effect on the plasma half-life may be even more pronounced for a protein of interest that is not subject to a specific clearance mechanism as it is obviously the case for NGAL.

Figure 13:
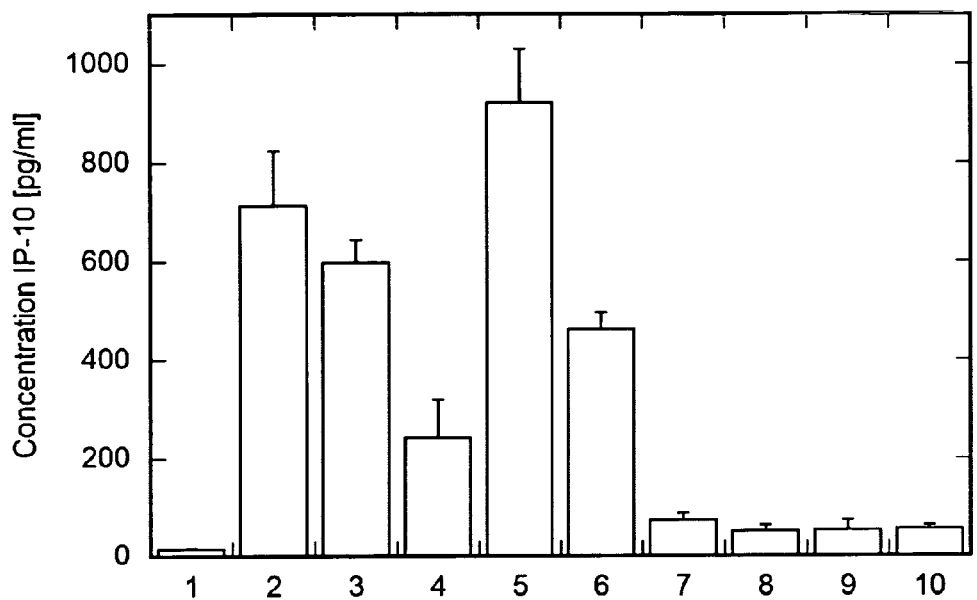

FIG. 13: Comparative activity analysis of the commercially available IntronA (Schering, Kenilworth, N.J.), recombinant PAS(#1)200-IFNa2b, and a recombinant Fab fragment (serving as negative control) by IP-10 ELISA. $2 \times 10^5$ human peripheral blood mononuclear cells (PBMCs) were incubated with IntronA, PAS(#1)200-IFNa2b or a Fab fragment, which was similarly prepared as PAS(#1)200-IFNa2b, at different concentrations. The specific activity of IntronA was $2.6 \times 10^8$ U/mg according to the data sheet of the manufacturer. Induced IP-10 protein was quantified by the human IP-10 ELISA Set (BD OptEIA™, BD Biosciences Pharmingen, USA). IntronA and PAS(#1)200-IFNa2b induce the release of IP-10 in a concentration-dependent manner with similar effects. The unstimulated as well as the PBMCs treated with the Fab fragment did not show any significant IP-10 production.

FIG. 14: Theoretical prediction of secondary structure for the Pro-Ala-Ser and Ser-Ala polymer sequences according to the Chou-Fasman method (Chou and Fasman (1974) Biochemistry 13: 222-245). This illustration shows the output from the CHOFAS computer algorithm as implemented on the Sequence Comparison and Secondary Structure prediction server at the University of Virginia (URL: http://fasta.bioch.virginia.edu/fasta_www2). To avoid boundary effects at the amino and carboxy termini each amino acid sequence block according to FIG. 1 was pasted in three repeated copies and only the output for the central block (boxed) was considered. In the case of the piSA polymer sequence (SEQ ID NO: 56) the Chou-Fasman algorithm predicts α-helical secondary structure for 20 of 20 residues, i.e. 100%. This is in clear contrast with the experimentally observed predominant β-sheet conformation for this polymer sequence as part of a fusion protein (see FIG. 6). In the case of the PAS#1 polymer sequence (SEQ ID NO: 57) the Chou-Fasman algorithm predicts α-helical secondary structure for 12 of 20 residues, i.e. 60%. This is in contrast with the experimentally observed predominant random coil conformation for this polymer sequence as part of a fusion protein (see FIG. 6). In the case of the PAS#5 polymer sequence (SEQ ID NO: 58) the Chou-Fasman algorithm predicts α-helical secondary structure for 20 of 24 residues, i.e. 83.3%. Again, this is in clear contrast with the experimentally observed predominant random coil conformation for this polymer sequence as part of a fusion protein (see FIG. 6).

EXAMPLES

The present invention is additionally described by way of the following illustrative non-limiting examples that provide a better understanding of the present invention and of its many advantages.

Unless otherwise indicated, established methods of recombinant gene technology were used as described, for example, in Sambrook, Russell "Molecular Cloning, A Laboratory Manual", Cold Spring Harbor Laboratory, N.Y. (2001).

The following examples illustrate the invention:

Example 1

Gene Synthesis for Pro-Ala-Ser and Ser-Ala Amino Acid Polymers

As described herein above, amino acid repeats consisting of Pro, Ala, and Ser residues are depicted herein as "PAS" (formerly also known as "APS"). Gene fragments encoding a repetitive polymer sequence comprising Pro, Ala, and Ser residues (PAS#1 which corresponds to SEQ ID NO: 18, PAS#2 which corresponds to SEQ ID NO: 20, PAS#3 which corresponds to SEQ ID NO: 22, PAS#5 which corresponds to SEQ ID NO: 26, and PAS#1P2 which corresponds to SEQ ID NO: 28) or Ser and Ala (piSA which corresponds to SEQ ID NO: 2) were obtained by hybridisation and ligation of the two complementary oligodeoxynucleotides shown in FIG. 1A-F using concatamer formation in a directed manner, taking advantage of their mutually compatible but non-palindromic sticky ends. Oligodeoxynucleotides were purchased from IBA (Göttingen, Germany) and purified by preparative urea polyacrylamide gel electrophoresis. The amino acid sequences depicted in SEQ ID NOs 30, 32, 34, 36, 38 and 40 represent cloning versions of SEQ ID NOs 18, 20, 22, 26, 2 and 28, respectively, comprising an additional alanine. Correspondingly, the nucleic acid sequences depicted in SEQ ID NOs 29, 31, 33, 35, 37 and 39 (encoding the amino acids as shown in SEQ ID NOs 30, 32, 34, 36, 38 and 40) comprise an additional egg codon for alanine, which becomes eliminated upon ligation via sticky ends. Enzymatic phosphorylation was performed by mixing 200 pmol of both oligodeoxynucleotides in 100 µl 150 mM Tris/HCl pH 7.6, 10 mM MgCl$_2$, 5 mM DTT, 1 mM ATP and incubation for 30 min at 37° C. in the presence of 10 u polynucleotide kinase (MBI Fermentas, St. Leon-Rot, Germany). After denaturation for 10 min at 80° C., the mixture was cooled to room temperature overnight to achieve hybridization. Then 50 µl of this solution was ligated by adding 1 u T4 DNA ligase (MBI Fermentas) and 10 µl 100 mM Tris/HCl pH 7.4, 50 mM MgCl$_2$, 20 mM DTT, 10 mM ATP, and in some cases 5 mM of each dATP, dCTP, dGTP, and dTTP, in a total volume of 100 µl and incubation for 50 min on ice. After 10 min heat inactivation at 70° C. the ligation products were separated by 1% (w/v) agarose gel electrophoresis in the presence of TAE buffer (40 mM Tris, 20 mM acetic acid, 1 mM EDTA). After staining with ethidium bromide the band corresponding to the assembled gene segment of 300 bp (piSA), 420 bp (PAS#1P2), 576 bp (PAS#5), and 600 bp (PAS#1, 2, 3) length was excised and isolated by means of phenol extraction.

Example 2

Construction of Expression Vectors for PAS#1, PAS#2, PAS#3, PAS#5, and PAS#1P2 Fusion Proteins of Interferon α-2b (IFNa2b)

For cloning of the synthetic gene fragment coding for PAS#1, PAS#2, PAS#3, PAS#1P2, and PAS#5 from Example 1a derivative of pASK75 (Skerra, A. (1994) Gene 151:131-135), pASK-2xSapI, harboring a nucleotide sequence with two SapI restriction sites in reverse complementary orientation (FIG. 2A), was employed. This vector was cut with SapI, dephosphorylated with shrimp alkaline phosphatase (USB, Cleveland, Ohio), and ligated with the synthetic DNA fragment (FIG. 2B). Resulting intermediate plasmids were designated pPAS(#1)200, pPAS(#2)200, pPAS(#3)200, pPAS (#5)192, and pPAS(#1P2)140.

After transformation of *E. coli* XL1-Blue (Bullock (1987) Biotechniques 5: 376-378), plasmids were prepared and the sequences of the cloned synthetic nucleic acid inserts were confirmed by restriction analysis and automated double-stranded DNA sequencing (ABI-Prism™310 Genetic analyzer, Perkin-Elmer Applied Biosystems, Weiterstadt, Germany) using the BigDye™ terminator kit as well as oligodeoxynucleotide primers that enabled sequencing from both sides. The resulting plasmid harboring the ca. 200 residue polymer sequence served as an intermediate vector, which enabled the simple further subcloning of the polymer sequence insert.

The coding gene for IFNa2b was amplified from the plasmid IRAMp995M1713Q (RZPD, Berlin, Germany) carrying the corresponding cDNA using the oligodeoxynucleotides 5'-TCTGTGGGCGCCA GCTCTTCTGCCTGTGATCTGCCTCAAACCCAC (SEQ ID NO: 59) and 5'-GAACCA AAGCTTATTCCTTACTTCTTAAAC (SEQ ID NO: 60) as primers. The first primer contains a KasI restriction site at the 5'-end, followed by a SapI restriction site (underlined), whereas the second primer contains a HindIII restriction site (underlined). The amplification product was purified and digested with KasI and HindIII and ligated with the accordingly cut vector pASK-IBA4 (IBA, Göttingen, Germany). After transformation of *E. coli* XL1-Blue, plasmids were prepared and the sequences of the cloned synthetic nucleic acid inserts were confirmed by restriction analysis and automated double-stranded DNA sequencing. The plasmid coding for IFNa2b as fusion with a N-terminal Strep-tag II was designated pASK-IFNa2b (FIG. 2C).

For the construction of expression plasmids encoding IFNa2b as fusion with PAS(#1)200, PAS(#1)400, and PAS (#1)600, pASK-IFNa2b was cut with SapI, dephosphorylated with shrimp alkaline phosphatase, and ligated with an excess of the gene fragment for the 200 residue polymer isolated from the intermediate plasmid pPAS(#1)200 by restriction digest with SapI (FIG. 2D). After transformation of *E. coli* JM83 (Yanisch-Perron. (1985) Gene 33:103-119), plasmids were prepared and the sizes of the polymer encoding insert were confirmed by restriction analysis. The plasmids coding for IFNa2b carrying a 200, 400 and 600 residue polymer sequence, i.e. PAS(#1)200-IFNa2b, PAS(#1)400-IFNa2b, and PAS(#1)600-IFNa2b, were designated pASK-PAS(#1) 200-IFNa2b (FIG. 2G), pASK-PAS(#1)400-IFNa2b, and pASK-PAS(#1)600-IFNa2b, respectively. The plasmids coding for PAS(#2)200-IFNa2b, PAS(#3)200-IFNa2b, PAS (#1P2)140-IFNa2b, PAS(#5)192-IFNa2b, and PAS(#5)384-IFNa2b were constructed in a similar manner using the appropriate corresponding gene cassette encoding each of the amino acid polymer sequences.

Example 3

Construction of Expression Vectors for PAS#1 and PAS#5 Fusion Proteins of Interleukin-1 Receptor Antagonist (IL-1ra)

The coding gene for IL-1ra (Carter (1990) Nature 344:633-638) was amplified from the plasmid IRANp969G0350D61L1RN (RZPD, Berlin, Germany) with the cloned cDNA using the oligodeoxynucleotides 5'-AC-GATCGGCGCCAGCTCTTCTGCCCGACCCTCTGGG AGAAAATCC (SEQ ID NO:61) and 5'-CTGGGC AAGCTTACTCGTCCTCCTGGA AGTAG (SEQ ID NO: 62) as primers. The first primer contains a KasI restriction site at the 5'-end, followed by a SapI restriction site (underlined), whereas the second primer contains a HindIII restriction site (underlined). The amplification product was purified and digested with KasI and HindIII and ligated with the accordingly cut vector pASK-IBA4 (IBA, Göttingen, Germany). After transformation of *E. coli* XL1-Blue, plasmids were prepared and the sequences of the cloned synthetic nucleic acid inserts were confirmed by restriction analysis and automated double-stranded DNA sequencing. The plasmid coding for IL-1ra as fusion with a N-terminal Strep-tag II was designated pASK-IL-1ra (FIG. 2E).

For the construction of expression plasmids encoding IL-1 ra as fusion with the amino acid polymer sequences PAS(#1) 200, PAS(#1)400, PAS(#5)192, and PAS(#5)384, pASK-IL-1ra was cut with SapI, dephosphorylated with shrimp alkaline phosphatase, and ligated with an excess of the gene fragment for the 200 residue PAS#1 polymer or for the 192 residue PAS#5 polymer, respectively, isolated from the corresponding intermediate plasmids pPAS(#1)200 and pPAS(#5)192 by restriction digest with SapI (FIG. 2F). After transformation of *E. coli* JM83 (Yanisch-Perron. (1985) Gene 33:103-119), plasmids were prepared and the sizes of the polymer-encoding regions, which were inserted during ligation in one or several repeated copies, were determined by restriction analysis. The plasmids coding for IL-1ra carrying a 200 or 400 residue PAS#1 polymer sequence, i.e. PAS(#1)200-IL-1ra or PAS(#1)400-IL-1ra, and plasmids carrying a 192 or 384 residue PAS#5 polymer sequence, i.e. PAS(#5)192-IL-1ra or PAS(#5)384-IL1ra, were designated pASK-PAS(#1) 200-IL1ra, pASK-PAS(#1)400-IL1ra, pASK-PAS(#5)192-IL1ra, and pASK-PAS(#5)384-IL-1ra respectively.

Example 4

Construction of Expression Vectors for PAS#1 and piSA Fusion Proteins of Neutrophil Gelatinase-Associated Lipocalin (NGAL)

For the construction of expression vectors for PAS#1 and piSA fusion proteins of NGAL the corresponding synthetic gene fragments from Example 1 were cloned on a derivative of pASK75 (Skerra, A. (1994) Gene 151:131-135), harboring the cDNA for a variant of NGAL (Breustedt (2006) loc. cit.) fused with the C-terminal Strep-tag II (Skerra, (2000) Methods Enzymol 326:271-304), carrying an EcoO109I restriction site in between (FIG. 3A). This vector, dubbed pNGAL15-Eco, was cut with EcoO109I, dephosphorylated with shrimp alkaline phosphatase (USB, Cleveland, Ohio), and ligated with the synthetic DNA fragment encoding PAS#1 or piSA (FIG. 3B).

After transformation of *E. coli* XL1-Blue (Bullock (1987) Biotechniques 5: 376-378), plasmids were prepared and the sequences of the cloned synthetic nucleic acid inserts were confirmed by restriction analysis and automated double-stranded DNA sequencing (ABI-Prism™310 Genetic analyzer) using the BigDye™ terminator kit as well as oligodeoxynucleotide primers that enabled sequencing from both sides. The plasmids coding for NGAL carrying a PAS(#1)100 and PAS(#1)200 residue polymer sequence, i.e. NGAL-PAS (#1)100 and NGAL-PAS(#1)200, were named pNGAL-PAS (#1)100 and pNGAL-PAS(#1)200 (FIG. 3C), respectively.

The plasmid coding for NGAL carrying a piSA100 residue polymer sequence, NGAL-piSA100, was named pNGAL-piSA100.

Example 5

Bacterial Production and Purification of Fusion Proteins Between IFNa2b and Genetically Encoded PAS#1, PAS#2, PAS#3, PAS#5, and PAS#1P2 Polymers IFNa2b (calculated mass: 20.9 kDa), PAS(#1)200-IFNa2b (calculated mass: 37.4 kDa), PAS(#1)400-IFNa2b (calculated mass: 54.0 kDa), PAS(#1)600-IFNa2b (calculated mass: 70.5 kDa), PAS(#5)192-IFNa2b (calculated mass: 36.7 kDa), and PAS(#5)384-IFNa2b (calculated mass: 52.6 kDa) were produced in *E. coli* BL21 (Novagen, Madison, USA; Wood (1966) J Mol Biol 16:118-133) harboring the corresponding expression plasmids from Example 2 together with the folding helper plasmid pTUM4 (Schlapschy (2006) Protein Eng. Des. Sel. 20: 273-284) using an 8 L bench top fermenter with a synthetic glucose mineral medium supplemented with 100 mg/l ampicillin and 30 mg/l chloramphenicol, following a procedure as described for the production of recombinant Fab fragments (Schiweck (1995) Proteins 23: 561-565.). Recombinant gene expression was induced by the addition of 500 µg/l anhydrotetracycline (Skerra (1994) Gene 151: 131-135) as soon as the culture reached $OD_{550}$=20. After an induction period of 2.5 h, cells were harvested by centrifugation and resuspended during 10 min in ice-cold periplasmic fractionation buffer (500 mM sucrose, 1 mM EDTA, 100 mM Tris/HCl pH 8.0; 2 ml per L and $OD_{550}$). After adding 15 mM EDTA and 250 µg/ml lysozyme, the cell suspension was incubated for 20 min on ice, centrifuged several times, and the cleared supernatant containing the recombinant protein was recovered. The IFNa2b variants were purified via the Strep-tag II fused to the N-terminus (Skerra (2000) Methods Enzymol 326:271-304) and via gel filtration using a Superdex S75 or S200 HiLoad 16/60 column (Amersham Biosciences, Uppsala, Sweden).

PAS(#2)200-IFNa2b (calculated mass: 37.4 kDa), PAS(#3)200-IFNa2b (calculated mass: 38.6 kDa), and PAS(#1P2)140-IFNa2b (calculated mass: 31.7 kDa), were produced at 22° C. in *E. coli* BL21 harboring the corresponding expression plasmids from Example 2 together with the folding helper plasmid pTUM4 using shaker flask cultures with 2 L LB medium containing 100 mg/l ampicillin and 30 mg/l chloramphenicol. Induction of foreign gene expression was performed with anhydrotetracycline at $OD_{550}$=0.5 over night (typically resulting in $OD_{550}$ of ca. 1.0 at harvest). Periplasmic extraction in the presence of 500 mM sucrose, 1 mM EDTA, 100 mM Tris/HCl pH 8.0 containing 50 µg lysozyme per ml was performed as described (Breustedt (2005) loc. cit.) and followed by purification via the Strep-tag II using streptavidin affinity chromatography (Skerra (2000) loc. cit.) with a high salt buffer (500 mM NaCl, 1 mM EDTA, 100 mM Tris/HCl, pH 8.0).

For all recombinant IFNa2b proteins, homogeneous protein preparations were obtained (FIG. 4A/B/C) with yields of 0.15 mg $L^{-1}$ $OD^{-1}$ for IFNa2b, 0.1 mg $L^{-1}$ $OD^{-1}$ for PAS(#1)200-IFNa2b, 0.06 mg $L^{-1}$ $OD^{-1}$ for PAS(#1)400-IFNa2b, 0.04 mg $L^{-1}$ $OD^{-1}$ for PAS(#1)600-IFNa2b, 0.05 mg $L^{-1}$ $OD^{-1}$ for PAS(#2)200-IFNa2b, 0.05 mg $L^{-1}$ $OD^{-1}$ for PAS(#3)200-IFNa2b, 0.08 mg $L^{-1}$ $OD^{-1}$ for PAS(#5)192-IFNa2b, 0.04 mg $L^{-1}$ $OD^{-1}$ for PAS #(5)384-IFNa2b, and 0.05 mg $L^{-1}$ $OD^{-1}$ for PAS(#1P2)140-IFNa2b.

For the in vitro activity assay, endotoxin contaminations in the protein preparations were further removed. Therefore, the purified proteins were dialysed three times against PBS (115 mM NaCl, 4 mM $KH_2PO_4$, 16 mM $Na_2HPO_4$ pH 7.4) and applied to a Q Sepharose FF 16/200 column (Amersham Biosciences, Uppsala, Sweden) using an Äkta Purifier 10 system with a 50 ml superloop (Amersham Biosciences) and PBS as running buffer. The flow through containing the recombinant protein was collected and concentrated to ca. 1.5 mg/ml by ultrafiltration using Amicon Ultra centrifugal filter devices (30000 MWCO; 15 ml; Millipore, Billerica, Mass.). An additional endotoxin removal step was performed using EndoTrap® affinity columns (Profos AG, Regensburg, Germany) using PBS as running buffer. The final endotoxin content was below 1 EU/ml at a protein concentration of 1 mg/ml as determined using the Endosafe PTS Kit (Charles River Laboratories, L'Arbresle, France).

SDS-PAGE was performed using a high molarity Tris buffer system (Fling and Gregerson (1986) Anal Biochem 155: 83-88). Protein concentrations were determined according to the absorption at 280 nm using calculated extinction coefficients (Gill and von Hippel (1989) Anal Biochem 182: 319-326) of 23590 $M^{-1}$ $cm^{-1}$ both for IFNa2b and its various polymer fusions according to the invention as these did not contribute to UV absorption due to the lack of aromatic acids.

Example 6

Bacterial Production and Purification of Fusion Proteins Between IL-1ra and Genetically Encoded PAS#1 and PAS#5 Polymers IL-1ra (calculated mass: 19.8 kDa), PAS(#1)200-IL-1ra (calculated mass: 35.3 kDa), PAS(#1)400-IL-1ra (calculated mass: 51.9 kDa), PAS(#5)192-IL-1ra (calculated mass: 34.6 kDa), and PAS(#5)384-IL-1ra (calculated mass: 50.5 kDa) were produced in *E. coli* BL21 harboring the corresponding expression plasmids from Example 3 together with the folding helper plasmid pTUM4 at 22° C. using shaker flask cultures with 2 L LB medium containing 100 mg/l ampicillin and 30 mg/l chloramphenicol. Induction of foreign gene expression was performed with anhydrotetracycline at $OD_{550}$=0.5 overnight (typically resulting in $OD_{550}$ of ca. 1.0 at harvest). Periplasmic extraction in the presence of 500 mM sucrose, 1 mM EDTA, 100 mM Tris/HCl pH 8.0 containing 50 µg lysozyme per ml was performed as described (Breustedt (2005) loc. cit.) and followed by purification via the Strep-tag II using streptavidin affinity chromatography (Skerra (2000) loc. cit.) with a high salt buffer (500 mM NaCl, 1 mM EDTA, 100 mM Tris/HCl, pH 8.0).

For all recombinant IL-1ra proteins, homogeneous protein preparations were obtained (FIG. 4D) with yields of 0.1 mg $L^{-1}$ $OD^{-1}$ for IL-1ra, 0.1 mg $L^{-1}$ $OD^{-1}$ for PAS(#1)200-IL-1ra, 0.05 mg $L^{-1}$ $OD^{-1}$ for PAS(#1)400-IL-1ra, 0.1 mg $L^{-1}$ $OD^{-1}$ for PAS(#5)192-IL-1ra, and 0.04 mg $L^{-1}$ $OD^{-1}$ for PAS#(5)384-IL-1ra.

Example 7

Bacterial Production and Purification of Fusion Proteins Between NGAL and Genetically Encoded PAS#1 and piSA Polymers The NGAL (calculated mass: 21.5 kDa) was produced in *E. coli* BL21 harboring the expression plasmid pNGAL15 using an 8 L bench top fermenter essentially as described in Example 4. The NGAL was purified via the Strep-tag II fused to the C-terminus (Skerra (2000) Methods Enzymol 326:271-304).

The NGAL-PAS(#1)100, NGAL-PAS(#1)200, and NGAL-piSA100 (calculated masses: 29.8 kDa, 38.1 kDa, and 29.4 kDa, respectively) were produced at 22° C. in *E. coli* BL21 harboring the corresponding expression plasmids from Example 4 using shaker flask cultures with 2 L LB medium containing 100 mg/l ampicillin. Induction of foreign gene expression was performed with anhydrotetracycline at $OD_{550}$=0.5 overnight (typically resulting in $OD_{550}$ of ca. 1.8 at harvest). Periplasmic extraction in the presence of 500 mM sucrose, 1 mM EDTA, 100 mM Tris/HCl pH 8.0 containing 50 μg lysozyme per ml was performed as described (Breustedt (2005) J Biol Chem 280:484-493) and followed by purification via the Strep-tag II using streptavidin affinity chromatography (Skerra (2000) loc. cit.) with a high salt buffer (500 mM NaCl, 1 mM EDTA, 100 mM Tris/HCl, pH 8.0).

For NGAL-PAS(#1)100 and NGAL-PAS(#1)200, homogeneous protein preparations were obtained after the one step affinity chromatography (FIG. 4E) with yields of 0.1 mg $L^{-1}$ $OD^{-1}$ for NGAL, 0.5 mg $L^{-1}$ $OD^{-1}$ for NGAL-PAS(#1)100, and 0.8 mg $L^{-1}$ $OD^{-1}$ for NGAL-PAS(#1)200. NGAL-piSA100 was further purified via gel filtration using a Superdex S75 HR 10/300 GL column (Amersham Biosciences, Uppsala, Sweden), yielding 0.01 mg $L^{-1}$ $OD^{-1}$.

For the in vivo PK study in female wistar rats, endotoxin contaminations were further removed. Therefore, the purified NGAL, NGAL-PAS(#1)100, and NGAL-PAS(#1)200 proteins were dialysed three times against PBS and applied to a Q Sepharose FF 16/200 column (Amersham Biosciences) using an Äkta Purifier 10 system with a 50 ml superloop (Amersham Biosciences) and PBS as running buffer. The flow through containing the recombinant protein was collected and concentrated to ca. 1.5 mg/ml by ultrafiltration using Amicon Ultra centrifugal filter devices (10000 MWCO; 15 ml; Millipore, Billerica, Mass.). An additional endotoxin removal step was performed using EndoTrap® affinity columns (Profos AG, Regensburg, Germany) using PBS as running buffer. The final endotoxin content was between 5.17 and 21.9 EU/ml at a protein concentration of 1 mg/ml as determined using the Endosafe PTS Kit (Charles River Laboratories, L'Arbresle, France).

Example 8

Measurement of the Hydrodynamic Volume for the Recombinant Fusion Proteins Between IFNa2b and Genetically Encoded PAS#1, PAS#2, PAS#3, PAS#5 or PAS#1P2 Polymers of Different Length by Analytical Gel Filtration Gel permeation chromatography was carried out on a Superdex S200 HR 10/300 GL column (Amersham Biosciences) at a flow rate of 1 ml/min using an Äkta Purifier 10 system (Amersham Biosciences) with PBS (115 mM NaCl, 4 mM $KH_2PO_4$, 16 mM $Na_2HPO_4$ pH 7.4) as running buffer. 250 μl samples of the purified IFNa2b and its PAS#1 polymer fusions with 200, 400 and 600 residues, or PAS#2 and PAS#3 polymers with 200 residues, or PAS#5 polymer fusions with 192 and 384 residues, or PAS#1P2 polymers with 140 residues resulting from the Strep-tag II affinity chromatography as described in Example 5, were individually applied at a concentration of 0.25 mg/ml in PBS. All six proteins eluted as single homogenous peaks as shown in FIG. 5A/B/D.

For column calibration as shown in FIG. 5C/E, 250 μl of a mixture of the following globular proteins (Sigma, Deisenhofen, Germany) were applied in PBS: RNase A (0.2 mg/ml), carbonic anhydrase (0.2 mg/ml), ovalbumin (0.5 mg/ml), bovine serum albumin (0.5 mg/ml), transferrin (0.2 mg/ml) and alcohol dehydrogenase (0.4 mg/ml).

As result, the fusion proteins with the PAS#1 polymers with 200, 400 and 600 residues and the PAS#5 polymers with 192 and 384 residues exhibited significantly larger sizes than corresponding globular proteins with the same molecular weight. The size increase for PAS(#1)200-IFNa2b, PAS(#1) 400-IFNa2b and PAS(#1)600-IFNa2b was 8.4-fold, 16.5-fold and 24.9-fold, respectively, compared with the unfused IFNa2b protein. In contrast, the true mass was only larger by 1.8-fold, 2.6-fold and 3.4-fold. The size increase for PAS(#5) 192-IFNa2b and PAS(#5)384-IFNa2b was 7.7-fold and 13.3-fold, respectively, compared with the unfused IFNa2b protein. In these cases the true mass was only by 1.8-fold and 2.5-fold larger.

Similarly, the fusion proteins with the PAS#2 and PAS#3 polymers with 200 residues exhibited significantly larger sizes than corresponding globular proteins with the same molecular weight. The size increase for PAS(#2)200-IFNa2b and PAS(#3)200-IFNa2b was 8-fold and 7-fold, respectively, compared with the unfused IFNa2b protein. In contrast, the true mass was in both cases only larger by 1.8-fold. The fusion protein with the PAS#1P2 polymer with 140 residues exhibited also a larger size than the corresponding globular proteins with the same molecular weight. However, the size increase for PAS(#1P2)140-IFNa2b was just 3-fold compared with the unfused IFNa2b protein, whereby the true mass was just 1.5-fold larger. Thus, the size increase for PAS(#1P2)140-IFNa2b with a reduced number of proline residues (14 in PAS(#1P2)140) was less pronounced, indicating a major influence of the Pro content on the random coil properties of the amino acid polymer sequences.

In general, these observations clearly indicate the effect of a much increased hydrodynamic volume as it has to be expected if the Pro-Ala-Ser polymer sequences assume random coil conformation (Squire (1981) J Chromatogr A 210: 433-442).

Example 9

Measurement of the Hydrodynamic Volume for the Recombinant Fusion Proteins Between IL-1ra and Genetically Encoded PAS#1 and PAS#5 Polymers of Different Length by Analytical Gel Filtration Gel permeation chromatography was carried out on a Superdex S200 HR 10/300 GL column (Amersham Biosciences) at a flow rate of 1 ml/min using an Äkta Purifier 10 system (Amersham Biosciences) as described in Example 8. All five proteins eluted as single homogenous peaks as shown in FIG. 5F.

For column calibration as shown in FIG. 5G, 250 μl of a mixture of the following globular proteins (Sigma, Deisenhofen, Germany) were applied in PBS: RNase A (0.2 mg/ml), carbonic anhydrase (0.2 mg/ml), ovalbumin (0.5 mg/ml), bovine serum albumin (0.5 mg/ml), transferrin (0.2 mg/ml) and alcohol dehydrogenase (0.4 mg/ml).

As result, the fusion proteins with the PAS#1 polymers with 200 and 400 residues and the PAS#5 polymers with 192 and 384 residues exhibited significantly larger sizes than corresponding globular proteins with the same molecular weight. The size increase for PAS(#1)200-IL-1ra and PAS (#1)400-IL-1ra was 8-fold and 17-fold, respectively, compared with the unfused IL-1ra protein. In contrast, the true mass was only larger by 1.8-fold and 2.6-fold. The size increase for PAS(#5)192-IL-1ra and PAS(#5)384-IL-1ra was 7-fold and 15-fold, respectively, compared with the unfused IL-1ra protein. In these cases the true mass was only by 1.7-fold and 2.5-fold larger.

Again, these observations clearly indicate the effect of a much increased hydrodynamic volume as it has to be expected if the Pro-Ala-Ser polymer sequences assume random coil conformation (Squire (1981) loc. cit.).

Example 10

Measurement of the Hydrodynamic Volume for the Recombinant Fusion Proteins Between NGAL and Genetically Encoded PAS#1 and piSA Polymers by Analytical Gel Filtration Gel permeation chromatography was carried out on a Superdex S75 HR 10/300 GL or Superdex S200 HR 10/300 GL column (Amersham Biosciences) at a flow rate of 0.5 ml/min using an Äkta Purifier 10 system (Amersham Biosciences) as described in Example 8. All four proteins (NGAL, NGAL-PAS(#1)100, NGAL-PAS(#1)200 and NGAL-piSA 100) eluted as single homogenous peaks as shown in FIG. 5H.

For column calibration as shown in FIG. 5I, 250 µl of a mixture of the following globular proteins (Sigma, Deisenhofen, Germany) were applied in PBS:
aprotinin (0.5 mg/ml), ribonuclease (0.4 mg/ml), myoglobin (0.2 mg/ml), carbonic anhydrase (0.2 mg/ml), ovalbumin (0.5 mg/ml), bovine serum albumin (0.5 mg/ml) and transferrin (0.2 mg/ml) for the Superdex S75 10/300 GL run;
cytochrome c (0.2 mg/ml), carbonic anhydrase (0.2 mg/ml), ovalbumin (0.5 mg/ml), bovine serum albumin (0.5 mg/ml), transferrin (0.2 mg/ml) and alcohol dehydrogenase (0.4 mg/ml) for the Superdex S200 10/300 GL run.

As result, the fusion protein with the PAS#1 polymer with 100 residues and, even more pronounced, the version with 200 residues showed significantly larger sizes than corresponding globular proteins with the same molecular weight. The size increase for NGAL-PAS(#1)100 and NGAL-PAS (#1)200 was 3.4-fold and 4.9-fold, respectively, compared with the unfused NGAL protein. The true mass was only by 1.4-fold and 1.8-fold larger, respectively. This observation clearly indicates the effect of a larger hydrodynamic volume as it has to be expected if the Pro-Ala-Ser polymer sequence assumes random coil conformation (Squire (1981) J Chromatogr A 210:433-442).

In contrast, the fusion protein with the piSA polymer with 100 residues showed a less significant size increase compared with corresponding globular proteins having the same molecular weight. The size increase for NGAL-piSA100 was just 2.5-fold compared with the unfused NGAL protein whereby the true mass was by 1.4 fold bigger. Thus, fusion with the 100 residue Pro-Ala-Ser polymer leads to a significantly larger increase in the hydrodynamic volume than with the 100 residue Ala-Ser polymer.

Example 11

Detection of Random Coil Conformation for the Genetically Encoded PAS#1 Polymer Fused to IFNa2b by Circular Dichroism Spectroscopy Secondary structure was analysed using a J-810 spectropolarimeter (Jasco, Groβ-Umstadt, Germany) equipped with a quartz cuvette 106-QS (0.1 mm path length; Hellma, Müllheim Germany). Spectra were recorded from 190 to 250 nm at room temperature by accumulating 16 or 32 runs (bandwidth 1 nm, scan speed 100 nm/min, response 4 s) using 15.9 to 38.7 µM protein solutions in 50 mM $K_2SO_4$, 20 mM K-phosphate pH 7.5. After correction for solution blanks, spectra were smoothed using the instrument software, and the molar ellipticity $\Theta_M$ was calculated according to the equation:

$$\Theta_M = \frac{\Theta_{obs}}{c \cdot d}$$

whereby $\Theta_{obs}$ denotes the measured ellipticity, c the protein concentration [mol/l], d the path length of the quartz cuvette [cm]. The $\Theta_M$ values were plotted against the wavelength using Kaleidagraph (Synergy Software, Reading, Pa.). The circular dichroism (CD) spectrum for the recombinant IFNa2b is in accordance with previously published data for this α-helix bundle protein (Radhakrishnan (1996) Structure 4:1453-1463), whereas the spectra for PAS(#1)200-IFNa2b, PAS(#1)400-IFNa2b, and PAS(#1)600-IFNa2b reveal significant contributions of random coil conformation (FIG. 6A). To analyze the spectroscopic contributions by the polymer fusion partner in greater detail the molar difference CD spectra with respect to the unfused IFNa2b were calculated (FIG. 6B). As result, a strong minimum around 200 nm, with increasing amplitude from 100 to 200 residues, which is characteristic of random coil conformation (Greenfield (1969) loc. cit.; Sreerama (2000) loc. cit.; Fändrich (2002) loc. cit.), was observed. Thus, the Pro-Ala-Ser sequence as part of the recombinant fusion protein appears to be present as a random coil polymer under physiological buffer conditions.

Example 12

Detection of Random Coil Conformation for the Genetically Encoded PAS#5 Polymer Fused to IFNa2b by Circular Dichroism Spectroscopy Secondary structure was analysed by CD as described in Example 11 using 2.3 to 5.1 µM protein solutions. The spectra for PAS(#5)192-IFNa2b and PAS(#5)384-IFNa2b reveal significant contributions of random coil conformation (FIG. 6E). To analyze the spectroscopic contributions by the polymer fusion partner in greater detail the molar difference CD spectra with respect to the unfused IFNα-2b were calculated (FIG. 6F). As result, a strong minimum around 200 nm characteristic of random coil conformation (Greenfield (1969) loc. cit.; Sreerama (2000) loc. cit.; Fändrich (2002) loc. cit.) was observed. Thus, the Pro-Ala-Ser sequence as part of the recombinant fusion protein appears to be present as a random coil polymer under physiological buffer conditions.

Example 13

Detection of Random Coil Conformation for the Genetically Encoded PAS#2, PAS#3 and PAS#1P2 Polymer Fused to IFNa2b by Circular Dichroism Spectroscopy Secondary structure was analysed by CD as described in Example 11 using 16.1 to 22.9 µM protein solutions. The spectra for PAS(#2)200-IFNa2b, PAS(#3)200-IFNa2b, and PAS(#1P2)140-IFNa2b reveal significant contributions of random coil conformation (FIG. 6C). To analyze the spectroscopic contributions by the polymer fusion partner in greater detail, the molar difference CD spectra with respect to the unfused IFNa2b were calculated (FIG. 6D). As result, a minimum around 200 nm characteristic of random coil conformation (Greenfield (1969) loc. cit.; Sreerama (2000) loc. cit.; Fändrich (2002) loc. cit.) was observed. Thus, the Pro-Ala-Ser sequence as part of the recombinant fusion protein appears to be present as a random coil polymer under physiological buffer conditions. However, in the case of the PAS#1P2 polymer with a reduced number of proline residues the CD signal for random coil is significantly reduced, indicating a dependency of the random coil character upon the Pro content in the amino acid polymer sequences.

Example 14

Detection of Random Coil Conformation for the Genetically Encoded PAS#1 and PAS#5 Polymer Fused to IL-1ra by Circular dichroism Spectroscopy Secondary structure was analysed by CD as described in Example 11 using 0.9 to 3.3 µM protein solutions. The circular dichroism (CD) spectrum for the recombinant IL-1ra is in accordance with the crystal structure for this dominantly β-sheet protein (Schreuder (1997) Nature 386:194-200), whereas the spectra for PAS(#1)200-IL-1ra, PAS(#1)400-IL-1ra, PAS(#5)192-IL-1ra, and PAS(#5)384-IL-1ra reveal a significant fraction of random coil conformation (FIG. 6G). To analyze the spectroscopic contributions by the polymer fusion partner in greater detail, the molar difference CD spectra with respect to the unfused IL-1ra were calculated (FIG. 6H). As result, a strong minimum around 200 nm characteristic of random coil conformation (Greenfield (1969) loc. cit.; Sreerama (2000) loc. cit.; Fändrich (2002) loc. cit.) was observed. Thus, the Pro-Ala-Ser sequence as part of the recombinant fusion protein with IL-1ra appears to be present as a random coil polymer under physiological buffer conditions.

Example 15

Detection of Random Coil Conformation for the Genetically Encoded PAS#1 Polymer Fused to NGAL by Circular Dichroism Spectroscopy Secondary structure was analysed by CD as described in Example 11 using 23 to 28 µM protein solutions. The CD spectrum for the recombinant NGAL is in accordance with previously published data (Breustedt (2006) loc. cit.), whereas the spectra for NGAL-PAS(#1)100 and NGAL-PAS(#1)200 reveal significant contributions of random coil conformation (FIG. 6I). To analyze the spectroscopic contributions by the polymer fusion partner in greater detail the molar difference CD spectra with respect to the unfused NGAL were calculated (FIG. 6J). As result, a strong minimum around 200 nm characteristic of random coil conformation (Greenfield (1969) loc. cit.; Sreerama (2000) loc. cit.; Fändrich (2002) loc. cit.) was observed. Thus, the Pro-Ala-Ser sequence as part of the recombinant fusion protein appears to be present as a random coil polymer under physiological buffer conditions.

Example 16

Detection of β-Sheet Conformation for the Genetically Encoded piSA Polymer Fused to NGAL by Circular Dichroism Spectroscopy Secondary structure was analysed as described in Example 11 using a 5 µM protein solution. The spectrum for NGAL-piSA100 reveals a significant content of β-sheet conformation (FIG. 6K). To analyze the spectroscopic contributions by the polymer fusion partner in greater detail the molar difference CD spectra with respect to the unfused NGAL were calculated (FIG. 6K). As result, a strong minimum at 218 nm characteristic of β-sheet conformation (Greenfield (1969) loc. cit.; Sreerama (2000) loc. cit.; Fändrich (2002) loc. cit.) was observed. Thus, the Ala-Ser polymer sequence as part of the recombinant fusion protein appears to predominantly adopt a compact β-sheet secondary structure under physiological buffer conditions.

Example 17

Quantitative Analysis of the Secondary Structure of IFNa2b, NGAL, and their Polymer Fusions The secondary structure of IFNa2b, PAS(#1)200-IFNa2b, PAS(#1)400-IFNa2b, PAS(#1)600-IFNa2b, PAS(#5)192-IFNa2b, PAS(#5)384-IFNa2b, NGAL, NGAL-PAS(#1)100, NGAL-PAS(#1)200, and NGAL-piSA100 was quantified from the corresponding CD spectra measured in Examples 11, 12, 15 and 16 using the secondary structure deconvolution program CDNN ver. 2.1 (Böhm (1992) Prot Eng 5:191-195) with a set of 33 base spectra for the deconvolution of complex CD spectra. The results obtained using said deconvolution program CDNN are provided in the following Table:

|  | IFNa2b | PAS(#1) 100-IFNa2b | PAS(#1) 400-IFNa2b | PAS(#1) 600-IFNa2b | PAS(#5) 192-IFNa2b | PAS(#5) 384-IFNa2b | NGAL | NGAL-PAS(#1) 100 | NGAL-PAS(#1) 200 | NGAL-piSA100 |
|---|---|---|---|---|---|---|---|---|---|---|
| α-helix | 38.2% | 17.6% | 10.0% | 8.1% | 19.1% | 10.5% | 7.2% | 5.9% | 6.1% | 8.4% |
| anti-parallel β-sheet | 1.8% | 11.6% | 11.7% | 7.9% | 9.0% | 9.9% | 38.3% | 22.6% | 27.2% | 50.0% |
| parallel α-sheet | 8.4% | 3.6% | 2.5% | 2.0% | 3.3% | 2.4% | 3.6% | 2.7% | 2.9% | 4.4% |
| β-turn | 19.2% | 35.6% | 36.5% | 40.0% | 41.4% | 40.8% | 18.5% | 23.7% | 22.3% | 15.6% |
| random coil | 35.9% | 42.0% | 46.8% | 52.6% | 43.5% | 48.1% | 33.3% | 42.2% | 39.1% | 28.2% |
| Σ total | 103.5% | 110.4% | 107.4% | 110.7% | 116.4% | 111.7% | 100.8% | 97.0% | 97.6% | 106.6% |
| Σ β-turn and random coil | 55.1% | 77.6% | 83.3% | 92.6% | 84.5% | 88.9% | 51.8% | 65.9% | 61.4% | 43.8% |

Compared with the predominantly α-helical secondary structure content of the recombinant IFNa2b, which is in accordance with its known three-dimensional structure as an α-helix bundle protein (Radhakrishnan (1996) loc. cit.), the fraction of unstructured conformation comprising random coil and turns for the whole protein clearly increases with the length of the PAS(#1) and PAS(#5) polymers fused to IFNa2b (see bottom row of the Table shown above, which summarizes the results of the CD spectra deconvolution with the program CDNN). A generally similar but less pronounced effect can be seen for NGAL-PAS(#1)100 and NGAL-PAS(#1)200. These spectroscopic data are in agreement with the experimentally determined enlarged hydrodynamic volumes of the PAS(#1) and PAS(#5) fusion proteins of IFNa2b and NGAL as determined in Examples 8 and 10, which has to be expected for an unstructured random coil conformation (Cantor (1980) loc. cit.; Creighton (1993) loc. cit.).

In contrast, in case of the NGAL-piSA100 fusion protein the amount of turns and random coil is even lower than in the recombinant NGAL, whereas the amount of anti-parallel β-sheet increases from 38.3% in NGAL to 50.0% in NGAL-piSA100. Thus, the piSA100 polymer comprising only Ser and Ala residues assumes a β-sheet structure rather than a random coil, which is reflected by the less significant increase in the hydrodynamic volume as measured in Example 10.

Different results were obtained when a theoretical analysis of the PAS#1, PAS#5, and piSA polymer sequences was performed using the Chou-Fasman algorithm (Chou and Fasman (1974) loc. cit.). The results of this analysis are illustrated in FIG. 14. Regardless of the amino acid composition and sequence of the amino acid polymer, this algorithm predicts more than 50% α-helical secondary structure, which is in clear contrast with the experimental data. Thus, this algorithm is not useful to predict unstructured conformation of an amino acid polymer with confidence.

Example 18

Test of Serum Stability of PAS(#1)200-IFNa2b and PAS(#5)192-IFNa2b

Serum stability of PAS(#1)200-IFNa2b and PAS(#5)192-IFNa2b was analyzed by mixing of 10 µl test protein at a concentration of 1 mg/ml and 50 µl mouse plasma (Rockland Immunochemicals, Gilbertsville, Pa.), resulting in a test protein concentration of 0.17 mg/ml and a plasma concentration of 83% (v/v). The samples were incubated at 37° C. for 24 h or 48 h. Samples (6 µl) were taken at 0 h, 1 h, 3 h, 6 h, 8 h, and 24 h in the case of PAS(#5)192-IFNa2b and at 0 h, 1 h, 3 h, 6 h, 8 h, 24 h, 32 h, and 48 h in the case of PAS(#1)200-IFNa2b, and immediately diluted with 54 µl SDS-PAGE electrophoresis buffer (50 mM Tris/HCl pH 8.8, 190 mM glycine, 1 g/l SDS) and 15 µl SDS-PAGE loading buffer (250 mM Tris/HCl pH 8.0, 25% (v/v) glycerine, 7.5% (w/v) SDS, 0.25 mg/ml bromophenol blue, 12.5% (v/v) (3-mercaptoethanol). After 5 min heating at 95° C., 25 µl of these samples and a reference sample (0.1 µg of the corresponding test protein) were subjected to 12% SDS-PAGE. Following electro-transfer onto a nitrocellulose membrane (Schleicher & Schuell, Dassel, Germany) by means of a semi-dry blotting apparatus, the membrane was placed in a dish and washed 3 times for 20 min with 10 ml PBST (PBS containing 0.1% v/v Tween 20). The membrane was incubated for 10 min in 20 ml PBST containing 2 µg/ml egg-white avidin to mask endogenous protein-bound biotin groups and then 20 µl of the StrepTactin® Alkaline Phosphatase conjugate (IBA, Göttingen, Germany) were directly added (at a dilution of 1:1000). After incubation for 1 h and washing the membrane twice for 5 min with 20 ml PBST and PBS and once for 5 min with 20 ml AP buffer (100 mM Tris/HCl pH 8.8, 100 mM NaCl, 5 mM MgCl$_2$), the chromogenic reaction was performed (without shaking) by adding 10 ml of AP buffer with 5 µl nitroblue tetrazolium (NBT, Biomol, Hamburg, Germany; 75 mg/ml in 70% w/v DMF) and 30 µl 5-bromo-4-chloro-3-indolyl-phosphate p-toluidine salt (BCIP, Roth, Karlsruhe, Germany; 50 mg/ml in DMF) until the bands appeared. The reaction was stopped by washing with water and air-drying of the membrane.

For both test proteins the blots reveal signals of constant intensity for all time points (FIG. 7A/B). Also, no degradation products could be detected. Thus, there is no proteolytic degradation or sign of aggregation, which would lead to a decrease of the test protein within the investigated time period of 24 h for PAS(#5)192-IFNa2b and 48 h for PAS(#1)200-IFNa2b.

Example 19

Detection of Prolonged Plasma Half-Life for the Recombinant Fusion Proteins Between IFNa2b and a Genetically Encoded PAS#1 Polymer In Vivo Adult BALB/c mice (Harlan-Winckelmann, Borchen, Germany) were injected intravenously according to the following table:

| Group | A | B | C |
| --- | --- | --- | --- |
| Test item | IFNa2b | PAS(#1)200-IFNa2b | PAS(#1)400-IFNa2b |
| Administration route | | Intravenous | |
| Dose [mg/kg b.w.] | 5.0 | 5.0 | 5.0 |
| Concentration [mg/ml] | 1.0 | 1.0 | 1.0 |
| Application volume [ml/kg b.w.] | | 5.0 | |
| No. of animals/group | 2 | 2 | 2 |
| No. of blood sampling time points | 3 | 3 | 3 |
| No. of animals/sampling time point | 1 | 1 | 1 |
| No. of blood samplings/animal | 2/1 | 2/1 | 2/1 |

The total volume of intravenously administered test item was calculated according to the individual body weight recorded on the day of administration (e.g. an animal with 25 g body weight (b.w.) received 125 µl of 1 mg/ml test item). Blood sampling was performed 30 min, 120 min, and 360 min after injection according to the following table:

| Group | Test item | Animal no. | Blood sampling time points (min after administration) | | |
| --- | --- | --- | --- | --- | --- |
| | | | 30 | 120 | 360 |
| A | IFNa2b | 1 | x | | x |
| | | 2 | | x | |
| B | PAS(#1)200-IFNa2b | 3 | x | | x |
| | | 4 | | x | |
| C | PAS(#1)400-IFNa2b | 5 | x | | x |
| | | 6 | | x | |

For each substance two animals from one group were injected. Blood samples (approximately 100 µl each) were taken from the tail vein and stored on crushed ice for ca. 20 min. After centrifugation for 10 min at 10000 g and 4° C. the supernatant (plasma) was immediately frozen and stored at −20° C.

For qualitative detection of the fusion protein on a Western blot, 10 µl aliquots of the cleared plasma samples were diluted with 90 µl PBS. 10 µl thereof (corresponding to 1 µl plasma) were diluted with 6 µl PBS and mixed with 4 µl SDS-PAGE loading buffer (250 mM Tris/HCl pH 8.0, 7.5% w/v SDS, 25% v/v glycerol, 0.25 mg/ml bromophenol blue) containing 12.5% v/v 2-mercaptoethanol. After 5 min heating at 95° C., these samples were subjected to 10% SDS-PAGE. Following electro-transfer onto a nitrocellulose membrane (Schleicher & Schuell, Dassel, Germany) by means of a semi-dry blotting apparatus, the membrane was placed in a dish and washed 3 times for 20 min with 10 ml PBST (PBS containing 0.1% v/v Tween 20). Then the membrane was incubated for 10 min in 20 ml PBST containing 20 µl of the mouse anti-human IFNa2b antibody 9D3 (Abcam, Cambridge, UK; at a dilution of 1:1000). After further incubation for 60 min the membrane was washed 3 times for 20 min with 10 ml PBST and then incubated with a anti-mouse IgG Alkaline Phosphatase conjugate (Sigma-Aldrich, St. Louis, Mo.) for 60 min.

After washing the membrane twice for 5 min with 20 ml PBST and once for 5 mM with 20 ml AP buffer (100 mM Tris/HCl pH 8.8, 100 mM NaCl, 5 mM $MgCl_2$), the chromogenic reaction was performed (without shaking) by adding 10 ml of AP buffer with 5 µl nitroblue tetrazolium (NBT, Biomol, Hamburg, Germany; 75 mg/ml in 70% w/v DMF) and 30 µl 5-bromo-4-chloro-3-indolyl-phosphate p-toluidine salt (BCIP, Roth, Karlsruhe, Germany; 50 mg/ml in DMF) until the bands appeared. The reaction was stopped by washing with water and air-drying of the membrane.

FIG. 8 shows samples containing IFNa2b, PAS(#1)200-IFNa2b, and PAS(#1)400-IFNa2b from equivalent time points. While IFNa2b is no longer detectable after 120 min, PAS(#1)200-IFNa2b and PAS(#1)400-IFNa2b can be detected for periods up to 360 min. These data indicate that the plasma half-life of IFNa2b is significantly prolonged when fused with the Pro-Ala-Ser polymers.

For quantitative detection of the fusion protein in an ELISA, the wells of a 96 well microtitre plate (Maxisorb, NUNC, Denmark) were coated overnight at 4° C. with 100 µl of a 5 µg/ml solution of the mouse anti-human IFNa2b antibody 9D3 (Abcam, Cambridge, UK) in 5% (w/v) $NaHCO_3$ pH 9.3. After removal of the coating solution the wells were blocked with 200 µl of 2% (w/v) BSA in PBS for 1 h and washed three times with PBST. The plasma samples of animals no. 1/2 (IFNa2b), no. 3/4 (PAS(#1)200-IFNa2b), and no. 5/6 (PAS(#1)400-IFNa2b) were applied in dilution series in PBST containing 0.5% (v/v) mouse plasma from an untreated animal and incubated for 1 h. The wells were then washed three times with PBST and incubated for 1 h with 100 µl of a 1:1000 diluted solution of a second mouse anti-human IFNa2b antibody HRP-conjugate (4E10-HRP; Abcam, Cambridge, UK) in PBST. After washing twice with PBST and twice with PBS the chromogenic reaction was started by adding 100 µl of 1 mg/ml ABTS solution in ABTS buffer (Roche Diagnostics, Mannheim, Germany) as substrate for the peroxidase and after 20 min at 25° C. the absorbance at 405 nm was measured. Concentrations of IFNa2b, PAS(#1)200-IFNa2b, and PAS(#1)400-IFNa2b in the plasma samples were quantified by comparison with standard curves which were determined for dilution series for the corresponding purified recombinant proteins at defined concentrations in PBST containing 0.5% (v/v) mouse plasma from untreated animals.

To estimate the plasma half-life of IFNa2b, PAS(#1)200-IFNa2b, and PAS(#1)400-IFNa2b, the concentration values, c(t), were determined for each time point from the ELISA measurements and plotted against time post intravenous injection, t. These data were numerically fitted using Kaleida-Graph software assuming a mono-exponential decay according to the equation $$c(t) = c_0 e^{-ln2 \frac{t}{\tau_{1/2}}}$$

whereby $\tau_{1/2}$ is the plasma half-life, and $c_0$ is the total blood concentration at time point zero, which was set to a fixed value of 78 µg/ml under the assumption of an average animal weight of 25 g and a typical blood to body weight ratio for mouse of 0.064.

FIG. 9 depicts the kinetics of blood clearance in vivo. While the recombinant IFNa2b shows a rapid clearance from blood with a half-life of just ca. 5.5 min, the PAS(#1)200-IFNa2b and PAS(#1)400-IFNa2b fusion proteins have a more than 10-fold and 60-fold extended half-life of ca. 61 min and 6 h respectively. These data are in agreement with the Western blot analysis shown above and prove that the in vivo plasma half-life of IFNa2b is significantly prolonged due to fusion with the Pro-Ala-Ser polymers, whereby the half-life becomes longer with increasing length of the amino acid polymer.

Example 20

Detection of Prolonged Plasma Half-Life for the Recombinant Fusion Proteins Between IFNa2b and the Genetically Encoded PAS#1 and PAS#5 Polymers In Vivo Adult C57BL/6 mice (Charles River Laboratories, L'Arbresle, France) were injected intravenously according to the following table:

| | Group | | | | |
|---|---|---|---|---|---|
| Test item | A<br>PAS(#1)<br>200-<br>IFNa2b | B<br>PAS(#1)<br>400-<br>IFNa2b | C<br>PAS(#1)<br>600-<br>IFNa2b | D<br>PAS(#5)<br>192-<br>IFNa2b | E<br>PAS(#5)<br>384-<br>IFNa2b |
| Administration route | | | Intravenous | | |
| Dose [mg/kg b.w.] | | | 7.0 | | |
| Concentration [mg/ml] | 1.0 | 1.0 | 1.0 | 1.0 | 1.0 |
| Application volume [ml/kg b.w.] | | | 7.0 | | |
| No. of animals/group | 2 | 2 | 2 | 2 | 2 |
| No. of blood sampling time points | 4 | 4 | 4 | 4 | 4 |
| No. of animals/sampling time point | 1 | 1 | 1 | 1 | 1 |
| No. of blood samplings/animal | 2 | 2 | 2 | 2 | 2 |

The total volume of intravenously administered test item was calculated according to the individual body weight recorded on the day of administration (e.g. an animal with 18 g body weight (b.w.) received 125 µl of 1 mg/ml test item). Blood sampling was performed 30 min, 120 min, 240 min, and 480 min after injection according to the following table:

| Group | Test item | Animal no. | Blood sampling time points (min after administration) | | | |
|---|---|---|---|---|---|---|
| | | | 30 | 120 | 240 | 480 |
| A | PAS(#1)200-IFNa2b | 1 | x | | x | |
| | | 2 | | x | | x |
| B | PAS(#1)400-IFNa2b | 3 | x | | x | |
| | | 4 | | x | | x |
| C | PAS(#1)600-IFNa2b | 5 | x | | x | |
| | | 6 | | x | | x |
| D | PAS(#5)192-IFNa2b | 7 | x | | x | |
| | | 8 | | x | | x |
| E | PAS(#5)384-IFNa2b | 9 | x | | x | |
| | | 10 | | x | | x |

For each substance two animals from one group were injected. Blood samples (approximately 100 µl each) were taken from the tail vein and stored on crushed ice for ca. 20 min. After centrifugation for 10 min at 10000 g and 4° C. the supernatant (plasma) was immediately frozen and stored at −20° C.

For quantitative detection of the fusion protein in an ELISA, the wells of a 96 well microtitre plate (Maxisorb, NUNC, Denmark) were coated overnight at 4° C. with 100 µl of a 5 µg/ml solution of the mouse anti-human IFNa2b antibody 9D3 (Abcam, Cambridge, UK) in 5% (w/v) NaHCO$_3$ pH 9.3. After removal of the coating solution the wells were blocked with 200 µl of 2% (w/v) BSA in PBS for 1 h and washed three times with PBST. The plasma samples of animals no. 1/2 (PAS(#1)200-IFNa2b), no. 3/4 (PAS(#1)400-IFNa2b), no. 5/6 (PAS(#1)600-IFNa2b), no. 7/8 (PAS(#5) 192-IFNa2b), and no. 9/10 (PAS(#5)384-IFNa2b) were applied in dilution series in PBST containing 0.25% (v/v) dummy mouse plasma (from an untreated animal) and incubated for 1 h. The wells were then washed three times with PBST and incubated for 1 h with 100 µl of a 1:1000 diluted solution of a second mouse anti-human IFNa2b antibody HRP-conjugate (4E10-HRP; Abcam, Cambridge, UK) in PBST. After washing twice with PBST and twice with PBS the chromogenic reaction was started by adding 100 µl of 1 mg/ml ABTS peroxidase substrate solution in the recommended buffer (Roche Diagnostics, Mannheim, Germany) and, after incubation for 20 min at 25° C., the absorbance at 405 nm was measured. Concentrations of PAS(#1)200-IFNa2b, PAS(#1)400-IFNa2b, PAS(#1)600-IFNa2b, PAS (#5)192-IFNa2b, and PAS(#5)384-IFNa2b in the plasma samples were quantified by comparison with standard curves, which were determined for dilution series for the corresponding purified recombinant proteins at defined concentrations in PBST containing 0.25% (v/v) dummy mouse plasma.

To estimate the plasma half-life of PAS(#1)200-IFNa2b, PAS(#1)400-IFNa2b, PAS(#1)600-IFNa2b, PAS(#5)384-IFNa2b, and PAS(#5)384-IFNa2b, the concentration values, c(t), were determined for each time point from the ELISA measurements and plotted against time post intravenous injection, t. These data were numerically fitted using Kaleida-Graph software assuming a mono-exponential decay according to the equation $$c(t) = c_0 e^{-ln2\frac{t}{\tau_{1/2}}}$$

whereby $\tau_{1/2}$ is the plasma half-life, and $c_0$ is the total blood concentration at time point zero, which should have a value of ca. 116 µg/ml under the assumption of an average animal weight of 18 g and a typical blood to body weight ratio for mouse of 0.064.

FIG. 10 depicts the kinetics of blood clearance in vivo. The half-life of PAS(#1)200-IFNa2b is ca. 66 min, which is in good agreement with the half-life of 61 min for PAS(#1)200-IFNa2b in Example 19, although a lower dose of 5 mg/kg b.w. compared to 7 mg/kg b.w. was used here. Thus, variation of the mouse line and the dose had no significant influence on the pharmacokinetics. The PAS(#1)400-IFNa2b and PAS(#1) 600-IFNa2b fusion proteins have a more than 60-fold and 70-fold extended half-life of ca. 316 min and 406 min, respectively, compared with the recombinant IFNa2b not fused with an amino acid polymer sequence. The PAS(#5)192-IFNa2b and PAS(#5)384-IFNa2b fusion proteins have a more than 7-fold and 58-fold extended half-life of ca. 40 min and 321 min, respectively. These data show that the in vivo plasma half-life of IFNa2b is significantly prolonged due to fusion with the Pro-Ala-Ser polymers, whereby the half-life becomes longer with increasing length of the amino acid polymer.

Example 21

Detection of Prolonged Plasma Half-Life for the Recombinant Fusion Proteins Between NGAL and the Genetically Encoded PAS#1 Polymer In Vivo Adult female Wistar rats were injected intravenously according to the following table:

| Group | A | B | C |
|---|---|---|---|
| Test item | NGAL | NGAL-PAS(#1)100 | NGAL-PAS(#1)200 |
| Administration route | intravenous | | |
| Dose [mg/kg b.w.] | 5.0 | 5.0 | 5.0 |
| Concentration [mg/ml] | 1.0 | 1.0 | 1.0 |
| Application volume [ml/kg b.w.] | 5.0 | | |
| No. of animals/group | 6 | 6 | 6 |
| No. of blood sampling time points | 8 | 8 | 8 |
| No. of animals/sampling time point | 3 | 3 | 3 |
| No. of blood samplings/animal | 4 | 4 | 4 |

The total volume of intravenously administered test item was calculated according to the individual body weight recorded on the day of administration (e.g. animal no. 104 with 210 g body weight (b.w.) received 1050 µl of 1 mg/ml NGAL). Blood sampling was performed 5 min, 10 min, 30 min, 60 min, 120 min, 240 min, 360 min, and 1440 min after injection according to the following table:

| Group | Test item | Animal no. | 5 | 10 | 30 | 60 | 120 | 240 | 360 | 1440 |
|---|---|---|---|---|---|---|---|---|---|---|
| A | NGAL | 104, 105 | x |   | x |   | x |   | x |   |
|   |   | 107, 108 |   | x |   | x |   | x |   | x |
| B | NGAL-PAS(#1)100 | 110, 111 | x |   | x |   | x |   | x |   |
|   |   | 113, 114 |   | x |   | x |   | x |   | x |
| C | NGAL-PAS(#1)200 | 116, 117 | x |   | x |   | x |   | x |   |
|   |   | 119, 120 |   | x |   | x |   | x |   |   |

For each substance two animals of one group were needed, each providing four samples at different time points, whereby the experiments were performed in double. Blood samples (approximately 0.5 ml each) were taken with Pasteur pipettes from the retro-orbital plexus under slight ether anesthesia and immediately transferred into lithium heparin-Microvette® vials, shaken by hand, and stored on crushed ice for ca. 20 min. After centrifugation for 10 min at 10000 g and 4° C. the supernatant (plasma) was immediately frozen and stored at −80° C. The animals were sacrificed by ether inhalation immediately after the last blood sampling.

For qualitative detection of the fusion protein on a Western blot, 100 µl aliquots of the cleared plasma samples were diluted with 400 µl PBS. 1.25 µl thereof (corresponding to 0.25 µl plasma) were diluted with 14.75 µl PBS and mixed with 4 µl SDS-PAGE loading buffer (250 mM Tris/HCl pH 8.0, 7.5% w/v SDS, 25% v/v glycerol, 0.25 mg/ml bromophenol blue) containing 12.5% v/v 2-mercaptoethanol. After 5 min heating at 95° C., these samples were subjected to 12% SDS-PAGE. Following electro-transfer onto a nitrocellulose membrane (Schleicher & Schuell, Dassel, Germany) by means of a semi-dry blotting apparatus the membrane was placed in a dish and washed 3 times for 20 min with 10 ml PBST (PBS containing 0.1% v/v Tween 20). Then the membrane was incubated for 10 min in 20 ml PBST containing 2 µg/ml egg-white avidin to mask endogenous protein-bound biotin groups and 20 µA of the StrepTactin® Alkaline Phosphatase conjugate (IBA GmbH, Göttingen, Germany) were directly added (at a dilution of 1:1000) and incubation was continued for 60 min.

After washing the membrane twice for 5 min with 20 ml PBST and once for 5 min with 20 ml AP buffer (100 mM Tris/HCl pH 8.8, 100 mM NaCl, 5 mM $MgCl_2$), the chromogenic reaction was performed (without shaking) by adding 10 ml of AP buffer with 5 µl nitroblue tetrazolium (NBT, Biomol, Hamburg, Germany; 75 mg/ml in 70% w/v DMF) and 30 µl 5-bromo-4-chloro-3-indolyl-phosphate p-toluidine salt (BCIP, Roth, Karlsruhe, Germany; 50 mg/ml in DMF) until the bands appeared. The reaction was stopped by washing with water and air-drying of the membrane.

FIG. 11 shows two series of mixed samples containing NGAL, NGAL-PAS(#1)100, and NGAL-PAS(#1)200 from equivalent time points. While NGAL is no longer detectable after 10 min, NGAL-PAS(#1)100 and NGAL-PAS(#1)200 can be detected for periods up to 120 min. These data indicate that the plasma half-life of NGAL is significantly prolonged when fused with the Pro-Ala-Ser polymer.

For quantitative detection of the fusion protein in an ELISA, the wells of a 96 well microtitre plate (Maxisorb, NUNC, Denmark) were coated overnight at 4° C. with 50 µl of a 5 µg/ml solution of an anti-human Lipocalin-2/NGAL antibody (R&D Systems, Minneapolis, Minn.) in PBS. After washing three times with PBST the wells were blocked with 200 µl of 3% (w/v) BSA in PBST for 2 h and washed again three times with PBST. The plasma samples of animals 104/105 (NGAL) and 116/117 (NGAL-PAS(#1)200) were applied in dilution series in PBST containing 2.5% (v/v) rat plasma from untreated animals (Elevage Janvier, Le Genest ST. Isle, France; Aurigon Life Science, Tutzing, Germany) and incubated for 1.5 h. The wells were then washed three times with PBST and incubated for 1 h with 50 µl of a 1:1000 dilution of StrepTactin® Alkaline Phosphatase conjugate. After washing twice with PBST and twice with PBS the chromogenic reaction was started by adding 50 µl of 0.5 µg/ml p-nitrophenyl phosphate in AP-buffer as substrate and after 20 at 25° C. min the absorbance at 405 nm was measured. Concentrations of NGAL and NGAL-PAS(#1)200 in the plasma samples were quantified by comparison with standard curves which were determined for dilution series for the corresponding purified proteins at defined concentrations in PBST containing 2.5% (v/v) rat plasma from untreated animals.

To estimate the plasma half-life of NGAL and NGAL-PAS (#1)200, the concentration values, c(t), determined from the ELISA measurements were plotted against time post intravenous injection, t, and numerically fitted using KaleidaGraph software. A mono-exponential decay was assumed according to the equation $$c(t) = c_0 e^{-ln2 \frac{t}{\tau_{1/2}}}$$

whereby $\tau_{1/2}$ is the plasma half-life parameter, and $c_0$ is the total blood concentration at time point zero, which should have a value of ca. 80 µg/ml under the assumption of an average animal weight of 210 g and a typical blood to body weight ratio for rat of 0.064.

FIG. 12 depicts the kinetics of blood clearance in vivo. While the recombinant NGAL shows a rapid clearance from blood with a half-life of just ca. 3 min, the NGAL-PAS(#1)200 fusion protein has a ten-fold extended half-life of ca. 31 min. These data are in agreement with the Western blot analysis shown above and prove that the in vivo plasma half-life of NGAL is significantly prolonged due to fusion with the Pro-Ala-Ser polymer.

Example 22

Comparison of the Activity of the Commercially Available IntronA and the Recombinant PAS(#1)200-IFNa2b by IP-10 Release Assay with Human PBMCs $2 \times 10^5$ human PBMCs in a total volume of 100 µl were stimulated for 24 h at 37° C. with a dilution series of IntronA (Schering Corporation, Kenilworth, N.J.), PAS(#1)200-IFNa2b, and an unrelated recombinant Fab fragment as negative control. The start concentration for all three test proteins was $10^6$ U/ml with respect to the specific activity of $2.6 \times 10^8$ U/mg for IntronA as specified in the data sheet. This specific unit concentration was used to calculate equal unit concentrations for the amount of PAS(#1)200-IFNa2b and an equivalent amount of the recombinant Fab fragment. The concentration of the released IP-10 (CXCL10; interferon gamma inducible 10 kDa protein) in the supernatant upon induction by interferon alpha was determined by using the human IP-10 ELISA Set (BD OptEIA™, BD Biosciences Pharmingen, USA).

FIG. 13 depicts the activity of the three test proteins. While the recombinant PAS(#1)200-IFNa2b shows at higher concentrations comparable activities as IntronA, the latter is more active at lower concentrations, yielding on average a similar activity profile. Unstimulated PBMCs as well as PBMCs stimulated with the Fab fragment did not release significant amounts of IP-10. As endotoxin, which might also induce the release of IP-10, was removed in the preparations both of PAS(#1)200-IFNa2b and of the Fab fragment as described in Example 5, the activity of PAS(#1)200-IFNa2b can be clearly attributed to the IFNa2b moiety of the fusion protein. Thus, the Pro-Ala-Ser polymer does not interfere with the biological activity of IFNa2b.

The invention claimed is:

1. A biologically active protein comprising
   (a) a first domain comprising an amino acid sequence having said biological activity; and
   (b) a second domain consisting of at least 80 amino acid residues consisting of alanine, serine and proline residues, and which forms a random coil conformation which mediates an increased in vivo and/or in vitro stability of said biologically active protein compared with the biologically active protein lacking the second domain.

2. The biologically active protein according to claim 1, wherein said second domain comprises a plurality of amino acid repeats and wherein no more than 6 consecutive amino acid residues are the same amino acid.

3. The biologically active protein according to claim 1, wherein said proline residues consist of 4% to 40% of said second domain.

4. The biologically active protein according to claim 1, wherein said second domain comprises the amino acid sequence selected from the group consisting of

| | |
|---|---|
| ASPAAPAPASPAAPAPSAPA; | (SEQ ID NO: 18) |
| AAPASPAPAAPSAPAPAAPS; | (SEQ ID NO: 20) |
| APSSPSPSAPSSPSPSASPSS; | (SEQ ID NO: 22) |
| SAPSSPSPSAPSSPSPASPS; | (SEQ ID NO: 63) |
| SSPSAPSPSSPASPSPSSPA; | (SEQ ID NO: 24) |
| AASPAAPSAPPAAASPAAPSAPPA; and | (SEQ ID NO: 26) |
| ASAAAPAAASAAASAPSAAA. | (SEQ ID NO: 28) |

5. The biologically active protein according to claim 1, wherein said second domain consists of about 100 to 3000 amino acid residues.

6. The biologically active protein according to claim 1, wherein said first domain is selected from the group consisting of binding molecules, antibody fragments, cytokines, growth factors, hormones and enzymes.

7. The biologically active protein according to claim 6, wherein said binding molecule is selected from the group consisting of antibodies, Fab fragments, F(ab')₂ fragments, CDR derived peptidomimetics, single chain variable fragments (scFv), lectins and lipocalins.

8. The biologically active protein according to claim 1, wherein said first domain comprising an amino acid sequence having biological activity is selected from the group consisting of granulocyte colony stimulating factor, human growth hormone, alpha-interferon, beta-interferon, gamma-interferon, tumor necrosis factor, erythropoietin, coagulation factor VIII, gp120/gp160, soluble tumor necrosis factor I and II receptor, reteplase, exendin-4, anakinra, interleukin-2, and neutrophil gelatinase-associated lipocalin.

9. The biologically active protein according to claim 1, wherein said increased in vivo stability of said biologically active protein is a prolonged plasma half-life of said biologically active protein.

10. A composition comprising the biologically active protein according to claim 1.

11. The composition according to claim 10 which is a pharmaceutical composition, optionally further comprising a pharmaceutical acceptable carrier.

12. A nucleic acid molecule encoding the biologically active protein of claim 1.

13. A vector comprising the nucleic acid of claim 12.

14. A cell comprising the nucleic acid according to claim 12.

15. A method for the preparation of the biologically active protein according to claim 1 comprising culturing a cell comprising (a) a nucleic acid molecule encoding the biologically active protein of claim 1 or (b) a vector comprising a nucleic acid molecule encoding the biologically active protein of claim 1 and isolating said biologically active protein from the culture.

16. Kit comprising the biologically active protein according to claim 1, a nucleic acid encoding the biologically active protein of claim 1, a vector comprising a nucleic acid and encoding the biologically active protein of claim 1 or a cell comprising (a) a nucleic acid molecule encoding the biologically active protein of claim 1 or (b) a vector comprising a nucleic acid molecule encoding the biologically active protein of claim 1.

17. A method of treating hormone deficiency-related disorders, auto-immune disease, cancer, anemia, neovascular diseases, infectious/inflammatory diseases, thrombosis, myocardial infarction, diabetes, reperfusion injury or other kidney diseases comprising administering the biologically active protein according to claim 1, a nucleic acid encoding the biologically active protein of claim 1, a vector comprising a nucleic acid and encoding the biologically active protein of claim 1 or a cell comprising (a) a nucleic acid molecule encoding the biologically active protein of claim 1 or (b) a vector comprising a nucleic acid molecule encoding the biologically active protein of claim 1.

* * * * *

SEQUENCE LISTING

```
<160> NUMBER OF SEQ ID NOS: 63

<210> SEQ ID NO 1
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequenceencoding amino acid polymer piSA"

<400> SEQUENCE: 1
gccgctgctg catcctctgc aagctccgct tcttcctcta gctccgcagc tgcatctgct      60

<210> SEQ ID NO 2
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid polymer piSA"

<400> SEQUENCE: 2

Ala Ala Ala Ala Ser Ser Ala Ser Ser Ala Ser Ser Ser Ser Ser Ala
1               5                   10                  15

Ala Ala Ser Ala
            20

<210> SEQ ID NO 3
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid polymer"

<400> SEQUENCE: 3
gctgcttccg ctgctgcttc ctccgctgct gcttccgctg ctgctgcttc cgcttcctcc      60

<210> SEQ ID NO 4
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid polymer"

<400> SEQUENCE: 4

Ala Ala Ser Ala Ala Ala Ser Ser Ala Ala Ala Ser Ala Ala Ala Ala
1               5                   10                  15

Ser Ala Ser Ser
            20
```

-continued

```
<210> SEQ ID NO 5
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid polymer"

<400> SEQUENCE: 5
gcttccgctt ccgcttccgc ttccgcttcc gcttcctccg ctgcttccgc tgcttccgct        60

<210> SEQ ID NO 6
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid polymer"

<400> SEQUENCE: 6
```

Ala Ser Ala Ser Ala Ser Ala Ser Ala Ser Ala Ser Ser Ala Ala Ser
1               5                   10                  15

Ala Ala Ser Ala
            20

```
<210> SEQ ID NO 7
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence
      encoding amino acid polymer"

<400> SEQUENCE: 7
tccgctgctt cctcctccgc ttcctcctcc tccgctgctt cctccgcttc cgctgctgct        60

<210> SEQ ID NO 8
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid polymer"

<400> SEQUENCE: 8
```

Ser Ala Ala Ser Ser Ser Ala Ser Ser Ser Ser Ala Ala Ser Ser Ala
1               5                   10                  15

Ser Ala Ala Ala
            20

```
<210> SEQ ID NO 9
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid polymer"

<400> SEQUENCE: 9
tcctcctcct ccgctgcttc cgctgcttcc gctgctgctg ctgcttcctc ctccgcttcc        60
```

<210> SEQ ID NO 10
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid polymer"

<400> SEQUENCE: 10

Ser Ser Ser Ser Ala Ala Ser Ala Ala Ser Ala Ala Ala Ala Ala Ser
1               5                   10                  15

Ser Ser Ala Ser
            20

<210> SEQ ID NO 11
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid polymer"

<400> SEQUENCE: 11
tcctccgctt cctcctccgc tgcttcctcc tccgcttcct cctcctccgc ttccgctgct      60

<210> SEQ ID NO 12
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid polymer"

<400> SEQUENCE: 12

Ser Ser Ala Ser Ser Ser Ala Ala Ser Ser Ser Ala Ser Ser Ser Ser
1               5                   10                  15

Ala Ser Ala Ala
            20

<210> SEQ ID NO 13
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid polymer"

<400> SEQUENCE: 13
tccgcttccg cttccgcttc cgcttccgct tccgctgctt cctccgcttc ctccgcttcc      60

<210> SEQ ID NO 14
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid polymer"

<400> SEQUENCE: 14

Ser Ala Ser Ala Ser Ala Ser Ala Ser Ala Ser Ala Ala Ser Ser Ala
1               5                   10                  15

Ser Ser Ala Ser

20

<210> SEQ ID NO 15
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid polymer"

<400> SEQUENCE: 15
gcttcctccg ctgctgcttc cgctgctgct gcttcctccg ctgcttccgc ttcctcctcc    60

<210> SEQ ID NO 16
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid polymer"

<400> SEQUENCE: 16

Ala Ser Ser Ala Ala Ala Ser Ala Ala Ala Ala Ser Ser Ala Ala Ser
1               5                   10                  15

Ala Ser Ser Ser
            20

<210> SEQ ID NO 17
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid polymer PAS#1"

<400> SEQUENCE: 17
gcctctccag ctgcacctgc tccagcaagc cctgctgcac cagctccgtc tgctcctgct    60

<210> SEQ ID NO 18
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid polymer PAS#1"

<400> SEQUENCE: 18

Ala Ser Pro Ala Ala Pro Ala Pro Ala Ser Pro Ala Ala Pro Ala Pro
1               5                   10                  15

Ser Ala Pro Ala
            20

<210> SEQ ID NO 19
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid polymer PAS#2"

<400> SEQUENCE: 19
gctgctccgg cttccccggc tccggctgct ccgtccgctc cggctccggc tgctccgtcc    60

```
<210> SEQ ID NO 20
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid polymer PAS#2"

<400> SEQUENCE: 20

Ala Ala Pro Ala Ser Pro Ala Pro Ala Ala Pro Ser Ala Pro Ala Pro
1               5                   10                  15

Ala Ala Pro Ser
            20

<210> SEQ ID NO 21
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid polymer PAS#3"

<400> SEQUENCE: 21
gctccgtcct cccgtcccc gtccgctccg tcctccccgt cccggcttc ccgtcctcc        60

<210> SEQ ID NO 22
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid polymer PAS#3"

<400> SEQUENCE: 22

Ala Pro Ser Ser Pro Ser Pro Ser Ala Pro Ser Ser Pro Ser Pro Ala
1               5                   10                  15

Ser Pro Ser Ser
            20

<210> SEQ ID NO 23
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid polymer PAS#4"

<400> SEQUENCE: 23
tcctccccgt ccgctccgtc cccgtcctcc ccggcttccc cgtccccgtc ctccccggct     60

<210> SEQ ID NO 24
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid polymer PAS#4"

<400> SEQUENCE: 24

Ser Ser Pro Ser Ala Pro Ser Pro Ser Ser Pro Ala Ser Pro Ser Pro
1               5                   10                  15

Ser Ser Pro Ala
```

-continued

```
                20

<210> SEQ ID NO 25
<211> LENGTH: 72
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid polymer PAS#5"

<400> SEQUENCE: 25
gccgcttctc cagcagctcc ttctgctcca ccagcagctg caagccctgc tgcaccaagc    60
gcacctcctg ct                                                        72

<210> SEQ ID NO 26
<211> LENGTH: 24
<212> TYPE: PRT
<213> ORGANISM: artificial sequence
<220> FEATURE:
<221> NAME/KEY: source
<223> OTHER INFORMATION: /note="Description of artificial sequence:
      amino acid polymer PAS#5"

<400> SEQUENCE: 26

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 27
<211> LENGTH: 60
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid polymer PAS#1P2"

<400> SEQUENCE: 27
gcctctgctg cagcacctgc agcagcaagc gcagctgcat ctgctccatc tgcagctgct    60

<210> SEQ ID NO 28
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      amino acid polymer PAS#1P2"

<400> SEQUENCE: 28

Ala Ser Ala Ala Ala Pro Ala Ala Ala Ser Ala Ala Ala Ser Ala Pro
1               5                   10                  15

Ser Ala Ala Ala
            20

<210> SEQ ID NO 29
<211> LENGTH: 63
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid sequence for a building
      block for PAS#1"

<400> SEQUENCE: 29
```

```
gcctctccag ctgcacctgc tccagcaagc cctgctgcac cagctccgtc tgctcctgct    60
gcc                                                                  63
```

<210> SEQ ID NO 30
<211> LENGTH: 21
<212> TYPE: PRT
<213> ORGANISM: artificial sequence
<220> FEATURE:
<221> NAME/KEY: source
<223> OTHER INFORMATION: /note="Description of artificial sequence:
    amino acid sequence for a building block for PAS#1"

<400> SEQUENCE: 30

Ala Ser Pro Ala Ala Pro Ala Pro Ala Ser Pro Ala Ala Pro Ala Pro
1               5                   10                  15

Ser Ala Pro Ala Ala
            20

<210> SEQ ID NO 31
<211> LENGTH: 63
<212> TYPE: DNA
<213> ORGANISM: artificial sequence
<220> FEATURE:
<221> NAME/KEY: source
<223> OTHER INFORMATION: /note="Description of artificial sequence:
    nucleic acid sequence encoding amino acid sequence for a
    building block for PAS#2"

<400> SEQUENCE: 31

```
gccgcacctg cttctccggc tccagcagct cctagcgcac cagctcctgc tgctccatct    60
gcc                                                                  63
```

<210> SEQ ID NO 32
<211> LENGTH: 21
<212> TYPE: PRT
<213> ORGANISM: artificial sequence
<220> FEATURE:
<221> NAME/KEY: source
<223> OTHER INFORMATION: /note="Description of artificial sequence:
    amino acid sequence for a building block for PAS#2"

<400> SEQUENCE: 32

Ala Ala Pro Ala Ser Pro Ala Pro Ala Ala Pro Ser Ala Pro Ala Pro
1               5                   10                  15

Ala Ala Pro Ser Ala
            20

<210> SEQ ID NO 33
<211> LENGTH: 63
<212> TYPE: DNA
<213> ORGANISM: artificial sequence
<220> FEATURE:
<221> NAME/KEY: source
<223> OTHER INFORMATION: /note="Description of artificial sequence:
    nucleic acid sequence encoding amino acid sequence for a building
    block for PAS#3"

<400> SEQUENCE: 33

```
gccccttctt ctccaagccc ttctgctcca tctagcccat ctcctgcatc tcctagctct    60
gcc                                                                  63
```

<210> SEQ ID NO 34
<211> LENGTH: 21
<212> TYPE: PRT
<213> ORGANISM: artificial sequence

```
<220> FEATURE:
<221> NAME/KEY: source
<223> OTHER INFORMATION: /note="Description of artificial sequence:
      amino acid sequence for a building block for PAS#3"

<400> SEQUENCE: 34

Ala Pro Ser Ser Pro Ser Pro Ser Ala Pro Ser Ser Pro Ser Pro Ala
1               5                   10                  15

Ser Pro Ser Ser Ala
            20

<210> SEQ ID NO 35
<211> LENGTH: 75
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid sequence for a building
      block for PAS#5"

<400> SEQUENCE: 35
gccgcttctc cagcagctcc ttctgctcca ccagcagctg caagccctgc tgcaccaagc      60
gcacctcctg ctgcc                                                      75

<210> SEQ ID NO 36
<211> LENGTH: 25
<212> TYPE: PRT
<213> ORGANISM: artificial sequence
<220> FEATURE:
<221> NAME/KEY: source
<223> OTHER INFORMATION: /note="Description of artificial sequence:
      amino acid sequence for a building block for PAS#5"

<400> SEQUENCE: 36

Ala Ala Ser Pro Ala Ala Pro Ser Ala Pro Pro Ala Ala Ala Ser Pro
1               5                   10                  15

Ala Ala Pro Ser Ala Pro Pro Ala Ala
            20                  25

<210> SEQ ID NO 37
<211> LENGTH: 63
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid sequence for a building
      block for piSA"

<400> SEQUENCE: 37
gccgctgctg catcctctgc aagctccgct tcttcctcta gctccgcagc tgcatctgct      60
gcc                                                                   63

<210> SEQ ID NO 38
<211> LENGTH: 21
<212> TYPE: PRT
<213> ORGANISM: artificial sequence
<220> FEATURE:
<221> NAME/KEY: source
<223> OTHER INFORMATION: /note="Description of artificial sequence:
      amino acid sequence for a building block for piSA"

<400> SEQUENCE: 38

Ala Ala Ala Ala Ser Ser Ala Ser Ser Ala Ser Ser Ser Ser Ala
1               5                   10                  15
```

-continued

Ala Ala Ser Ala Ala
            20

<210> SEQ ID NO 39
<211> LENGTH: 63
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid sequence for a building
      block for PAS#1P2"

<400> SEQUENCE: 39
gcctctgctg cagcacctgc agcagcaagc gcagctgcat ctgctccatc tgcagctgct    60
gcc                                                                  63

<210> SEQ ID NO 40
<211> LENGTH: 21
<212> TYPE: PRT
<213> ORGANISM: artificial sequence
<220> FEATURE:
<221> NAME/KEY: source
<223> OTHER INFORMATION: /note="Description of artificial sequence:
      amino acid sequence for a building block for PAS#1P2"

<400> SEQUENCE: 40

Ala Ser Ala Ala Ala Pro Ala Ala Ala Ser Ala Ala Ser Ala Pro
1               5                  10                  15

Ser Ala Ala Ala Ala
            20

<210> SEQ ID NO 41
<211> LENGTH: 622
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid sequence of the PAS#1
      polymer with 200 residues"

<400> SEQUENCE: 41
tgctcttctg cctctccagc tgcacctgct ccagcaagcc ctgctgcacc agctccgtct     60
gctcctgctg cctctccagc tgcacctgct ccagcaagcc ctgctgcacc agctccgtct    120
gctcctgctg cctctccagc tgcacctgct ccagcaagcc ctgctgcacc agctccgtct    180
gctcctgctg cctctccagc tgcacctgct ccagcaagcc ctgctgcacc agctccgtct    240
gctcctgctg cctctccagc tgcacctgct ccagcaagcc ctgctgcacc agctccgtct    300
gctcctgctg cctctccagc tgcacctgct ccagcaagcc ctgctgcacc agctccgtct    360
gctcctgctg cctctccagc tgcacctgct ccagcaagcc ctgctgcacc agctccgtct    420
gctcctgctg cctctccagc tgcacctgct ccagcaagcc ctgctgcacc agctccgtct    480
gctcctgctg cctctccagc tgcacctgct ccagcaagcc ctgctgcacc agctccgtct    540
gctcctgctg cctctccagc tgcacctgct ccagcaagcc ctgctgcacc agctccgtct    600
gctcctgctg cctgaagagc tt                                             622

<210> SEQ ID NO 42
<211> LENGTH: 201
<212> TYPE: PRT
<213> ORGANISM: artificial sequence
<220> FEATURE:
<221> NAME/KEY: source
<223> OTHER INFORMATION: /note="Description of artificial sequence:
     amino acid sequence of the PAS#1 polymer with 200 residues"

<400> SEQUENCE: 42

```
Ala Ser Pro Ala Ala Pro Ala Pro Ala Ser Pro Ala Ala Pro Ala Pro
1               5                   10                  15
Ser Ala Pro Ala Ala Ser Pro Ala Ala Pro Ala Pro Ala Ser Pro Ala
            20                  25                  30
Ala Pro Ala Pro Ser Ala Pro Ala Ala Ser Pro Ala Ala Pro Ala Pro
            35                  40                  45
Ala Ser Pro Ala Ala Pro Ala Pro Ser Ala Pro Ala Ala Ser Pro Ala
50                  55                  60
Ala Pro Ala Pro Ala Ser Pro Ala Ala Pro Ala Pro Ser Ala Pro Ala
65                  70                  75                  80
Ala Ser Pro Ala Ala Pro Ala Pro Ala Ser Pro Ala Ala Pro Ala Pro
                85                  90                  95
Ser Ala Pro Ala Ala Ser Pro Ala Ala Pro Ala Pro Ala Ser Pro Ala
            100                 105                 110
Ala Pro Ala Pro Ser Ala Pro Ala Ala Ser Pro Ala Ala Pro Ala Pro
        115                 120                 125
Ala Ser Pro Ala Ala Pro Ala Pro Ser Ala Pro Ala Ala Ser Pro Ala
        130                 135                 140
Ala Pro Ala Pro Ala Ser Pro Ala Ala Pro Ala Pro Ser Ala Pro Ala
145                 150                 155                 160
Ala Ser Pro Ala Ala Pro Ala Pro Ser Ala Pro Ala Ala Pro Ala Pro
                165                 170                 175
Ser Ala Pro Ala Ala Ser Pro Ala Ala Pro Ala Pro Ser Ala Pro Ala
            180                 185                 190
Ala Pro Ala Pro Ser Ala Pro Ala Ala
            195                 200
```

<210> SEQ ID NO 43
<211> LENGTH: 526
<212> TYPE: DNA
<213> ORGANISM: artificial sequence
<220> FEATURE:
<221> NAME/KEY: source
<223> OTHER INFORMATION: /note="Description of artificial sequence:
     nucleic acid sequence encoding amino acid sequence of IFN a2b and
     Strep-tag II"

<400> SEQUENCE: 43

```
gaaaaaggcg ccagctcttc tgcctgtgat ctgcctcaaa cccacagcct gggtagcagg      60
aggaccttga tgctcctggc acagatgagg agaatctctc tttctcctg cttgaaggac     120
agacatgact ttgatttcc ccaggaggag tttggcaacc agttccaaaa ggctgaaacc      180
atccctgtcc tccatgagat gatccagcag atcttcaatc tcttcagcac aaaggactca     240
tctgctgctt gggatgagac cctcctagac aaattctaca ctgaactcta ccagcagctg     300
aatgacctgg aagcctgtgt gatacagggg gtggggtga cagagactcc cctgatgaag     360
gaggactcca ttctggctgt gaggaaatac ttccaaagaa tcactctcta tctgaaagag     420
aagaaataca gcccttgtgc ctgggaggtt gtcagagcag aaatcatgag atctttttct     480
tgtcaacaa acttgcaaga aagtttaaga agtaaggaat aagctt                    526
```

<210> SEQ ID NO 44
<211> LENGTH: 173
<212> TYPE: PRT
<213> ORGANISM: artificial sequence
<220> FEATURE:
<221> NAME/KEY: source
<223> OTHER INFORMATION: /note="Description of artificial sequence:
    amino acid sequence of IFN a2b and Strep-tag II"

<400> SEQUENCE: 44

Glu Lys Gly Ala Ser Ser Ala Cys Asp Leu Pro Gln Thr His Ser
1               5                   10                  15

Leu Gly Ser Arg Arg Thr Leu Met Leu Leu Ala Gln Met Arg Arg Ile
            20                  25                  30

Ser Leu Phe Ser Cys Leu Lys Asp Arg His Asp Phe Gly Phe Pro Gln
        35                  40                  45

Glu Glu Phe Gly Asn Gln Phe Gln Lys Ala Glu Thr Ile Pro Val Leu
    50                  55                  60

His Glu Met Ile Gln Gln Ile Phe Asn Leu Phe Ser Thr Lys Asp Ser
65                  70                  75                  80

Ser Ala Ala Trp Asp Glu Thr Leu Leu Asp Lys Phe Tyr Thr Glu Leu
                85                  90                  95

Tyr Gln Gln Leu Asn Asp Leu Glu Ala Cys Val Ile Gln Gly Val Gly
            100                 105                 110

Val Thr Glu Thr Pro Leu Met Lys Glu Asp Ser Ile Leu Ala Val Arg
        115                 120                 125

Lys Tyr Phe Gln Arg Ile Thr Leu Tyr Leu Lys Glu Lys Lys Tyr Ser
    130                 135                 140

Pro Cys Ala Trp Glu Val Val Arg Ala Glu Ile Met Arg Ser Phe Ser
145                 150                 155                 160

Leu Ser Thr Asn Leu Gln Glu Ser Leu Arg Ser Lys Glu
                165                 170

<210> SEQ ID NO 45
<211> LENGTH: 1126
<212> TYPE: DNA
<213> ORGANISM: artificial sequence
<220> FEATURE:
<221> NAME/KEY: source
<223> OTHER INFORMATION: /note="Description of artificial sequence:
    nucleic acid sequence encoding amino acid sequence of the N-
    terminus of IFN a2b after insertion of PAS#1 polymer sequence"

<400> SEQUENCE: 45
gaaaaaggcg ccagctcttc tgcctctcca gctgcacctg ctccagcaag ccctgctgca    60
ccagctccgt ctgctcctgc tgcctctcca gctgcacctg ctccagcaag ccctgctgca   120
ccagctccgt ctgctcctgc tgcctctcca gctgcacctg ctccagcaag ccctgctgca   180
ccagctccgt ctgctcctgc tgcctctcca gctgcacctg ctccagcaag ccctgctgca   240
ccagctccgt ctgctcctgc tgcctctcca gctgcacctg ctccagcaag ccctgctgca   300
ccagctccgt ctgctcctgc tgcctctcca gctgcacctg ctccagcaag ccctgctgca   360
ccagctccgt ctgctcctgc tgcctctcca gctgcacctg ctccagcaag ccctgctgca   420
ccagctccgt ctgctcctgc tgcctctcca gctgcacctg ctccagcaag ccctgctgca   480
ccagctccgt ctgctcctgc tgcctctcca gctgcacctg ctccagcaag ccctgctgca   540
ccagctccgt ctgctcctgc tgcctctcca gctgcacctg ctccagcaag ccctgctgca   600
ccagctccgt ctgctcctgc tgcctgtgat ctgcctcaaa cccacagcct gggtagcagg   660
aggaccttga tgctcctggc acagatgagg agaatctctc tttctcctg cttgaaggac    720 agacatgact ttggatttcc ccaggaggag tttggcaacc agttccaaaa ggctgaaacc   780
atccctgtcc tccatgagat gatccagcag atcttcaatc tcttcagcac aaaggactca   840

-continued

```
tctgctgctt gggatgagac cctcctagac aaattctaca ctgaactcta ccagcagctg    900
aatgacctgg aagcctgtgt gatacagggg gtggggtga cagagactcc cctgatgaag    960
gaggactcca ttctggctgt gaggaaatac ttccaaagaa tcactctcta tctgaaagag   1020
aagaaataca gcccttgtgc ctgggaggtt gtcagagcag aaatcatgag atcttttct    1080 ttgtcaacaa acttgcaaga aagtttaaga agtaaggaat aagctt                  1126
```

<210> SEQ ID NO 46
<211> LENGTH: 373
<212> TYPE: PRT
<213> ORGANISM: artificial sequence
<220> FEATURE:
<221> NAME/KEY: source
<223> OTHER INFORMATION: /note="Description of artificial sequence: amino acid sequence of the N-terminus of IFN a2b after insertion of PAS#1 polymer sequence"

<400> SEQUENCE: 46

```
Glu Lys Gly Ala Ser Ser Ala Ser Pro Ala Ala Pro Ala Pro Ala
1               5                   10                  15

Ser Pro Ala Ala Pro Ala Pro Ser Ala Pro Ala Ala Ser Pro Ala Ala
            20                  25                  30

Pro Ala Pro Ala Ser Pro Ala Ala Pro Ala Pro Ser Ala Pro Ala Ala
        35                  40                  45

Ser Pro Ala Ala Pro Ala Pro Ala Ser Pro Ala Ala Pro Ala Pro Ser
    50                  55                  60

Ala Pro Ala Ala Ser Pro Ala Ala Pro Ala Pro Ala Ser Pro Ala Ala
65                  70                  75                  80

Pro Ala Pro Ser Ala Pro Ala Ala Ser Pro Ala Ala Pro Ala Pro Ala
                85                  90                  95

Ser Pro Ala Ala Pro Ala Pro Ser Ala Pro Ala Ala Ser Pro Ala Ala
            100                 105                 110

Pro Ala Pro Ala Ser Pro Ala Ala Pro Ala Pro Ser Ala Pro Ala Ala
        115                 120                 125

Ser Pro Ala Ala Pro Ala Pro Ala Ser Pro Ala Ala Pro Ala Pro Ser
    130                 135                 140

Ala Pro Ala Ala Ser Pro Ala Ala Pro Ala Pro Ala Ser Pro Ala Ala
145                 150                 155                 160

Pro Ala Pro Ser Ala Pro Ala Ala Ser Pro Ala Ala Pro Ala Pro Ala
                165                 170                 175

Ser Pro Ala Ala Pro Ala Pro Ser Ala Pro Ala Ala Ser Pro Ala Ala
            180                 185                 190

Pro Ala Pro Ala Ser Pro Ala Ala Pro Ala Pro Ser Ala Pro Ala Ala
        195                 200                 205

Cys Asp Leu Pro Gln Thr His Ser Leu Gly Ser Arg Arg Thr Leu Met
    210                 215                 220

Leu Leu Ala Gln Met Arg Arg Ile Ser Leu Phe Ser Cys Leu Lys Asp
225                 230                 235                 240

Arg His Asp Phe Gly Phe Pro Gln Glu Glu Phe Gly Asn Gln Phe Gln
                245                 250                 255

Lys Ala Glu Thr Ile Pro Val Leu His Glu Met Ile Gln Gln Ile Phe
            260                 265                 270

Asn Leu Phe Ser Thr Lys Asp Ser Ser Ala Ala Trp Asp Glu Thr Leu
        275                 280                 285

Leu Asp Lys Phe Tyr Thr Glu Leu Tyr Gln Gln Leu Asn Asp Leu Glu
    290                 295                 300
```

```
Ala Cys Val Ile Gln Gly Val Gly Val Thr Glu Thr Pro Leu Met Lys
305                 310                 315                 320

Glu Asp Ser Ile Leu Ala Val Arg Lys Tyr Phe Gln Arg Ile Thr Leu
            325                 330                 335

Tyr Leu Lys Glu Lys Lys Tyr Ser Pro Cys Ala Trp Glu Val Val Arg
            340                 345                 350

Ala Glu Ile Met Arg Ser Phe Ser Leu Ser Thr Asn Leu Gln Glu Ser
        355                 360                 365

Leu Arg Ser Lys Glu
        370
```

<210> SEQ ID NO 47
<211> LENGTH: 487
<212> TYPE: DNA
<213> ORGANISM: artificial sequence
<220> FEATURE:
<221> NAME/KEY: source
<223> OTHER INFORMATION: /note="Description of artificial sequence: nucleic acid sequence encoding amino acid sequence of IL-1ra and Strep-tag II"

<400> SEQUENCE: 47

```
gaaaaaggcg ccagctcttc tgcccgaccc tctgggagaa atccagcaa gatgcaagcc      60
ttcagaatct gggatgttaa ccagaagacc ttctatctga ggaacaacca actagttgct     120
ggatacttgc aaggaccaaa tgtcaattta gaagaaaga tagatgtggt acccattgag     180
cctcatgctc tgttcttggg aatccatgga gggaagatgt gcctgtcctg tgtcaagtct     240
ggtgatgaga ccagactcca gctggaggca gttaacatca ctgacctgag cgagaacaga     300
aagcaggaca gcgcttcgc cttcatccgc tcagacagcg ccccaccac cagttttgag      360
tctgccgcct gccccggttg gttcctctgc acagcgatgg aagctgacca gcccgtcagc     420
ctcaccaata tgcctgacga aggcgtcatg gtcaccaaat tctacttcca ggaggacgag     480
taagctt                                                                487
```

<210> SEQ ID NO 48
<211> LENGTH: 160
<212> TYPE: PRT
<213> ORGANISM: artificial sequence
<220> FEATURE:
<221> NAME/KEY: source
<223> OTHER INFORMATION: /note="Description of artificial sequence: amino acid sequence of IL-1ra and Strep-tag II"

<400> SEQUENCE: 48

```
Glu Lys Gly Ala Ser Ser Ser Ala Arg Pro Ser Gly Arg Lys Ser Ser
1               5                   10                  15

Lys Met Gln Ala Phe Arg Ile Trp Asp Val Asn Gln Lys Thr Phe Tyr
            20                  25                  30

Leu Arg Asn Asn Gln Leu Val Ala Gly Tyr Leu Gln Gly Pro Asn Val
        35                  40                  45

Asn Leu Glu Glu Lys Ile Asp Val Val Pro Ile Glu Pro His Ala Leu
    50                  55                  60

Phe Leu Gly Ile His Gly Gly Lys Met Cys Leu Ser Cys Val Lys Ser
65                  70                  75                  80

Gly Asp Glu Thr Arg Leu Gln Leu Glu Ala Val Asn Ile Thr Asp Leu
                85                  90                  95

Ser Glu Asn Arg Lys Gln Asp Lys Arg Phe Ala Phe Ile Arg Ser Asp
            100                 105                 110
```

| Ser | Gly | Pro | Thr | Thr | Ser | Phe | Glu | Ser | Ala | Ala | Cys | Pro | Gly | Trp | Phe |
|---|---|---|---|---|---|---|---|---|---|---|---|---|---|---|---|
| | | 115 | | | | | 120 | | | | 125 | | | | |

| Leu | Cys | Thr | Ala | Met | Glu | Ala | Asp | Gln | Pro | Val | Ser | Leu | Thr | Asn | Met |
|---|---|---|---|---|---|---|---|---|---|---|---|---|---|---|---|
| | 130 | | | | | 135 | | | | | 140 | | | | |

| Pro | Asp | Glu | Gly | Val | Met | Val | Thr | Lys | Phe | Tyr | Phe | Gln | Glu | Asp | Glu |
|---|---|---|---|---|---|---|---|---|---|---|---|---|---|---|---|
| 145 | | | | | 150 | | | | | 155 | | | | | 160 |

<210> SEQ ID NO 49
<211> LENGTH: 1087
<212> TYPE: DNA
<213> ORGANISM: artificial sequence
<220> FEATURE:
<221> NAME/KEY: source
<223> OTHER INFORMATION: /note="Description of artificial sequence: nucleic acid sequence encoding amino acid sequence of the N-terminus of IL-1ra after insertion of PAS#1 polymer sequence"

<400> SEQUENCE: 49

```
gaaaaaggcg ccagctcttc tgcctctcca gctgcacctg ctccagcaag ccctgctgca      60
ccagctccgt ctgctcctgc tgcctctcca gctgcacctg ctccagcaag ccctgctgca     120
ccagctccgt ctgctcctgc tgcctctcca gctgcacctg ctccagcaag ccctgctgca     180
ccagctccgt ctgctcctgc tgcctctcca gctgcacctg ctccagcaag ccctgctgca     240
ccagctccgt ctgctcctgc tgcctctcca gctgcacctg ctccagcaag ccctgctgca     300
ccagctccgt ctgctcctgc tgcctctcca gctgcacctg ctccagcaag ccctgctgca     360
ccagctccgt ctgctcctgc tgcctctcca gctgcacctg ctccagcaag ccctgctgca     420
ccagctccgt ctgctcctgc tgcctctcca gctgcacctg ctccagcaag ccctgctgca     480
ccagctccgt ctgctcctgc tgcctctcca gctgcacctg ctccagcaag ccctgctgca     540
ccagctccgt ctgctcctgc tgcctctcca gctgcacctg ctccagcaag ccctgctgca     600
ccagctccgt ctgctcctgc tgcccgaccc tctgggagaa aatccagcaa gatgcaagcc     660
ttcagaatct gggatgttaa ccagaagacc ttctatctga ggaacaacca actagttgct     720
ggatacttgc aaggaccaaa tgtcaattta aagaaaaaga tagatgtggt acccattgag     780
cctcatgctc tgttcttggg aatccatgga gggaagatgt gcctgtcctg tgtcaagtct     840
ggtgatgaga ccagactcca gctggaggca gttaacatca ctgacctgag cgagaacaga     900
aagcaggaca gcgcttcgc cttcatccgc tcagacagcg cccccaccac cagttttgag     960
tctgccgcct gccccggttg gttcctctgc acagcgatgg aagctgacca gcccgtcagc    1020
ctcaccaata tgcctgacga aggcgtcatg gtcaccaaat tctacttcca ggaggacgag    1080
taagctt                                                             1087
```

<210> SEQ ID NO 50
<211> LENGTH: 360
<212> TYPE: PRT
<213> ORGANISM: artificial sequence
<220> FEATURE:
<221> NAME/KEY: source
<223> OTHER INFORMATION: /note="Description of artificial sequence: amino acid sequence of the N-terminus of IL-1ra after insertion of PAS'1 polymer sequence"

<400> SEQUENCE: 50

| Glu | Lys | Gly | Ala | Ser | Ser | Ala | Ser | Pro | Ala | Ala | Pro | Ala | Pro | Ala |
|---|---|---|---|---|---|---|---|---|---|---|---|---|---|---|
| 1 | | | | 5 | | | | | 10 | | | | | 15 |

| Ser | Pro | Ala | Ala | Pro | Ala | Pro | Ser | Ala | Pro | Ala | Ala | Ser | Pro | Ala | Ala |
|---|---|---|---|---|---|---|---|---|---|---|---|---|---|---|---|
| | | | 20 | | | | | 25 | | | | | 30 | | |

| Pro | Ala | Pro | Ala | Ser | Pro | Ala | Ala | Pro | Ala | Pro | Ser | Ala | Pro | Ala | Ala |

```
              35                  40                  45
Ser Pro Ala Ala Pro Ala Pro Ala Ser Pro Ala Pro Ala Pro Ser
 50                  55                  60
Ala Pro Ala Ala Ser Pro Ala Ala Pro Ala Pro Ala Ser Pro Ala Ala
 65                  70                  75                  80
Pro Ala Pro Ser Ala Pro Ala Ala Ser Pro Ala Ala Pro Ala Pro Ala
                 85                  90                  95
Ser Pro Ala Ala Pro Ala Pro Ser Ala Pro Ala Ala Ser Pro Ala Ala
                100                 105                 110
Pro Ala Pro Ala Ser Pro Ala Ala Pro Ala Pro Ser Ala Pro Ala Ala
                115                 120                 125
Ser Pro Ala Ala Pro Ala Pro Ala Ser Pro Ala Ala Pro Ala Pro Ser
                130                 135                 140
Ala Pro Ala Ala Ser Pro Ala Ala Pro Ala Pro Ala Ser Pro Ala Ala
145                 150                 155                 160
Pro Ala Pro Ser Ala Pro Ala Ala Ser Pro Ala Ala Pro Ala Pro Ala
                165                 170                 175
Ser Pro Ala Ala Pro Ala Pro Ser Ala Pro Ala Ala Ser Pro Ala Ala
                180                 185                 190
Pro Ala Pro Ala Ser Pro Ala Ala Pro Ala Pro Ser Ala Pro Ala Ala
                195                 200                 205
Arg Pro Ser Gly Arg Lys Ser Lys Met Gln Ala Phe Arg Ile Trp
                210                 215                 220
Asp Val Asn Gln Lys Thr Phe Tyr Leu Arg Asn Asn Gln Leu Val Ala
225                 230                 235                 240
Gly Tyr Leu Gln Gly Pro Asn Val Asn Leu Glu Glu Lys Ile Asp Val
                245                 250                 255
Val Pro Ile Glu Pro His Ala Leu Phe Leu Gly Ile His Gly Gly Lys
                260                 265                 270
Met Cys Leu Ser Cys Val Lys Ser Gly Asp Glu Thr Arg Leu Gln Leu
                275                 280                 285
Glu Ala Val Asn Ile Thr Asp Leu Ser Glu Asn Arg Lys Gln Asp Lys
290                 295                 300
Arg Phe Ala Phe Ile Arg Ser Asp Ser Gly Pro Thr Thr Ser Phe Glu
305                 310                 315                 320
Ser Ala Ala Cys Pro Gly Trp Phe Leu Cys Thr Ala Met Glu Ala Asp
                325                 330                 335
Gln Pro Val Ser Leu Thr Asn Met Pro Asp Glu Gly Val Met Val Thr
                340                 345                 350
Lys Phe Tyr Phe Gln Glu Asp Glu
                355                 360

<210> SEQ ID NO 51
<211> LENGTH: 55
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid sequence of the C-
      terminus of a variant of NGAL carrying the Strep-tag II"

<400> SEQUENCE: 51
cagtgtatcg aggcccccagc ttggtcccac ccgcagttcg aaaaataata agctt        55

<210> SEQ ID NO 52
<211> LENGTH: 15
```

```
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of the C-terminus of a variant of NGAL
      carrying the Strep-tag II"

<400> SEQUENCE: 52

Gln Cys Ile Glu Ala Pro Ala Trp Ser His Pro Gln Phe Glu Lys
1               5                   10                  15

<210> SEQ ID NO 53
<211> LENGTH: 655
<212> TYPE: DNA
<213> ORGANISM: artificial sequence
<220> FEATURE:
<221> NAME/KEY: source
<223> OTHER INFORMATION: /note="Description of artificial sequence:
      nucleic acid sequence encoding amino acid sequence of the C-
      terminus of NGAL after insertion of the PAS#1 polymer sequence
      followed by Strep-tag II"

<400> SEQUENCE: 53
cagtgtatcg aggcctctcc agctgcacct gctccagcaa gccctgctgc accagctccg    60
tctgctcctg ctgcctctcc agctgcacct gctccagcaa gccctgctgc accagctccg   120
tctgctcctg ctgcctctcc agctgcacct gctccagcaa gccctgctgc accagctccg   180
tctgctcctg ctgcctctcc agctgcacct gctccagcaa gccctgctgc accagctccg   240
tctgctcctg ctgcctctcc agctgcacct gctccagcaa gccctgctgc accagctccg   300
tctgctcctg ctgcctctcc agctgcacct gctccagcaa gccctgctgc accagctccg   360
tctgctcctg ctgcctctcc agctgcacct gctccagcaa gccctgctgc accagctccg   420
tctgctcctg ctgcctctcc agctgcacct gctccagcaa gccctgctgc accagctccg   480
tctgctcctg ctgcctctcc agctgcacct gctccagcaa gccctgctgc accagctccg   540
tctgctcctg ctgcctctcc agctgcacct gctccagcaa gccctgctgc accagctccg   600
tctgctcctg ctgccccagc ttggtcccac ccgcagttcg aaaaataata agctt         655

<210> SEQ ID NO 54
<211> LENGTH: 215
<212> TYPE: PRT
<213> ORGANISM: artificial sequence
<220> FEATURE:
<221> NAME/KEY: source
<223> OTHER INFORMATION: /note="Description of artificial sequence:
      amino acid sequence of the C-terminus of NGAL after insertion of
      the PAS#1 polymer sequence followed by Strep-tag II"

<400> SEQUENCE: 54

Gln Cys Ile Glu Ala Ser Pro Ala Ala Pro Ala Pro Ser Pro Ala
1               5                   10                  15

Ala Pro Ala Pro Ser Ala Pro Ala Ala Ser Pro Ala Ala Pro Ala Pro
                20                  25                  30

Ala Ser Pro Ala Ala Pro Ala Pro Ser Ala Pro Ala Ala Ser Pro Ala
        35                  40                  45

Ala Pro Ala Pro Ala Ser Pro Ala Ala Pro Ala Pro Ser Ala Pro Ala
        50                  55                  60

Ala Ser Pro Ala Ala Pro Ala Pro Ser Pro Ala Ala Pro Ala Pro
65                  70                  75                  80

Ser Ala Pro Ala Ala Ser Pro Ala Ala Pro Ala Pro Ser Pro Ala
                85                  90                  95
```

```
Ala Pro Ala Pro Ser Ala Pro Ala Ala Ser Pro Ala Pro Ala Pro
            100                 105                 110

Ala Ser Pro Ala Ala Pro Ala Pro Ser Ala Pro Ala Ala Ser Pro Ala
        115                 120                 125

Ala Pro Ala Pro Ala Ser Pro Ala Ala Pro Ala Pro Ser Ala Pro Ala
    130                 135                 140

Ala Ser Pro Ala Ala Pro Ala Pro Ser Ala Pro Ala Ala Pro Ala Pro
145                 150                 155                 160

Ser Ala Pro Ala Ala Ser Pro Ala Ala Pro Ala Pro Ala Ser Pro Ala
                165                 170                 175

Ala Pro Ala Pro Ser Ala Pro Ala Ala Ser Pro Ala Ala Pro Ala Pro
            180                 185                 190

Ala Ser Pro Ala Ala Pro Ala Pro Ser Ala Pro Ala Ala Pro Ala Trp
        195                 200                 205

Ser His Pro Gln Phe Glu Lys
    210                 215

<210> SEQ ID NO 55
<211> LENGTH: 41
<212> TYPE: DNA
<213> ORGANISM: artificial sequence
<220> FEATURE:
<221> NAME/KEY: source
<223> OTHER INFORMATION: /note="Description of artificial sequence:
      nucleotide sequence stretch of pASK-2x SapI"

<400> SEQUENCE: 55
accgcggaga gtgctcttct gcctgaagag cttaagcttt g                 41

<210> SEQ ID NO 56
<211> LENGTH: 60
<212> TYPE: PRT
<213> ORGANISM: artificial sequence
<220> FEATURE:
<221> NAME/KEY: source
<223> OTHER INFORMATION: /note="Description of artificial sequence:
      three repeated copies of amino acid polymer piSA"

<400> SEQUENCE: 56

Ala Ala Ala Ala Ser Ser Ala Ser Ser Ala Ser Ser Ser Ser Ser Ala
1               5                   10                  15

Ala Ala Ser Ala Ala Ala Ala Ser Ser Ala Ser Ser Ala Ser Ser
            20                  25                  30

Ser Ser Ser Ala Ala Ala Ser Ala Ala Ala Ala Ser Ser Ala Ser
        35                  40                  45

Ser Ala Ser Ser Ser Ser Ser Ala Ala Ala Ser Ala
    50                  55                  60

<210> SEQ ID NO 57
<211> LENGTH: 60
<212> TYPE: PRT
<213> ORGANISM: artificial sequence
<220> FEATURE:
<221> NAME/KEY: source
<223> OTHER INFORMATION: /note="Description of artificial sequence:
      three repeated copies of amino acid polymer PAS#1"

<400> SEQUENCE: 57

Ala Ser Pro Ala Ala Pro Ala Pro Ala Ser Pro Ala Ala Pro Ala Pro
1               5                   10                  15

Ser Ala Pro Ala Ala Ser Pro Ala Ala Pro Ala Pro Ala Ser Pro Ala
            20                  25                  30
```

-continued

Ala Pro Ala Pro Ser Ala Pro Ala Ala Ser Pro Ala Ala Pro Ala Pro
        35                  40                  45

Ala Ser Pro Ala Ala Pro Pro Ser Ala Pro Ala
    50                  55                  60

<210> SEQ ID NO 58
<211> LENGTH: 72
<212> TYPE: PRT
<213> ORGANISM: artificial sequence
<220> FEATURE:
<221> NAME/KEY: source
<223> OTHER INFORMATION: /note="Description of artificial sequence:
      three repeated copies of amino acid polymer PAS#5"

<400> SEQUENCE: 58

Ala Ala Ser Pro Ala Ala Pro Ser Ala Pro Pro Ala Ala Ala Ser Pro
1               5                   10                  15

Ala Ala Pro Ser Ala Pro Pro Ala Ala Ala Ser Pro Ala Ala Pro Ser
            20                  25                  30

Ala Pro Pro Ala Ala Ala Ser Pro Ala Ala Pro Ser Ala Pro Pro Ala
        35                  40                  45

Ala Ala Ser Pro Ala Ala Pro Ser Ala Pro Pro Ala Ala Ala Ser Pro
    50                  55                  60

Ala Ala Pro Ser Ala Pro Pro Ala
65                  70

<210> SEQ ID NO 59
<211> LENGTH: 45
<212> TYPE: DNA
<213> ORGANISM: artificial sequence
<220> FEATURE:
<221> NAME/KEY: source
<223> OTHER INFORMATION: /note="Description of artificial sequence:
      primer"

<400> SEQUENCE: 59
tctgtgggcg ccagctcttc tgcctgtgat ctgcctcaaa cccac                    45

<210> SEQ ID NO 60
<211> LENGTH: 30
<212> TYPE: DNA
<213> ORGANISM: artificial sequence
<220> FEATURE:
<221> NAME/KEY: source
<223> OTHER INFORMATION: /note="Description of artificial sequence:
      primer"

<400> SEQUENCE: 60
gaaccaaagc ttattcctta cttcttaaac                                     30

<210> SEQ ID NO 61
<211> LENGTH: 45
<212> TYPE: DNA
<213> ORGANISM: artificial sequence
<220> FEATURE:
<221> NAME/KEY: source
<223> OTHER INFORMATION: /note="Description of artificial sequence:
      primer"

<400> SEQUENCE: 61
acgatcggcg ccagctcttc tgcccgaccc tctgggagaa aatcc                    45

<210> SEQ ID NO 62
<211> LENGTH: 32
<212> TYPE: DNA
<213> ORGANISM: artificial sequence

```
<220> FEATURE:
<221> NAME/KEY: source
<223> OTHER INFORMATION: /note="Description of artificial sequence:
      primer"

<400> SEQUENCE: 62
ctgggcaagc ttactcgtcc tcctggaagt ag                                     32

<210> SEQ ID NO 63
<211> LENGTH: 20
<212> TYPE: PRT
<213> ORGANISM: artificial sequence
<220> FEATURE:
<221> NAME/KEY: source
<223> OTHER INFORMATION: /note="Description of artificial sequence:
      modified amino acid polymer PAS#3"

<400> SEQUENCE: 63

Ser Ala Pro Ser Ser Pro Ser Pro Ser Ala Pro Ser Ser Pro Ser Pro
1               5                   10                  15

Ala Ser Pro Ser
            20
```